US009334541B2

(12) United States Patent
Rabinowitz et al.

(10) Patent No.: US 9,334,541 B2
(45) Date of Patent: *May 10, 2016

(54) METHODS FOR NON-INVASIVE PRENATAL PLOIDY CALLING

(71) Applicant: Natera, Inc., San Carlos, CA (US)

(72) Inventors: Matthew Rabinowitz, San Francisco, CA (US); George Gemelos, New York, NY (US); Milena Banjevic, Los Altos Hills, CA (US); Allison Ryan, Redwood City, CA (US); Zachary Demko, Los Altos Hills, CA (US); Matthew Hill, Redwood City, CA (US); Bernhard Zimmermann, San Mateo, CA (US); Johan Baner, Stockholm (SE)

(73) Assignee: NATERA, INC., San Carlos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/446,232

(22) Filed: Jul. 29, 2014

(65) Prior Publication Data

US 2014/0336060 A1    Nov. 13, 2014

Related U.S. Application Data

(63) Continuation of application No. 14/179,399, filed on Feb. 12, 2014, and a continuation of application No. 14/100,928, filed on Dec. 9, 2013, now Pat. No. 8,949,036, and a continuation of application No.

(Continued)

(51) Int. Cl.
*G01N 33/48* (2006.01)
*G01N 31/00* (2006.01)

(Continued)

(52) U.S. Cl.
CPC ............ *C12Q 1/6883* (2013.01); *C12Q 1/6827* (2013.01); *C12Q 1/6869* (2013.01);

(Continued)

(58) Field of Classification Search
CPC .. C12Q 1/6809; C12Q 2537/16; G06F 19/10; G06F 19/12; G06F 19/22
See application file for complete search history.

(56) References Cited

U.S. PATENT DOCUMENTS

| 5,635,366 A | 6/1997 | Cooke |
| 5,716,776 A | 2/1998 | Bogart |

(Continued)

FOREIGN PATENT DOCUMENTS

| EP | 1524321 | 7/2009 |
| JP | 2965699 | 8/1999 |

(Continued)

OTHER PUBLICATIONS

"Fixed Medium", dictionary definition, Academic Press Dictionary of Science and Technology [retrieved on Nov. 18, 2009]. Retrieved from the Internet: <URL:www.credoreference.com/entry/apdst/fixed_medium>, (1996),1 pg.

(Continued)

*Primary Examiner* — Larry D Riggs, II
(74) *Attorney, Agent, or Firm* — Anton Bokal

(57) ABSTRACT

The present disclosure provides methods for determining the ploidy status of a chromosome in a gestating fetus from genotypic data measured from a sample of DNA from the mother of the fetus and from the fetus, and from genotypic data from the mother and optionally also from the father. The ploidy state is determined by using a joint distribution model to create a set of expected allele distributions for different possible fetal ploidy states given the parental genotypic data, and comparing the expected allelic distributions to the pattern of measured allelic distributions measured in the mixed sample, and choosing the ploidy state whose expected allelic distribution pattern most closely matches the observed allelic distribution pattern. In an embodiment, the mixed sample of DNA may be preferentially enriched at a plurality of polymorphic loci in a way that minimizes the allelic bias.

30 Claims, 17 Drawing Sheets

Related U.S. Application Data

13/110,685, filed on May 18, 2011, now Pat. No. 8,825,412, said application No. 14/179,399 is a continuation of application No. 13/110,685, filed on May 18, 2011, now Pat. No. 8,825,412, said application No. 14/100,928 is a continuation of application No. 13/110,685, filed on May 18, 2011, now Pat. No. 8,825,412.

(60) Provisional application No. 61/395,850, filed on May 18, 2010, provisional application No. 61/398,159, filed on Jun. 21, 2010, provisional application No. 61/462,972, filed on Feb. 9, 2011, provisional application No. 61/448,547, filed on Mar. 2, 2011, provisional application No. 61/516,996, filed on Apr. 12, 2011.

(51) Int. Cl.

| | |
|---|---|
| *G06G 7/48* | (2006.01) |
| *G06G 7/58* | (2006.01) |
| *C12Q 1/68* | (2006.01) |
| *G06F 19/12* | (2011.01) |
| *G06F 19/22* | (2011.01) |
| *G06F 19/18* | (2011.01) |
| *G06F 19/00* | (2011.01) |

(52) U.S. Cl.
CPC ............... *G06F 19/12* (2013.01); *G06F 19/18* (2013.01); *G06F 19/22* (2013.01); *G06F 19/34* (2013.01); *G06F 19/3431* (2013.01); *C12Q 2600/112* (2013.01); *C12Q 2600/156* (2013.01); *C12Q 2600/16* (2013.01); *C12Q 2600/172* (2013.01)

(56) References Cited

U.S. PATENT DOCUMENTS

| | | | |
|---|---|---|---|
| 5,753,467 | A | 5/1998 | Jensen et al. |
| 5,824,467 | A | 10/1998 | Mascarenhas |
| 5,860,917 | A | 1/1999 | Comanor |
| 5,972,602 | A | 10/1999 | Hyland |
| 5,994,148 | A | 11/1999 | Stewart |
| 6,001,611 | A | 12/1999 | Will |
| 6,025,128 | A | 2/2000 | Veltri |
| 6,108,635 | A | 8/2000 | Herren |
| 6,143,496 | A | 11/2000 | Brown |
| 6,180,349 | B1 | 1/2001 | Ginzinger |
| 6,214,558 | B1 | 4/2001 | Shuber |
| 6,258,540 | B1 | 7/2001 | Lo |
| 6,300,077 | B1 | 10/2001 | Shuber |
| 6,440,706 | B1 | 8/2002 | Vogelstein |
| 6,479,235 | B1 | 11/2002 | Schumm |
| 6,489,135 | B1 | 12/2002 | Parrott |
| 6,720,140 | B1 | 4/2004 | Hartley |
| 6,807,491 | B2 | 10/2004 | Pavlovic |
| 6,852,487 | B1 | 2/2005 | Barany et al. |
| 6,958,211 | B2 | 10/2005 | Vingerhoets |
| 7,035,739 | B2 | 4/2006 | Schadt |
| 7,058,517 | B1 | 6/2006 | Denton |
| 7,058,616 | B1 | 6/2006 | Larder |
| 7,218,764 | B2 | 5/2007 | Vaisberg |
| 7,297,485 | B2 | 11/2007 | Bornarth |
| 7,332,277 | B2 | 2/2008 | Dhallan |
| 7,414,118 | B1 | 8/2008 | Mullah |
| 7,442,506 | B2 | 10/2008 | Dhallan |
| 7,459,273 | B2 | 12/2008 | Jones |
| 7,645,576 | B2 | 1/2010 | Lo |
| 7,700,325 | B2 | 4/2010 | Cantor |
| 7,718,367 | B2 | 5/2010 | Lo |
| 7,718,370 | B2 | 5/2010 | Dhallan |
| 7,727,720 | B2 | 6/2010 | Dhallan |
| 7,805,282 | B2 | 9/2010 | Casey |
| 7,838,647 | B2 | 11/2010 | Hahn |
| 7,888,017 | B2 | 2/2011 | Quake |
| 8,008,018 | B2 | 8/2011 | Quake |
| 8,024,128 | B2 | 9/2011 | Rabinowitz |
| 8,137,912 | B2 | 3/2012 | Kapur |
| 8,168,389 | B2 | 5/2012 | Shoemaker |
| 8,195,415 | B2 | 6/2012 | Fan |
| 8,296,076 | B2 | 10/2012 | Fan |
| 8,304,187 | B2 | 11/2012 | Fernando |
| 8,318,430 | B2 | 11/2012 | Chuu |
| 8,467,976 | B2 | 6/2013 | Lo |
| 8,515,679 | B2 | 8/2013 | Rabinowitz |
| 8,532,930 | B2 | 9/2013 | Rabinowitz |
| 8,682,592 | B2 | 3/2014 | Rabinowitz |
| 8,825,412 | B2 | 9/2014 | Rabinowitz et al. |
| 2001/0053519 | A1 | 12/2001 | Fodor |
| 2002/0006622 | A1 | 1/2002 | Bradley et al. |
| 2003/0009295 | A1 | 1/2003 | Markowitz |
| 2003/0065535 | A1 | 4/2003 | Karlov |
| 2003/0077586 | A1 | 4/2003 | Pavlovic |
| 2003/0101000 | A1 | 5/2003 | Bader |
| 2003/0228613 | A1 | 12/2003 | Bornarth |
| 2004/0033596 | A1 | 2/2004 | Threadgill |
| 2004/0137470 | A1 | 7/2004 | Dhallan |
| 2004/0197797 | A1 | 10/2004 | Inoko |
| 2004/0236518 | A1 | 11/2004 | Pavlovic |
| 2004/0259100 | A1 | 12/2004 | Gunderson |
| 2005/0009069 | A1 | 1/2005 | Liu |
| 2005/0049793 | A1 | 3/2005 | Paterlini-Brechot |
| 2005/0123914 | A1 | 6/2005 | Katz et al. |
| 2005/0142577 | A1 | 6/2005 | Jones |
| 2005/0144664 | A1 | 6/2005 | Smith |
| 2005/0164241 | A1 | 7/2005 | Hahn |
| 2005/0221341 | A1 | 10/2005 | Shimkets et al. |
| 2005/0227263 | A1 | 10/2005 | Green |
| 2005/0250111 | A1 | 11/2005 | Xie |
| 2005/0255508 | A1 | 11/2005 | Casey |
| 2005/0272073 | A1 | 12/2005 | Vaisberg |
| 2006/0019278 | A1 | 1/2006 | Lo |
| 2006/0040300 | A1 | 2/2006 | Dapprich |
| 2006/0052945 | A1 | 3/2006 | Rabinowitz |
| 2006/0057618 | A1 | 3/2006 | Piper |
| 2006/0068394 | A1 | 3/2006 | Langmore |
| 2006/0088574 | A1 | 4/2006 | Manning |
| 2006/0099614 | A1 | 5/2006 | Gill et al. |
| 2006/0121452 | A1 | 6/2006 | Dhallan |
| 2006/0134662 | A1 | 6/2006 | Pratt |
| 2006/0141499 | A1 | 6/2006 | Sher |
| 2006/0210997 | A1 | 9/2006 | Myerson |
| 2006/0216738 | A1 | 9/2006 | Wada |
| 2006/0229823 | A1 | 10/2006 | Liu |
| 2006/0281105 | A1 | 12/2006 | Li et al. |
| 2007/0027636 | A1 | 2/2007 | Rabinowitz |
| 2007/0059707 | A1 | 3/2007 | Cantor |
| 2007/0122805 | A1 | 5/2007 | Cantor |
| 2007/0178478 | A1 | 8/2007 | Dhallan |
| 2007/0178501 | A1 | 8/2007 | Rabinowitz |
| 2007/0184467 | A1 | 8/2007 | Rabinowitz |
| 2007/0202525 | A1 | 8/2007 | Quake |
| 2007/0202536 | A1 | 8/2007 | Yamanishi |
| 2007/0207466 | A1 | 9/2007 | Cantor |
| 2007/0212689 | A1 | 9/2007 | Bianchi |
| 2007/0243549 | A1 | 10/2007 | Bischoff |
| 2007/0259351 | A1 | 11/2007 | Chinitz |
| 2008/0020390 | A1 | 1/2008 | Mitchell |
| 2008/0026390 | A1 | 1/2008 | Stoughton |
| 2008/0038733 | A1 | 2/2008 | Bischoff |
| 2008/0070792 | A1 | 3/2008 | Stoughton |
| 2008/0071076 | A1 | 3/2008 | Hahn |
| 2008/0085836 | A1 | 4/2008 | Kearns |
| 2008/0102455 | A1 | 5/2008 | Poetter |
| 2008/0138809 | A1 | 6/2008 | Kapur |
| 2008/0182244 | A1 | 7/2008 | Tafas |
| 2008/0193927 | A1 | 8/2008 | Mann |
| 2008/0234142 | A1 | 9/2008 | Lietz |
| 2008/0243398 | A1 | 10/2008 | Rabinowitz |
| 2009/0023190 | A1 | 1/2009 | Lao |
| 2009/0029377 | A1 | 1/2009 | Lo |
| 2009/0087847 | A1 | 4/2009 | Lo et al. |
| 2009/0098534 | A1 | 4/2009 | Weier |

(56) References Cited

U.S. PATENT DOCUMENTS

| | | |
|---|---|---|
| 2009/0099041 A1 | 4/2009 | Church |
| 2009/0176662 A1 | 7/2009 | Rigatti |
| 2009/0221620 A1 | 9/2009 | Luke et al. |
| 2010/0035232 A1 | 2/2010 | Ecker |
| 2010/0112575 A1 | 5/2010 | Fan |
| 2010/0112590 A1 | 5/2010 | Lo |
| 2010/0120038 A1 | 5/2010 | Mir |
| 2010/0124751 A1 | 5/2010 | Quake |
| 2010/0138165 A1 | 6/2010 | Fan |
| 2010/0171954 A1 | 7/2010 | Quake |
| 2010/0184069 A1 | 7/2010 | Fernando |
| 2010/0184152 A1 | 7/2010 | Sandler |
| 2010/0196892 A1 | 8/2010 | Quake |
| 2010/0203538 A1 | 8/2010 | Dube |
| 2010/0216153 A1 | 8/2010 | Lapidus |
| 2010/0248231 A1 | 9/2010 | Wei |
| 2010/0255492 A1 | 10/2010 | Quake |
| 2010/0256013 A1 | 10/2010 | Quake |
| 2010/0285537 A1 | 11/2010 | Zimmermann |
| 2010/0291572 A1 | 11/2010 | Stoughton |
| 2010/0323352 A1 | 12/2010 | Lo |
| 2011/0033862 A1 | 2/2011 | Rabinowitz |
| 2011/0039724 A1 | 2/2011 | Lo |
| 2011/0092763 A1 | 4/2011 | Rabinowitz |
| 2011/0105353 A1 | 5/2011 | Lo |
| 2011/0151442 A1 | 6/2011 | Fan |
| 2011/0178719 A1 | 7/2011 | Rabinowitz |
| 2011/0201507 A1 | 8/2011 | Rava |
| 2011/0224087 A1 | 9/2011 | Quake |
| 2011/0246083 A1 | 10/2011 | Fan |
| 2011/0251149 A1 | 10/2011 | Perrine |
| 2011/0288780 A1 | 11/2011 | Rabinowitz |
| 2011/0300608 A1 | 12/2011 | Ryan |
| 2011/0318734 A1 | 12/2011 | Lo |
| 2012/0003635 A1 | 1/2012 | Lo |
| 2012/0034603 A1 | 2/2012 | Oliphant |
| 2012/0122701 A1 | 5/2012 | Ryan |
| 2012/0165203 A1 | 6/2012 | Quake |
| 2012/0185176 A1 | 7/2012 | Rabinowitz |
| 2012/0190020 A1 | 7/2012 | Oliphant |
| 2012/0190021 A1 | 7/2012 | Oliphant |
| 2012/0196754 A1 | 8/2012 | Quake |
| 2012/0214678 A1 | 8/2012 | Rava |
| 2012/0264121 A1 | 10/2012 | Rava |
| 2012/0270212 A1 | 10/2012 | Rabinowitz |
| 2013/0017549 A1 | 1/2013 | Hong |
| 2013/0024127 A1 | 1/2013 | Stuelpnagel |
| 2013/0034546 A1 | 2/2013 | Rava |
| 2013/0060483 A1 | 3/2013 | Struble |
| 2013/0069869 A1 | 3/2013 | Akao |
| 2013/0090250 A1 | 4/2013 | Sparks |
| 2013/0123120 A1 | 5/2013 | Zimmermann |
| 2013/0178373 A1 | 7/2013 | Rabinowitz |
| 2013/0190653 A1 | 7/2013 | Alvarez Ramos |
| 2013/0196862 A1 | 8/2013 | Rabinowitz |
| 2013/0210644 A1 | 8/2013 | Stoughton |
| 2013/0225422 A1 | 8/2013 | Rabinowitz |
| 2013/0252824 A1 | 9/2013 | Rabinowitz |
| 2013/0253369 A1 | 9/2013 | Rabinowitz |
| 2013/0261004 A1 | 10/2013 | Ryan |
| 2013/0274116 A1 | 10/2013 | Rabinowitz |
| 2013/0303461 A1 | 11/2013 | Iafrate |
| 2013/0323731 A1 | 12/2013 | Lo |
| 2014/0032128 A1 | 1/2014 | Rabinowitz |
| 2014/0051585 A1 | 2/2014 | Prosen |
| 2014/0065621 A1 | 3/2014 | Mhatre |
| 2014/0087385 A1 | 3/2014 | Rabinowitz |
| 2014/0094373 A1 | 4/2014 | Zimmermann |
| 2014/0100126 A1 | 4/2014 | Rabinowitz |
| 2014/0100134 A1 | 4/2014 | Rabinowitz |
| 2014/0141981 A1 | 5/2014 | Zimmermann |
| 2014/0154682 A1 | 6/2014 | Rabinowitz |
| 2014/0162269 A1 | 6/2014 | Rabinowitz |
| 2014/0193816 A1 | 7/2014 | Rabinowitz |
| 2014/0206552 A1 | 7/2014 | Rabinowitz |
| 2014/0256569 A1 | 9/2014 | Rabinowitz |
| 2014/0336060 A1 | 11/2014 | Rabinowitz |

FOREIGN PATENT DOCUMENTS

| | | |
|---|---|---|
| JP | 2004502466 A | 1/2004 |
| JP | 2004533243 A | 11/2004 |
| JP | 2005514956 A | 5/2005 |
| JP | 2005160470 A | 6/2005 |
| WO | WO9114768 | 10/1991 |
| WO | WO0179851 | 10/2001 |
| WO | 0190419 A2 | 11/2001 |
| WO | WO0190419 | 11/2001 |
| WO | WO-0204672 A2 | 1/2002 |
| WO | WO02055985 | 7/2002 |
| WO | WO03031646 | 4/2003 |
| WO | WO03050532 | 6/2003 |
| WO | WO-03062441 A1 | 7/2003 |
| WO | WO03102595 | 12/2003 |
| WO | WO03106623 | 12/2003 |
| WO | WO2004087863 | 10/2004 |
| WO | WO2005021793 | 3/2005 |
| WO | WO-2005035725 A2 | 4/2005 |
| WO | WO2005100401 | 10/2005 |
| WO | WO2005123779 | 12/2005 |
| WO | WO2007057647 | 5/2007 |
| WO | WO2007062164 | 5/2007 |
| WO | WO2007070482 | 6/2007 |
| WO | WO2007132167 | 11/2007 |
| WO | W02007147074 A2 | 12/2007 |
| WO | WO-2008024473 A2 | 2/2008 |
| WO | WO2008048931 | 4/2008 |
| WO | WO2008051928 | 5/2008 |
| WO | WO-2008081451 A2 | 7/2008 |
| WO | WO2008115497 | 9/2008 |
| WO | WO2008135837 | 11/2008 |
| WO | WO2008157264 | 12/2008 |
| WO | WO2009009769 | 1/2009 |
| WO | WO2009013492 | 1/2009 |
| WO | WO2009013496 | 1/2009 |
| WO | WO2009019215 | 2/2009 |
| WO | WO2009019455 | 2/2009 |
| WO | WO2009030100 | 3/2009 |
| WO | WO2009032779 | 3/2009 |
| WO | WO2009032781 | 3/2009 |
| WO | WO2009033178 | 3/2009 |
| WO | WO2009091934 | 7/2009 |
| WO | WO2009092035 | 7/2009 |
| WO | WO2009105531 | 8/2009 |
| WO | WO2009146335 | 12/2009 |
| WO | WO2010017214 | 2/2010 |
| WO | WO2011041485 | 4/2011 |
| WO | WO2011146632 | 11/2011 |
| WO | 2012071621 | 6/2012 |
| WO | WO2012071621 | 6/2012 |
| WO | WO2012088456 | 6/2012 |
| WO | WO2012108920 | 8/2012 |
| WO | WO2013052557 | 4/2013 |
| WO | 2013130848 | 9/2013 |
| WO | WO2013130848 | 9/2013 |
| WO | 2014018080 | 1/2014 |
| WO | WO2014018080 | 1/2014 |

OTHER PUBLICATIONS

"Finishing the Euchromatic Sequence of the Human Genome", Nature vol. 431, (Oct. 21, 2004),931-945.

"Multiplexing with RainDrop Digital PCR", RainDance Technologies Application Note, (2013), 1-2.

"Nucleic Acids, Linkers and Primers: Random Primers" New England BioLabs 1998/1999 Catalog, (1998), 121 and 284.

"Competitive PCR Guide", TaKaRa Biomedicals, Lit. # L0126 Rev. Aug. 1999, 9 pgs.

"Genetics Home Reference", http://ghr.nlm.nih.gov/handbook/genomicresearch/snp, (Feb. 28, 2014),1-2.

"Ion AmpliSeq Comprehensive Cancer Panel", product brochure, Life Technologies Corporation. Retrieved from the Internet <URL:

(56) References Cited

OTHER PUBLICATIONS https://tools.lifetechnologies.com/content/sfs/brochures/Ion_CompCancerPanel_Flyer.pdf>, (2012),2 pgs.
"Ion AmpliSeq Designer Provides Full Flexibility to Sequence Genes of Your Choice", product brochure, Life Technologies Corporation. Retrieved from the Internet <URL: http://tools.lifetechnologies.com/content/sfs/brochures/IonAmpliSeq_CustomPanels_AppNote_CO111038_06042012.pdf>, (2012),4 pgs.
"Primer3", information sheet, Sourceforge.net. [retrieved on Nov. 12, 2012]. Retrieved from the Internet: <URL: http://primer3.sourceforge.net/>, (Oct. 26, 2009),1 pg.
Abidi, et al., "Leveraging XML-based Electronic Medical Records to Extract Experimental Clinical Knowledge: An Automated approach to generate cases for medical case-based reasoning systems", International Journal of Medical Informatics, 68, (2002),187-203.
Agarwal, et al., "Commercial Landscape of Noninvasive Prenatal Testing in the United States", Prenatal Diagnosis, 33, (2013),521-531.
Alkan, et al., "Personalized Copy Number and Segmental Duplication Maps Using Next-Generation Sequencing", Nature Genetics, vol. 41, No. 10, (Oct. 2009),1061-1068.
Allaire, "Mate Selection by Selection Index Theory", Theor. Appl. Genet., 57, (1980),267-272.
Allawi, et al., "Thermodynamics of internal C•T Mismatches in DNA", Nucleic Acids Research, vol. 26, No. 11, (1998),2694-2701.
Ashoor, et al., "Chromosome-Selective Sequencing of Maternal Plasma Cell-Free DNA for First-Trimester Detection of Trisomy 21 and Trisomy 18", American Journal of Obstetrics & Gynecology, 206, (Apr. 2012),322.e1-322.e5.
Ashoor, et al., "Fetal Fraction in Maternal Plasma Cell-Free DNA at 11-13 Weeks' Gestation: Effect of Maternal and Fetal Factors", Fetal Diagnosis Therapy, (May 4, 2012),1-7.
Bada, et al., "Computational Modeling of Structural Experimental Data", Methods in Enzymology, vol. 317, (2000),470-491.
Beaumont, et al., "The Bayesian Revolution in Genetics", Nature Reviews Genetics, vol. 5, (Apr. 2004),251-261.
Beer, et al., "The Biological Basis of Passage of Fetal Cellular Material into the Maternal Circulation", Annals New York Academy of Sciences, 731, (1994),21-35.
Beerenwinkel, et al., "Geno2pheno: Estimating Phenotypic Drug Resistance from HIV-1 Genotypes", Nucleic Acids Research, vol. 31, No. 13, (2003),3850-3855.
Beerenwinkel, et al., "Methods for Optimizing Antiviral Combination Therapies", Bioinformatics, vol. 19, Suppl. 1, (2003),i16-i25.
Benn, et al., "Non-Invasive prenatal Diagnosis for Down Syndrome: the Paradigm Will Shift, but Slowly", Ultrasound Obstet. Gynecol., 39, (2012),127-130.
Benn, et al., "Non-Invasive Prenatal Testing for Aneuploidy: Current Status and Future Prospects", Ultrasound Obstet. Gynecol., 42, (2013),15-33.
Bermudez, et al., "Single-cell sequencing and mini-sequencing for preimplantation genetic diagnosis", Prenatal Diagnosis, vol. 23, (2003),669-677.
Birch, et al., "Accurate and Robust Quantification of Circulating Fetal and Total DNA in Maternal Plasma from 5 to 41 Weeks of Gestation", Clinical Chemistry, vol. 51, No. 2, (2005),312-320.
Bisignano, et al., "PGD and Aneuploidy Screening for 24 Chromosomes: Advantages and Disadvantages of Competing Platforms", Reproductive BioMedicine Online, 23, (2011),677-685.
Bodenreider, "The Unified Medical Language System (UMLS): Integrating Biomedical Terminology", Nucleic Acids Research, vol. 32 (Database issue), (2004),D267-D270.
Breithaupt, "The Future of Medicine", EMBO Reports, vol. 2, No. 61, (2001),465-467.
Brownie, et al., "The Elimination of Primer-Dimer Accumulation in PCR", Nucleic Acids Research, vol. 25, No. 16, (1997),3235-3241.
Cairns, "Homozygous Deletions of 9p21 in Primary Human Bladder Tumors Detected by Comparative Multiplex Polymerase Chain Reaction", Cancer Research vol. 54, (1994), 1422-1424.
Caliendo, "Multiplex PCR and Emerging Technologies for the Detection of Respiratory Pathogens", Clinical Infection Diseases vol. 52, Suppl. 4, (2011), S326-S330.
Carnevale, et al., "Attitudes of Mexican Geneticists Towards Prenatal Diagnosis and Selective Abortion", American Journal of Medical Genetics, 75, (1998),426-431.
Chen, et al., "Noninvasive Prenatal Diagnosis of Fetal Trisomy 18 and Trisomy 13 by Maternal Plasma DNA Sequencing", PLoS ONE, vol. 6, Issue 7, e21791, (Jul. 2011),7 pgs.
Chetty, et al., "Uptake of Noninvasive Prenatal Testing (NIPT) in Women Following Positive Aneuploidy Screening", Prenatal Diagnosis, 33, (2013),542-546.
Chiu, et al., "Maternal Plasma DNA Analysis with Massively Parallel Sequencing by Litigation for Noninvasive Prenatal Diagnosis of Trisomy 21", Clinical Chemistry, vol. 56, No. 3, (2010),459-463.
Chiu, et al., "Non-Invasive Prenatal Assessment of Trisomy 21 by Multiplexed Maternal Plasma DNA Sequencing: Large Scale Validity Study", BMJ, vol. 342, c7401, (2011),9 pgs.
Chiu, et al., "Non-Invasive Prenatal Diagnosis by Single Molecule Counting Technologies", Trends in Genetics, vol. 25, No. 7, (2009),324-331.
Chiu, et al., "Noninvasive Prenatal Diagnosis of Fetal Chromosomal Aneuploidy by Massively Parallel Genomic Sequencing of DNA in Maternal Plasma", PNAS, vol. 105, No. 51 (with Supporting Information), (Dec. 23, 2008),23 pgs.
Chu, et al., "A Novel Approach Toward the Challenge of Accurately Quantifying Fetal DNA in Maternal Plasma", Prenatal Diagnosis, 30, (2010),1226-1229.
Chu, et al., "Statistical Considerations for Digital Approaches to Non-Invasive Fetal Genotyping", Bioinformatics (Advance Access publication), vol. 26, No. 22, (2010),2863-2866.
Chu, et al., "Statistical Model for Whole Genome Sequencing and its Application to Minimally Invasive Diagnosis of Fetal Genetic Disease", Bioinformatics, vol. 25, No. 10, (2009),1244-1250.
Colella, et al., "QuantiSNP: an Objectives Bayes Hidden-Markov Model to Detect and Accurately Map Copy Number Variation Using SNP Genotyping Data", Nucleic Acids Research, vol. 35, No. 6, (2007),2013-2025.
Cossu, et al., "Rh D/d Genotyping by Quantitative Polymerase Chain Reaction and Capillary Zone Electrophoresis", Electrophoresis, 17, (1996),1911-1915.
Coyle, et al., "Standards for Detailed Clinical Models as the Basis for Medical Data Exchange and Decision Support", International Journal of Medical Informatics, 69, (2003),157-174.
D'Aquila, et al., "Maximizing Sensitivity and Specificity of PCR by Pre-Amplification Heating", Nucleic Acids Research, vol. 19, No. 13, (1991),3749.
Daruwala, et al., "A Versatile Statistical Analysis Algorithm to Detect Genome Copy Number Variation", PNAS, vol. 101, No. 46, (Nov. 16, 2004),16292-16297.
Deangelis, et al., "Solid-phase Reversible Immobilization for the Isolation of PCR Products", Nucleic Acids Research, vol. 23, No. 22, (Nov. 25, 1995),4742-4743.
Devaney, et al., "Noninvasive Fetal Sex Determination Using Cell-Free Fetal DNA: A Systematic Review and Meta-analysis", JAMA, vol. 306, No. 6, (Aug. 10, 2011),627-636.
Dhallan, et al., "A Non-Invasive Test for Prenatal Diagnosis Based on Fetal DNA Present in Maternal Blood: A Preliminary Study", Lancet, vol. 369, (Feb. 10, 2007),474-481.
Dhallan, et al., "Methods to Increase the Percentage of Free Fetal DNA Recovered from the Maternal Circulation", JAMA, vol. 291, No. 9, (Mar. 3, 2004),1114-1119.
Dieffenbach, "General Concepts for PCR Primer Design", PCR Methods Appl. vol. 3, (1993), 30-37.
Dohm, et al., "Substantial Biases in Ultra-Short Read Data Sets From High-Throughput DNA Sequencing", Nucleic Acids Research, vol. 36, No. 16, e105, (2008),10 pgs.
Dolganov, et al., "A Novel Method of Gene Transcript Profiling in Airway Biopsy Homogenates Reveals Increased Expression of a Na +-K+-Cl- Contransporter (NKCC1) in Asthmatic Subjects", Genome Res. 2001, vol. 11, (2001),1473-1483.

(56) References Cited

OTHER PUBLICATIONS

Donoso, et al., "Current Value of Preimplantation Genetic Aneuploidy Screening in IVF", Human Reproduction Update, vol. 13, No. 1, (2007),15-25.
Enrich, et al., "Noninvasive Detection of Fetal Trisomy 21 by Sequencing of DNA in Maternal Blood: A Study in a Clinical Setting", American Journal of Obstetrics & Gynecology, 204, (2011),205.e1-205.e11.
Eichler, et al., "Mild Course of Fetal Rh D Haemolytic Disease due to Maternal Alloimmunisation to Paternal HLA Class I and II Antigens", Vox Sang, 68, (1995),243-247.
Ellonen, et al., "Development of SNP Microarray for Supplementary Paternity Testing", International Congress Series, vol. 1261, (2004),12-14.
European Application No. 06838311.6, Communication and Extended European Search Report mailed Dec. 30, 2008, 8 pgs.
European Application No. 08742125.1, Communication pursuant to Article 94(3) EPC and Examination Report mailed Feb. 12, 2010, 5 pgs.
Fan, "Highly Parallel Genomic Assay", Nature Reviews, vol. 7, Aug. 2006, 632-644.
Fan, et al., "Noninvasive Diagnosis of Fetal Aneuploidy by Shotgun Sequencing DNA from Maternal Blood", PNAS, vol. 105, No. 42, (Oct. 21, 2008),16266-16271.
Fan, et al., "Non-Invasive Prenatal Measurement of the Fetal Genome", Nature, doi:10.1038/nature11251 (with Supplemental Information), (2012),26 pgs.
Fazio, et al., "Identification of RAPD Markers Linked to Fusarium Crown and Root Rot Resistance (Frl) in Tomato", Euphytica 105, (Mar. 1, 1999),205-210.
Fiorentino, et al., "Development and Clinical Application of a Strategy for Preimplantation Genetic Diagnosis of Single Gene Disorders Combined with HLA Matching", Molecular Human Reproduction (Advance Access publication), vol. 10, No. 6, (2004),445-460.
Fiorentino, et al., "Short Tandem Repeats Haplotyping of the HLA Region in Preimplantation HLA Matching", European Journal of Human Genetics, 13, (2005),953-958.
Fiorentino, et al., "Strategies and Clinical Outcome of 250 Cycles of Preimplantation Genetic Diagnosis for Single Gene Disorders", Human Reproduction, vol. 21, No. 3, (2006),670-684.
Freeman, et al., "Copy Number Variation: New Insights in Genome Diversity", Genome Research, 16, (2006),949-961.
Ganshirt-Ahlert, et al., "Fetal DNA in Uterine Vein Blood", Obstetrics & Gynecology, 80, (1992),601-603.
Ganshirt-Ahlert, et al., "Ratio of Fetal to Maternal DNA is Less Than 1 in 5000 at different Gestational Ages in Maternal Blood", Clinical Genetics, 38, (1990),38-43.
Ganshirt-Ahlert, et al., "Three Cases of 45,X/46,XYnf Mosaicism", Human Genetics, 76, (1987),153-156.
Gardina, et al., "Ploidy Status and Copy Number Aberrations in Primary Glioblastomas Defined by Integrated Analysis of Allelic Ratios, Signal Ratios and Loss of Heterozygosity Using 500K SnNP Mapping Arrays", BMC Genomics, vol. 9, No. 489 (doi:10.1186/1471-2164-9-489), (2008),16 pgs.
Ghanta, et al., "Non-Invasive Prenatal Detection of Trisomy 21 Using Tandem Single Nucleotide Polymorphisms", PLoS ONE, vol. 5, Issue 10, e13184, (Oct. 2010),10 pgs.
Gjertson, et al., "Assessing Probability of Paternity and the Product Rule in DNA Systems", Genetica, 96, (1995),89-98.
Greenwalt, et al., "The Quantification of Fetomaternal Hemorrhage by an Enzyme-Linked Antibody Test with Glutaraldehyde Fixation", Vox Sang, 63, (1992),268-271.
Guerra, et al., "Terminal Contributions for Duplex Oligonucleotide Thermodynamic Properties in the Context of Nearest Neighbor Models", Biopolymers, vol. 95, No. 3, (2011),194-201.
Guetta, et al., "Analysis of Fetal Blood Cells in the Maternal Circulation: Challenges, Ongoing Efforts, and Potential Solutions", Stem Cells and Development, 13, (2004),93-99.
Guichoux, et al., "Current Trends in Microsatellite Genotyping", Molecular Ecology Resources, 11, (2011),591-611.
Hara, et al., "Subtractive cDNA Cloning Using Oligo(dT)30-latex and PCR: Isolation of cDNA Clones Specific to Undifferentiated Human Embryonal Carcinoma Cells", Nucleic Acids Research, vol. 19, No. 25, (1991),7097-7104.
Hardenbol, et al., "Multiplexed Genotyping With Sequence-Tagged Molecular Inversion Probes", Nature Biotechnology vol. 21, No. 6, (Jun. 2003),673-678.
Harper, et al., "Recent Advances and Future Developments in PGD", Prenatal Diagnosis, 19, (1999),1193-1199.
Harton, et al., "Preimplantation Genetic Testing for Marfan Syndrome", Molecular Human Reproduction, vol. 2, No. 9, (1996),713-715.
Hellani, et al., "Clinical Application of Multiple Displacement Amplification in Preimplantation Genetic Diagnosis", Reproductive BioMedicine Online, vol. 10, No. 3, (2005),376-380.
Hellani, et al., "Multiple displacement amplification on single cell and possible PGD applications", Molecular Human Reproduction (advance access publication), vol. 10, No. 11, (Oct. 1, 2004),847-852.
Hojsgaard, et al., "BIFROST—Block Recursive Models Induced from Relevant Knowledge, Observations, and Statistical Techniques", Computational Statistics & Data Analysis, 19, (1995),155-175.
Hollox, et al., "Extensive Normal Copy Number Variation of a β-Defensin Antimicrobial-Gene Cluster", Am. J. Hum. Genet., 73, (2003),591-600.
Homer, et al., "Resolving Individuals Contributing Trace Amounts of DNA to Highly Complex Mixtures Using High-Density SNP Genotyping Microarrays", PLOS Genetics, vol. 4, Issue 8, e1000167, (Aug. 2008),9 pgs.
Hoogendoorn, "Genotyping Single Nucleotide Polymorphisms by Primer Extension and High Performance Liquid Chromatography", Hum Genet vol. 104, (1999), 89-93.
Hu, et al., "Aneuploidy Detection in Single Cells Using DNA Array-Based Comparative Genomic Hybridization", Molecular Human Reproduction, vol. 10, No. 4, (2004),283-289.
International Application No. PCT/US2006/045281, International Preliminary Report on Patentability mailed May 27, 2008, 1 pg.
International Application No. PCT/US2006/045281, International Search Report and Written Opinion mailed Sep. 28, 2007, 7 pgs.
International Application No. PCT/US2008/003547, International Search Report mailed Apr. 15, 2009, 5 pgs.
International Application No. PCT/US2009/034506, International Search Report mailed Jul. 8, 2009, 2 pgs.
International Application No. PCT/US2009/045335, International Search Report mailed Jul. 27, 2009, 1 pg.
International Application No. PCT/US2009/052730, International Search Report mailed Sep. 28, 2009, 1 pg.
International Application No. PCT/US2010/050824, International Search Report mailed Nov. 15, 2010, (2 pgs.).
International Application No. PCT/US2011/037018, International Search Report mailed Sep. 27, 2011, 2 pgs.
International Application No. PCT/US2011/061506, International Search Report mailed Mar. 16, 2012, 1 pgs.
International Application No. PCT/US2011/066938, International Search Report mailed Jun. 20, 2012, 1 pg.
International Application No. PCT/US2012066339, International Search Report mailed Mar. 5, 2013, 1 pg.
International Application No. PCT/US2013/028378, International Search Report and Written Opinion mailed May 28, 2013, 11 pgs.
International Application No. PCT/US2013/57924, International Search Report and Written Opinion mailed Feb. 18, 2014, 8 pgs.
Johnson, et al., "Comprehensive Analysis of Karyotypic Mosaicism Between Trophectoderm and Inner Cell Mass", Molecular Human Reproduction, vol. 16, No. 12, (2010),944-949.
Johnson, et al., "Preclinical Validation of a Microarray Method for Full Molecular Karyotyping of Blastomeres in a 24-h Protocol", Human Reproduction, vol. 25, No. 4, (2010),1066-1075.
Kaplinski, et al., "MultiPLX: Automatic Grouping and Evaluation of PCR Primers", Bioinformatics (Advance Access publication), vol. 21, No. 8, (2005),1701-1702.
Kazakov, et al., "Extracellular DNA in the Blood of Pregnant Women", Tsitologia, vol. 37, No. 3, (1995),8 pgs.

(56) References Cited

OTHER PUBLICATIONS

Kijak, et al., "Discrepant Results in the Interpretation of HIV-1 Drug-Resistance Genotypic Data Among Widely Used Algorithms", HIV Medicine, 4, (2003),72-78.

Konfortov, et al., "An Efficient Method for Multi-Locus Molecular Haplotyping", Nucleic Acids Research, vol. 35, No. 1, e6, (2007),8 pgs.

Kuliev, et al., "Thirteen Years' Experience on Preimplantation Diagnosis: Report of the Fifth International Symposium on Preimplantation Genetics", Reproductive BioMedicine Online, vol. 8, No. 2, (2004),229-235.

Lambert-Messerlian, et al., "Adjustment of Serum Markers in First Trimester Screening", Journal of Medical Screening, vol. 16, No. 2, (2009),102-103.

Lathi, et al., "Informatics Enhanced SNP Microarray Analysis of 30 Miscarriage Samples Compared to Routine Cytogenetics", PLoS ONE, vol. 7, Issue 3, e31282, (Mar. 2012),5 pgs.

Leary, et al., "Detection of Chromosomal Alterations in the Circulation of Cancer Patients with Whole-Genome Sequencing", Science Translational Medicine, vol. 4, Issue 162, (Nov. 28, 2012),12 pgs.

Li, et al., "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL:http://www.ashg.org/2012meeting/abstracts/fulltext/f120121811.htm>, (2012),1 pg.

Li, et al., "Non-Invasive Prenatal Diagnosis Using Cell-Free Fetal DNA in Maternal Plasma from PGD Pregnancies", Reproductive BioMedicine Online, vol. 19, No. 5, (2009),714-720.

Li, et al., "Size Separation of Circulatory DNA in Maternal Plasma Permits Ready Detection of Fetal DNA Polymorphisms", Clinical Chemistry, vol. 50, No. 6, (2004),1002-1011.

Liao, et al., "Targeted Massively Parallel Sequencing of Maternal Plasma DNA Permits Efficient and Unbiased Detection of Fetal Alleles", Clinical Chemistry, vol. 57, No. 1, (2011),92-101.

Lindroos, et al., "Genotyping SNPs by Minisequencing Primer Extension Using Oligonucleotide Microarrays", Methods in Molecular Biology, vol. 212—Single Nucleotide Polymorphisms: Methods and Protocols, P-K Kwok (ed.), Humana Press, Inc., Totowa, NJ, (2003),149-165.

Lo, "Fetal Nucleic Acids in Maternal Plasma: Toward the Development of Noninvasive Prenatal Diagnosis of Fetal Chromosomal Aneuploidies", Ann. N.Y. Acad. Sci., 1137, (2008),140-143.

Lo, "Non-Invasive Prenatal Diagnosis by Massively parallel Sequencing of Maternal Plasma DNA", Open Biol 2: 120086, (2012),1-5.

Lo, et al., "Detection of Fetal RhD Sequence from Peripheral Blood of Sensitized RhD-Negative Pregnant Women", British Journal of Haematology, 87, (1994),658-660.

Lo, et al., "Detection of Single-Copy Fetal DNA Sequence from Maternal Blood", The Lancet, vol. 335, (Jun. 16, 1990), 1463-1464.

Lo, et al., "Digital PCR for the Molecular Detection of Fetal Chromosomal Aneuploidy", PNAS, vol. 104, No. 32, (Aug. 7, 2007),13116-13121.

Lo, et al., "Fetal Nucleic Acids in Maternal Blood: the Promises", Clin. Chem. Lab. Med., vol. 50, No. 6, (2012),995-998.

Lo, et al., "Free Fetal DNA in Maternal Circulation", JAMA, vol. 292, No. 23 (Letters to the Editor), (Dec. 15, 2004),2835-2836.

Lo, et al., "Maternal Plasma DNA Sequencing Reveals the Genome-Wide Genetic and Mutational Profile of the Fetus", Science Translational Medicine, vol. 2, Issue 61, (Dec. 8, 2010), 13 pgs.

Lo, et al., "Plasma Placental RNA Allelic Ratio Permits Noninvasive Prenatal Chromosomal Aneuploidy Detection", Nature Medicine, vol. 13, No. 2, (Feb. 2007),218-223.

Lo, et al., "Prenatal Determination of Fetal RhD Status by Analysis of Peripheral Blood of Rhesus Negative Mothers", The Lancet, vol. 341, (Letters to the Editor), (May 1, 1993),1147-1148.

Lo, et al., "Prenatal Determination of Fetal Rhesus D Status by DNA Amplification of Peripheral Blood of Rhesus-Negative Mothers", Annals New York Academy of Sciences, 731, (Sep. 7, 1994),229-236.

Lo, et al., "Prenatal Sex Determination by DNA Amplification from Maternal Peripheral Blood", The Lancet, vol. 2, No. 8676, (Dec. 9, 1989),1363-1365.

Lo, et al., "Presence of Fetal DNA in Maternal Plasma and Serum", The Lancet, vol. 350, (Aug. 16, 1997),485-487.

Lo, et al., "Quantitative Analysis of Fetal DNA in Maternal Plasma and Serum: Implications for Noninvasive Prenatal Diagnosis", Am. J. Hum. Genet. 62, (1998),768-775.

Lo, et al., "Rapid Clearance of Fetal DNA from Maternal Plasma", Am. J. Hum. Genet., 64, (1999),218-224.

Lo, et al., "Strategies for the Detection of Autosomal Fetal DNA Sequence from Maternal Peripheral Blood", Annals New York Academy of Sciences, 731, (1994),204-213.

Lo, et al., "Two-way cell traffic between mother and fetus: biologic and clinical implications", Blood, vol. 88, No. 11, (Dec. 1, 1996),4390-4395.

Lun, et al., "Noninvasive Prenatal Diagnosis of Monogenic Diseases by Digital Size Selection and Relative Mutation Dosage on DNA in Maternal Plasma", PNAS, vol. 105, No. 50, (Dec. 16, 2008),19920-19925.

Maniatis, et al., In: Molecular Cloning: A Laboratory Manual, Cold Spring Harbor Laboratory, New York, Thirteenth Printing, (Sep. 1986),458-459.

Mansfield, "Diagnosis of Down Syndrome and Other Aneuploidies Using Quantitative Polymerase Chain Reaction and Small Tandem Repeat Polymorphisms", Human Molecular Genetics, vol. 2, No. 1, (1993),43-50.

May, "How Many Species Are There on Earth?", Science vol. 241, (Sep. 16, 1988),1441-1449.

McCray, et al., "Aggregating UMLS Semantic Types for Reducing Conceptual Complexity", MEDINFO 2001: Proceedings of the 10th World Congress on Medical Informatics (Studies in Health Technology and Informatics, 84), V. Patel et al. (eds.), IOS Press, Amsterdam, (2001),216-220.

Mennuti, et al., "Is It Time to Sound an Alarm About False-Positive Cell-Free DNA Testing for Fetal Aneuploidy?", American Journal of Obstetrics, (2013),5 pgs.

Mersy, et al., "Noninvasive Detection of Fetal Trisomy 21: Systematic Review and Report of Quality and Outcomes of Diagnostic Accuracy Studies Performed Between 1997 and 2012", Human Reproduction Update, vol. 19, No. 4, (2013),318-329.

Munne, et al., "Chromosome Abnormalities in Human Embryos", Textbook of Assisted Reproductive Techniques, (2004),355-377.

Murtaza, et al., "Non-Invasive Analysis of Acquired Resistance to Cancer Therapy by Sequencing of Plasma DNA", Nature (doi:10.1038/nature12065), (2013),6 pgs.

Myers, et al., "Accurate Detection of Aneuploidies in Array CGH and Gene Expression Microarray Data", Bioinformatics, vol. 20, No. 18, (2004),3533-3543.

Nannya, et al., "A Robust Algorithm for Copy Number Detection Using High-density Oligonucleotide Single Nucleotide Polymorphism Genotyping Arrays", Cancer Res., 65, (Jul. 15, 2005),6071-6079.

Nicolaides, et al., "Noninvasive Prenatal Testing for Fetal Trisomies in a Routinely Screened First-Trimester Population", American Journal of Obstetrics (article in press), 207, (2012),1.e1-1.e6.

Nicolaides, et al., "Prenatal Detection of Fetal Triploidy from Cell-Free DNA Testing in Maternal Blood", Fetal Diagnosis and Therapy, (Oct. 10, 2013),1-6.

Nicolaides, et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, (Apr. 26, 2013),575-579.

Ogino, et al., "Bayesian Analysis and Risk Assessment in Genetic Counseling and Testing", Journal of Molecular Diagnostics, vol. 6, No. 1, (Feb. 2004),9 pgs.

Orozco, et al., "Placental Release of Distinct DNA-Associated Micro-Particles into Maternal Circulation: Reflective of Gestation Time and Preeclampsia", Placenta, 30, (2009),891-897.

(56) References Cited

OTHER PUBLICATIONS

Ozawa, et al., "Two Families with Fukuyama Congenital Muscular Dystrophy that Underwent in Utero Diagnosis Based on Polymorphism Analysis", Clinical Muscular Dystrophy: Research in Immunology and Genetic Counseling—FY 1994 Research Report (including text in Japanese), (1994),8 pgs.
Paez, et al., "Genome coverage and sequence fidelity of Φ29 polymerase-based multiple strand displacement whole genome amplification", Nucleic Acids Research, vol. 32, No. 9, (May 18, 2004),1-11.
Page, et al., "Chromosome Choreography: The Meiotic Ballet", Science, vol. 301, (Aug. 8, 2003),785-789.
Palomaki, et al., "DNA Sequencing of Maternal Plasma Reliably Identifies Trisomy 18 and Trisomy 13 as Well as Down Syndrome: an International Collaborative Study", Genetics in Medicine, (2012),10 pgs.
Palomaki, et al., "DNA Sequencing of Maternal Plasma to Detect Down Syndrome: An International Clinical Validation Study", Genetics in Medicine (pre-print version), vol. 13, (2011),8 pgs.
Papageorgiou, et al., "Fetal-Specific DNA Methylation Ratio Permits Noninvasive Prenatal Diagnosis of Trisomy 21", Nature Medicine (advance online publication), 17, (Mar. 6, 2011),5 pgs.
Pena, et al., "Paternity Testing in the DNA Era", Trends in Genetics, vol. 10, No. 6, (Jun. 1994),204-209.
Perkel, "Overcoming the Challenges of Multiplex PCR", Biocompare Editorial Article, Oct. 23, 2012, 1-5.
Perry, et al., "The Fine-Scale and Complex Architecture of Human Copy-Number Variation", The American Journal of Human Genetics, 82, (Mar. 2008),685-695.
Pertl, et al., "Detection of Male and Female Fetal DNA in Maternal Plasma by Multiplex Fluorescent Polymerase Chain Reaction Amplification of Short Tandem Repeats", Hum. Genet., 106, (2000),45-49.
Peters, et al., "Noninvasive Prenatal Diagnosis of a Fetal Microdeletion Syndrome", New England Journal of Medicine, vol. 365, No. 19, (Nov. 10, 2011),1847-1848.
Pfaffl, "Relative Expression Software Tool (REST ©) for Group-Wise Comparison and Statistical Analysis of Relative Expression Results in real-Time PCR", Nucleic Acids Research, vol. 30, No. 9, e36, (2002),10 pgs.
Phillips, et al., "Resolving Relationship Tests that Show Ambiguous STR Results Using Autosomal SNPs as Supplementary Markers", Forensic Science International: Genetics 2, (2008),198-204.
Porreca, et al., "Multiplex Amplification of Large Sets of Human Exons", Nature Methods (advance online publication), 4, (Oct. 14, 2007),6 pgs.
Rabinowitz, et al., "Accurate Prediction of HIV-1 Drug Response from the Reverse Transcriptase and Protease Amino Acid Sequences Using Sparse Models Created by Convex Optimization", Bioinformatics, vol. 22, No. 5, (2006),541-549.
Rabinowitz, et al., "Non-Invasive Prenatal Aneuploidy Testing of Chromosomes 13, 18, 21, X, and Y Using Targeted Sequencing of Polymorphic Loci", The American Society of Human Genetics, meeting poster, (2012).
Rabinowitz, et al., "Origins and Rates of Aneuploidy in Human Blastomeres", Fertility and Sterility, vol. 97, No. 2, (Feb. 2012),395-401.
Rahmann, et al., "Mean and Variance of the Gibbs Free Energy of Oligonucleotides in the Nearest neighbor Model Under Varying Conditions", Bioinformatics, vol. 20, No. 17, (2004),2928-2933.
Rava, et al., "Circulating Fetal Cell-Free DNA Fraction Differ in Autosomal Aneuploidies and Monosomy X", Clinical Chemistry (papers in press), vol. 60, No. 1, (Sep. 17, 2013),8 pgs.
Rechitsky, et al., "Preimplantation Genetic Diagnosis with HLA Matching", Reproductive BioMedicine Online, vol. 9, No. 2, (2004),210-221.
Renwick, et al., "Proof of Principle and First Cases Using Preimplantation Genetic Haplotyping—A Paradigm Shift for Embryo Diagnosis", Reproductive BioMedicine Online, vol. 13, No. 1, (2006),110-119.
Roper, et al., "Forensic Aspects of DNA-Based Human Identity Testing", Journal of Forensic Nursing, 4, (2008),150-156.
Roux, "Optimization and Troubleshooting in PCR", PCR Methods Appl. vol. 4, (1995), 185-194.
Rozen, et al., "Primer3 on the WWW for General Users and for Biologist Programmers", Methods in Molecular Biology, vol. 132: Bioinformatics Methods and Protocols, (1999),365-386.
Russell, et al., "X Chromosome Loss and Ageing", Cytogenet Genome Res, vol. 116, (2007),181-185.
Ryan, et al., "Informatics-Based, Highly Accurate, Noninvasive Prenatal Paternity Testing", Genetics in Medicine (advance online publication), (Dec. 20, 2012),5 pgs.
Samango-Sprouse, et al., "SNP-Based Non-Invasive Prenatal Testing Detects Sex Chromosome Aneuploides with High Accuracy", Prenatal Diagnosis, vol. 33, (2013),1-7.
Sander, et al., "Genetic Medicine and the Future of Health Care", Science, vol. 287, (3/17/200),1977-1978.
Santalucia, Jr., et al., "Improved Nearest-Neighbor Parameters for Predicting DNA Duplex Stability", Biochemistry, 35, (1996),3555-3562.
Santalucia, Jr., et al., "The Thermodynamics of DNA Structural Motifs", Annu. Rev. Biophys. Biomol. Struct., 33, (2004),415-440.
Sebat, et al., "Strong Association of De Novo Copy Number Mutations with Autism", Science, vol. 316, (Apr. 20, 2007),445-449.
Sehnert, et al., "Optimal Detection of Fetal Chromosomal Abnormalities by Massively Parallel DNA Sequencing of Cell-Free Fetal DNA from Maternal Blood", Clinical Chemistry (papers in press), vol. 57, No. 7, (2011),8 pgs.
Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, (2004),241-248.
Simpson, et al., "Fetal Cells in Maternal Blood: Overview and Historical Perspective", Annals New York Academy of Sciences, 731, (1994),1-8.
Slater, et al., "High-Resolution Identification of Chromosomal Abnormalities Using Oligonucleotide Arrays Containing 116,204 SNPs", Am. J. Hum. Genet., vol. 77, No. 5, (2005),709-726.
Sint, "Advances in Multiplex PCR: Balancing Primer Efficiencies and Improving Detection Success", Methods in Ecology and Evolution vol. 3, (2012), 898-905.
Snijders, et al., "Assembly of Microarrays for Genome-Wide Measurement of DNA Copy Number", Nature Genetics vol. 29, (Nov. 2001),263-264.
Sparks, et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology, 206, (Apr. 2012),319.e1-319.e9.
Sparks, et al., "Selective Analysis of Cell-Free DNA in Maternal Blood for Evaluation of Fetal Trisomy", Prenatal Diagnosis, 32, (2012),1-7.
Spits, et al., "Optimization and Evaluation of Single-Cell Whole Genome Multiple Displacement Amplification", Human Mutation, vol. 27, No. 5, (2006),496-503.
Stephens, et al., "A Comparison of Bayesian Methods for Haplotype Reconstruction from Population Genotype Data", Am. J. Hum. Genet., 73, (2003),1162-1169.
Stevens, et al., "Ontology-Based Knowledge Representation for Bioinformatics", Briefings in Bioinformatics, vol. 1, No. 4, (Nov. 2000),398-414.
Steyerberg, et al., "Application of Shrinkage Techniques in Logistic Regression Analysis: A Case Study", Statistica Neerlandica, vol. 55, No. 1, (2001),76-88.
Strom, et al., "Neonatal Outcome of Preimplantation Genetic Diagnosis by Polar Body Removal: The First 109 Infants", Pediatrics, vol. 106, No. 4, (Oct. 4, 2000),650-653.
Strom, et al., "Three births after preimplantation genetic diagnosis for cystic fibrosis with sequential first and second polar body analysis", American Journal of Obstetrics and Gynecology, vol. 178, No. 6, (1998),1298-1306.

(56) References Cited

OTHER PUBLICATIONS

Stroun, et al., "Prehistory of the Notion of Circulating Nucleic Acids in Plasma/Serum (CNAPS): Birth of a Hypothesis", Ann. N.Y. Acad. Sci., 1075, (2006),10-20.
Sweetkind-Singer, et al., "Log-Penalized Linear Regression", International Symposium on Information Theory, Yokahama, Japan, (Jun. 29, 2013-Jul. 4, 2003),p. 286.
Tang, et al., "Detection of Fetal-Derived Paternally Inherited X-Chromosome Polymorphisms in Maternal Plasma", Clinical Chemistry vol. 45, No. 11, (1999),2033-2035.
Thomas, et al., "The Time of Appearance and Disappearance of Fetal DNA from the Maternal Circulation", Prenatal Diagnosis, vol. 15, (1995),641-646.
Tong, "Noninvasive Prenatal Detection of Fetal Trisomy 18 by Epigenetic Allelic Ratio Analysis in Maternal Plasma: Theoretical and Empirical Considerations", Clinical Chemistry vol. 52, No. 12, (2006),2194-2202.
Tong, et al., "Noninvasive Prenatal Detection of Trisomy 21 by an Epigenetic-Genetic Chromosome-Dosage Approach", Clinical Chemistry, vol. 56, No. 1, (2010),90-98.
Troyanskaya, et al., "A Bayesian Framework for Combining Heterogeneous Data Sources for Gene Function Prediction (in Saccharomyces cerevisiae)", PNAS, vol. 100, No. 14, (Jul. 8, 2003),8348-8353.
Tsui, et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, (2009),1031-1037.
Turner, et al., "Massively Parallel Exon Capture and Library-Free Resequencing Across 16 Genomes", Nature Methods, vol. 6, No. 5, (May 2009),315-316.
U.S. Appl. No. 11/004,274, Office Action mailed Nov. 24, 2009, 31 pgs.
U.S. Appl. No. 11/004,274, Office Action mailed Feb. 4, 2009, 26 pgs.
U.S. Appl. No. 11/004,274, Office Action mailed Mar. 2, 2011, 50 pgs.
U.S. Appl. No. 11/004,274, Office Action mailed May 13, 2008, 25 pgs.
U.S. Appl. No. 11/496,982, Office Action mailed Jan. 21, 2011, 25 pgs.
U.S. Appl. No. 11/496,982, Office Action mailed May 27, 2010, 8 pgs.
U.S. Appl. No. 11/603,406, Office Action mailed Feb. 18, 2011, 26 pgs.
U.S. Appl. No. 11/603,406, Office Action mailed Mar. 14, 2013, 15 pgs.
U.S. Appl. No. 11/603,406, Office Action mailed Aug. 19, 2010, 20 pgs.
U.S. Appl. No. 11/634,550, Office Action mailed Jan. 24, 2011, 13 pgs.
U.S. Appl. No. 11/634,550, Office Action mailed Aug. 4, 2010, 7 pgs.
U.S. Appl. No. 12/076,348, Office Action mailed Feb. 8, 2013, 9 pgs.
U.S. Appl. No. 12/076,348, Office Action mailed Mar. 4, 2011, 26 pgs.
U.S. Appl. No. 12/076,348, Office Action mailed Aug. 20, 2010, 22 pgs.
U.S. Appl. No. 13/683,604, Office Action mailed Nov. 22, 2013, 81pages.
Vallone, et al., "AutoDimer: a Screening Tool for Primer-Dimer and Hairpin Structures", BioTechniques, vol. 37, (Aug. 2004),226-231.
Verlinsky, et al., "Over a Decade of Experience with Preimplantation Genetic Diagnosis", Fertility and Sterility, vol. 82, No. 2, (Aug. 2004),302-303.
Wagner, et al., "Non-Invasive Prenatal Paternity Testing from Maternal Blood", Int. J. Legal Med., 123, (2009),75-79.
Wang, et al., "A Genotyping System Capable of Simultaneously Analyzing >1000 Single Nucleotide Polymorphisms in a Haploid Genome", Genome Res., vol. 15, 2005, 276-283.
Wang, et al., "Gestational Age and Maternal Weight Effects on Fetal Cell-Free DNA in Maternal Plasma", Prenatal Diagnosis, vol. 33, (2013),662-666.
Wapner, et al., "Chromosomal Microarray Versus Karyotyping for Prenatal Diagnosis", The New England Journal of Medicine, vol. 367, No. 23, (Dec. 6, 2012),2175-2184.
Watkins, Jr., et al., "Thermodynamic contributions of single internal rA •dA, rC • dC, rG • dG and rU • dT mismatches in RNA/DNA duplexes", Nucleic Acids Research, vol. 39, No. 5, (Nov. 10, 2010),1894-1902.
Wells, "Advances in Preimplantation Genetic Diagnosis", European Journal of Obstetrics and Gynecology and Reproductive Biology, 115S, (2004),597-5101.
Wells, "Microarray for Analysis and Diagnosis of Human Embryos", 12th International Congress on Prenatal Diagnosis and Therapy, Budapest, Hungary, (Jun. 24-27, 2004),9-17.
Wen, "Universal Multiples PCR: A Novel Method of Simultaneous Amplification of Multiple DNA Fragments", Plant Methods vol. 8, No. 32, (2012), 1-9.
Wilton, "Preimplantation Genetic Diagnosis and Chromosome Analysis of Blastomeres Using Comparative Genomic Hybridization", Human Reproduction Update, vol. 11, No. 1, (2005),33-41.
Wilton, et al., "Birth of a Healthy Infant After Preimplantation Confirmation of Euploidy by Comparative Genomic Hybridization", N. Engl. J. Med., vol. 345, No. 21, (Nov. 22, 2001),1537-1541.
Xia, et al., "Thermodynamic Parameters for an Expanded Nearest-Neighbor Model for Formation of RNA Duplexes with Watson-Crick Base Pairs", Biochemistry, 37, (1998),14719-14735.
Yeh, et al., "Knowledge Acquisition, Consistency Checking and Concurrency Control for Gene Ontology (GO)", Bioinformatics, vol. 19, No. 2, (2003),241-248.
Zhang, "Quantifying RNA Allelic Ratios by Microfluidic Multiplex PCR and Sequencing", Nature Methods, vol. 11, No. 1, Jan. 2014, 51-56.
Zhao, et al., "An Integrated View of Copy Number And Allelic Alterations in the Cancer Genome Using Single Nucleotide Polymorphism Arrays", Cancer Research, 64, (May 1, 2004),3060-3071.
Zhou, et al., "Counting Alleles Reveals a Connection Between Chromosome 18q Loss and Vascular Invasion", Nature Biotechnology, vol. 19, (Jan. 2001),78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, (2012),1-9.
www.fatsecret.com (printed from internet Nov. 1, 2014).
Bentley, David R, et al., "Accurate Whole Human Genome Sequencing Using Reversible Terminator Chemistry", Nature. Nov. 6, 2008; 456(7218): 53-59.
Bianchi, et al., Fetal gender and aneuploidy detection using fetal cells maternal blood: analysis of NIFTY I data, Prenat Diagn 2002; 22: 609-615.
Cross, et al., "Resolution of trisomic mosaicism in prenatal diagnosis: estimated performance of a SOK SNP microarray" Prenat Diagn 2007; 27: 1197-1204.
Ding, C, et al., "Direct molecular haplotyping of long-range genomic DNA with M1-PCR", PNAS 100(13), (2003), 7449-7453.
Handyside et al. (Molecular Human Reproduction, 2004, 10(10), 767-772.
Harismendy, O, et al. "Method for Improving Sequence Coverage Uniformity of Targeted Genomic Intervals Amplified by LR-PCR Using Illumina GA Sequencing-By-Synthesis Technology", Bio Techniques, 46(3), (2009) 229-231.
International Application Serial No. PCT/US14/51926, International Search Report and Written Opinion mailed Dec. 9, 2014, 5 pgs.
Paired-End Sample Preparation Guide, Illumina Catalog# E-930-1 001, Part# 1005063 Rev. E, (2009) 1-40.
Price, T.S. "SW-ARRAY: a dynamic programming solution for the identification of copy-Number changes in genomic DNA using array comparative genome hybridization data", Nucleic Acids Research, vol. 33, No. 11, Jun. 16, 2005, pp. 3455-3464.
Rychlik, et al."Optimization of the annealing temperature for DNA amplification in vitro" (1990) 6409-6412.

(56) References Cited

OTHER PUBLICATIONS

Sun, Guihua, et al., "SNPs in human miRNA genes affect biogenesis and function" RNA, 15(9), (2009) 1640-1651.
Varley, Katherine Elena, et al., "Nested Patch PCR Enables Highly Multiplexed Mutation Discovery in Candidate Genes" Genome Res., 18(11) (2008) 1844-1850.
"European Application No. 014198110, European Search Report Mailed Apr. 28, 2015, 3 pages."
"Guideline related to genetic examination", Societies Related to Genetic Medicine, Japanese Society for Genetic Counseling, Japanese Society for Gene Diagnosis and Therapy, Japan Society of Obstetrics an, 2003, 2-15.
Ellison, Aaron M., "Bayesian Inference in Ecology", Ecology Letters, 2004, vol. 7, p. 509-520.
Fredriksson, et al., "Multiplex amplification of all coding sequences within 10 cancer genes by Gene-Collector", Nucleic Acids Research, 2007, vol. 35, No. 7 e47, 1-6.
Holleley, et al., "Multiplex Manager 1.0: a Cross-Platform Computer Program that Plans and Optimizes Multiplex PCR", BioTechniques46:511-517 (Jun. 2009), 511-517.
Hospital, F et al., "A General Algorithm to Compute Mul Ti Locus Genotype Frequencies Under Various Mating Systems", Cabios Computer Applications in the Biosciences, vol. 12, No. 6, Jan. 1, 1996, pp. 455-462.
Krjutskov, K et al., "Development of a single tube 640-plex genotyping method for detection of nucleic acid variations on microarrays", Nucleic Acids Research, vol. 36, No. 12, May 23, 2008, pp. e75-e75.
Markoulatos, P et al., "Multiplex Polymerase Chain Reaction: A Practical Approach", 2002 Wiley-Liss, Inc. DOI 10.1002/jcla.2058 Journal of Clinical Laboratory Analysis 16:47-51 (2002).
Sasabe, Yutaka, "Genetic Diagnosis of Gametes and Embryos Resulting from ART", Japanese Journal of Fertility and Sterility, 2001, vol. 46, No. 1, p. 43-46.
Servin, B et al., "MOM: AProgram to Compute Fully Informative Genotype Frequencies in Complex Breeding Schemes", Journal of Heredity, vol. 93, No. 3, Jan. 1, 2002, pp. 227-228.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011, pp. 6549-6554.
Shen, Zhiyong, "MPprimer: a program for reliable multiplex PCR primer design", BMC Bioinformatics 2010, 11:143, 1-7.
Su, S.Y. et al., ""Inferring combined CNV/SNP haplotypes from genotype data"", Bioinformatics, vol. 26, No. 11,1, Jun. 1, 2010, 1437-1445.
Tang, et al., Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.
You, Frank M. et al., "BatchPrimer3: A high throughput web application for PCR and sequencing primer design", BMC Bioinformatics, Biomed Central, London, GB, vol. 9, No. 1, May 29, 2008, p. 253.
Blast of AAAAAAAAATTTAAAAAAAAATTT(http://blast.ncbi.nlm.nih.gov/Blast.cgi, downloaded May 4, 2015).
db SNP rs2056688 (http://www.ncbi.nlm.nih.gov/projects/SNP/snp_ref.cgi?rs=2056688, downloaded May 4, 2015.
Declaration by Dr. Zimmerman of Oct. 30, 2014 filed in U.S. Appl. No. 14/044,434.
Merriam-Webster.com (http://www.merriam-webster.com/dictionary/universal, downloaded Jul. 23, 2014).
European Application No. 014198110, European Search Report Mailed Apr. 28, 2015, 3 pages.
Fan, et al., "Whole-genome molecular haplotyping of single cells", Nature Biotechnology, vol. 29, No. 1, Jan. 1, 2011, 51-57.
Howie, et al., "Fast and accurate genotype imputation in genome-wide association studies through pre-phasing", Nature Genetics, voi. 44, No. 8, Jul. 22, 2012, 955-959.
Ryan, et al., "The importance of phase information for human genomics", Nature Reviews Genetics, voi. 12, No. 3, Mar. 1, 2011.
Su, S.Y. et al., "Inferring combined CNV/SNP haplotypes from genotype data", Bioinformatics, vol. 26, No. 11,1, Jun. 1, 2010, 1437-1445.
Chiu, Rossa W.K., "Effects of Blood-Processing Protocols on Fetal and Total DNA Quantification in Maternal Plasma", Clinical Chemistry, 47(9), (Jan. 1, 2001), 1607-1613.
De Vries et al., "Diagnostic genome profiling in mental retardation", Am J Hum Genet, 77, p. 606-616, published online Aug. 30, 2005.
Donohoe G, et al., "Rapid Single-Tube Screening of the C282Y Hemochromatosis Mutation by Real-Time Multiplex Allele-specific PCR without Fluorescent Probes", Clinical Chemistry, 2000, 46: 1540-1547.
Hardenbol, et al., "Highly multiplexed molecular inversion probe genotyping: Over 10,000 targeted SNP's genotyped in a singled tube assay", Genome Research, 15, (Jan. 1, 2005), 269-275.
How Many Carbs in a Potato?, [Online]. Retrieved from the Internet<http.//www.healthguide.org/How-Many-Carbs-In-A-Potato.html>, (Nov. 1, 2014), 3 pgs.
Liew et al. Clinical Chemistry, 2004, 50(7), 1156-1164.
Podder et al. (BMC Med Genom, 2008, vol. 1, No. 5, p. 1 of 15).
Renwick, et al., "Proof of Principle and First Cases Using Preimplantation Genetic Haplotyping —A Paradigm Shift for Embryo Diagnosis", Reproductive BioMedicine Online, vol. 13, No. 1, (2006), 110-119.
Ricciotti Hope, "Eating by Trimester", [Online]. Retrieved from Internet <http://www.youandyourfamily.com/article.php?story=Eating+by+Trimester>, (Oct. 7, 2014), 3 pgs.
Schoumans et al., "Detection of chromosomal imbalances in children with idiopathic mental retardation by array based comparative genomic hybridisation (array-CGH)", JMed Genet, 42, pp. 699-705, Sep. 2005.
Sherlock, et al., "Assessment of Diagnostic Quantitative Fluorescent Multiplex Polymerase Chain Reaction Assays Performed on Single Cells,"Annals of Human Genetics, 1998, vol. 62(1), pp. 9-23.
Wagner, Jasenka et al. "Non-invasive prenatal paternity testing from maternal blood", International Journal of Legal Medicine, Springer, Berlin, DE, vol. 123, No. 1, Oct. 24, 2008, pp. 75-79.
Wang, et al. Yuker, "Allele quantification using molecular inversion probes (MIP)", Nucleic Acids Research, vol. 33, No. 21, (Nov. 28, 2005), 14 pgs.
Wells Dagan, "Detailed Chromosomal and Molecular Genetic Analysis of Single Cells by Whole Genome Amplification and Comparative Genomic Hybridisation", Nucleic Acids Research, 1999, vol. 27, No. 4, 1214-1218.

METHODS FOR NON-INVASIVE PRENATAL PLOIDY CALLING

RELATED APPLICATIONS

This application is a continuation of U.S. Utility application Ser. No. 14/179,399, filed Feb. 12, 2104; U.S. Utility application Ser. No. 14/100,928, filed Dec. 9, 2013; and U.S. Utility application Ser. No. 13/110,685, filed May 18, 2011. Utility application Ser. No. 14/179,399 and U.S. Utility application Ser. No. 14/100,928 are both a continuation of U.S. Utility application Ser. No. 13/110,685. U.S. Utility application Ser. No. 13/110,685 claims the benefit of and priority to U.S. Provisional Application Ser. No. 61/395,850, filed May 18, 2010; U.S. Provisional Application Ser. No. 61/398,159, filed Jun. 21, 2010; U.S. Provisional Application Ser. No. 61/462,972, filed Feb. 9, 2011; U.S. Provisional Application Ser. No. 61/448,547, filed Mar. 2, 2011; and U.S. Provisional Application Ser. No. 61/516,996, filed Apr. 12, 2011; the entirety of these applications are hereby incorporated herein by reference for the teachings therein.

FIELD

The present disclosure relates generally to methods for non-invasive prenatal ploidy calling.

BACKGROUND

Current methods of prenatal diagnosis can alert physicians and parents to abnormalities in growing fetuses. Without prenatal diagnosis, one in 50 babies is born with serious physical or mental handicap, and as many as one in 30 will have some form of congenital malformation. Unfortunately, standard methods have either poor accuracy, or involve an invasive procedure that carries a risk of miscarriage. Methods based on maternal blood hormone levels or ultrasound measurements are non-invasive, however, they also have low accuracies. Methods such as amniocentesis, chorion villus biopsy and fetal blood sampling have high accuracy, but are invasive and carry significant risks. Amniocentesis was performed in approximately 3% of all pregnancies in the US, though its frequency of use has been decreasing over the past decade and a half.

It has recently been discovered that cell-free fetal DNA and intact fetal cells can enter maternal blood circulation. Consequently, analysis of these cells can allow early Non-Invasive Prenatal Genetic Diagnosis (NPD).

Normal humans have two sets of 23 chromosomes in every diploid cell, with one copy coming from each parent. Aneuploidy, a condition in a nuclear cell where the cell contains too many and/or too few chromosomes is believed to be responsible for a large percentage of failed implantations, miscarriages, and genetic diseases. Detection of chromosomal abnormalities can identify individuals or embryos with conditions such as Down syndrome, Klinefelter's syndrome, and Turner syndrome, among others, in addition to increasing the chances of a successful pregnancy. Testing for chromosomal abnormalities is especially important as the mother's age: between the ages of 35 and 40 it is estimated that at least 40% of the embryos are abnormal, and above the age of 40, more than half of the embryos are abnormal.
Some Tests Used for Prenatal Screening Low levels of pregnancy-associated plasma protein A (PAPP-A) as measured in maternal serum during the first trimester may be associated with fetal chromosomal anomalies including trisomies 13, 18, and 21. In addition, low PAPP-A levels in the first trimester may predict an adverse pregnancy outcome, including a small for gestational age (SGA) baby or stillbirth. Pregnant women often undergo the first trimester serum screen, which commonly involves testing women for blood levels of the hormones PAPP-A and beta human chorionic gonadotropin (beta-hCG). In some cases women are also given an ultrasound to look for possible physiological defects. In particular, the nuchal translucency (NT) measurement can indicate risk of aneuploidy in a fetus. In many areas, the standard of treatment for prenatal screening includes the first trimester serum screen combined with an NT test.

The triple test, also called triple screen, the Kettering test or the Bart's test, is an investigation performed during pregnancy in the second trimester to classify a patient as either high-risk or low-risk for chromosomal abnormalities (and neural tube defects). The term "multiple-marker screening test" is sometimes used instead. The term "triple test" can encompass the terms "double test," "quadruple test," "quad test" and "penta test."

The triple test measures serum levels of alpha-fetoprotein (AFP), unconjugated estriol ($UE_3$), beta human chorionic gonadotropin (beta-hCG), Invasive Trophoblast Antigen (ITA) and/or inhibin. A positive test means having a high risk of chromosomal abnormalities (and neural tube defects), and such patients are then referred for more sensitive and specific procedures to receive a definitive diagnosis, mostly invasive procedures like amniocentesis. The triple test can be used to screen for a number of conditions, including trisomy 21 (Down syndrome). In addition to Down syndrome, the triple and quadruple tests screen for fetal trisomy 18 also known as Edward's syndrome, open neural tube defects, and may also detect an increased risk of Turner syndrome, triploidy, trisomy 16 mosaicism, fetal death, Smith-Lemli-Opitz syndrome, and steroid sulfatase deficiency.

SUMMARY

Methods for non-invasive prenatal ploidy calling are disclosed herein. In an embodiment of the present disclosure, methods are disclosed for determining a ploidy status of a chromosome in a gestating fetus, the method comprising obtaining a first sample that contains DNA from the mother of the fetus and DNA from the fetus; obtaining genotypic data from one or both parents of the fetus; processing the first sample by purifying the DNA so as to obtain a second sample; measuring the DNA in the second sample at a set of polymorphic alleles; calculating, on a computer, allele ratios at the set of polymorphic alleles from the DNA measurements made on the second sample; creating, on a computer, a plurality of ploidy hypotheses concerning expected allele ratios at the set of polymorphic alleles on the chromosome for different possible ploidy states of the chromosome; building, on a computer, a joint distribution model for heterozygosity rates of each polymorphic allele on the chromosome for each ploidy hypothesis using genotypic data from the one or both parents of the fetus; determining, on a computer, a relative probability of each of the ploidy hypotheses using the joint distribution model and the allele ratios calculated for the second sample; and calling the ploidy state of the fetus by selecting the ploidy state corresponding to the hypothesis with the greatest probability. In an embodiment of the present disclosure, the first sample has been isolated from maternal blood. In an embodiment of the present disclosure, the step of processing the first sample further comprises amplifying the DNA.

In an embodiment of the present disclosure, the step of processing the first sample further comprises preferentially enriching the DNA at the plurality of polymorphic loci. In an embodiment of the present disclosure, the preferentially enriching the DNA at a plurality of polymorphic loci comprises obtaining a pre-circularized probe such that the 3' and 5' ends are designed to hybridize to a region of DNA that is separated from the polymorphic region of the allele by a small number of bases, where the small number is 1, 2, 3, 4, 5, 6, 7, 8, 9, 10, 11, 12, 13, 14, 15, 16, 17, 18, 19, or 20, or a combination thereof; hybridizing the pre-circularized probe to purified DNA from the first sample; circularizing the pre-circularized probe; and amplifying some or all of the circularized probe. In an embodiment of the present disclosure, the preferentially enriching the DNA at a plurality of polymorphic loci comprises obtaining a forward probe such that the 3' end of the forward probe is designed to hybridize to the region of DNA immediately upstream from the polymorphic region, and separated from the polymorphic region by a small number of bases, where the small number is selected from the group consisting of 1, 2, 3, 4, 5, 6 to 10, and 11 to 20; obtaining a reverse probe such that the 3' end of the reverse probe is designed to hybridize to the region of DNA immediately downstream from the polymorphic region, and separated from the polymorphic region by a small number of bases, where the small number is selected from the group consisting of 1, 2, 3, 4, 5, 6 to 10, and 11 to 20; hybridizing the two probes to DNA in the first sample of DNA; and amplifying the DNA using the polymerase chain reaction. In an embodiment of the present disclosure, the preferentially enriching the DNA at a plurality of polymorphic loci comprises obtaining a set of hybrid capture probes; hybridizing the hybrid capture probes to the DNA in the first sample; and physically separating the hybridized DNA from the first sample of DNA from the unhybridized DNA from the first sample. In an embodiment of the present disclosure, the set of hybrid capture probes are designed to hybridize to a region that is flanking but not crossing the polymorphic allele. In an embodiment of the present disclosure, the set of hybrid capture probes are designed to hybridize to a region that is flanking but not crossing the polymorphic allele, and wherein the length of the flanking capture probe may be selected from the group consisting of as low as about 120 bases, as low as about 110 bases, as low as about 100 bases, as low as about 90 bases, as low as about 80 bases, as low as about 70 bases, as low as about 60 bases, as low as about 50 bases, as low as about 40 bases, as low as about 30 bases, and as low as about 25 bases. In an embodiment of the present disclosure, the preferential enrichment results in average degree of allelic bias between the second sample and the first sample of a factor selected from the group consisting of no more than a factor of 2, no more than a factor of 1.5, no more than a factor of 1.2, no more than a factor of 1.1, no more than a factor of 1.05, no more than a factor of 1.02, no more than a factor of 1.01, no more than a factor of 1.005, no more than a factor of 1.002, no more than a factor of 1.001 and no more than a factor of 1.0001.

In an embodiment of the present disclosure, the set of polymorphic alleles are SNPs. In an embodiment of the present disclosure, the step of measuring the DNA in the second sample is done by sequencing.

In an embodiment of the present disclosure, the method is executed for a plurality of gestating fetuses, the method further comprising determining the percent of DNA that is fetal in each of the second fractions; and wherein the step of measuring the DNA in the second sample is done by sequencing a number of DNA molecules in each of the second samples, where more molecules of DNA are sequenced from those second samples that have a smaller fraction of fetal DNA than those second samples that have a larger fraction of fetal DNA. In an embodiment of the present disclosure, the method is executed for a plurality of gestating fetuses, and where the measuring the DNA in the second sample is done, for each of the fetuses, by sequencing a fraction of the second sample of DNA to give a first set of measurements, the method further comprising making a first relative probability determination for each of the ploidy hypotheses for each of the fetuses, given the first set of DNA measurements; resequencing a second fraction of the second sample from those fetuses where the first relative probability determination for each of the ploidy hypotheses indicates that a ploidy hypothesis corresponding to an aneuploid fetus has a significant probability, to give a second set of measurements; making a second relative probability determination for ploidy hypotheses for the fetuses using the second set of measurements and optionally also the first set of measurements; and calling the ploidy states of the fetuses whose second sample was resequenced by selecting the ploidy state corresponding to the hypothesis with the greatest probability as determined by the second relative probability determination.

In an embodiment of the present disclosure, the step of building a joint distribution model is done by using data about the probability of chromosomes crossing over at different crossover locations in a chromosome to model dependence between polymorphic alleles on the chromosome. In an embodiment of the present disclosure, the step of building a joint distribution model and the step of determining the relative probability of each hypothesis are done using a method that does not require the use of a reference chromosome.

In an embodiment of the present disclosure, the step of determining the relative probability of each hypothesis makes use of an estimated fraction of fetal DNA in the measured sample. In an embodiment of the present disclosure, the DNA measurements from the second sample used in calculating allele ratios and determining the relative probability of each hypothesis comprise primary genetic data.

In an embodiment of the present disclosure, selecting the ploidy state corresponding to the hypothesis with the greatest probability is carried out using maximum likelihood estimates. In an embodiment of the present disclosure, the step of calling the ploidy state of the fetus further comprises combining the relative probabilities of each of the ploidy hypotheses determined using the joint distribution model and the allele ratios with relative probabilities of each of the ploidy hypotheses that are calculated using statistical techniques taken from a group consisting of a read count analysis, comparing heterozygosity rates, a statistic that is only available when parental genetic information is used, the probability of normalized genotype signals for certain parent contexts, a statistic that is calculated using an estimated fetal fraction of the first or second mixture, and combinations thereof.

In an embodiment of the present disclosure, a confidence estimate is calculated for the called ploidy state. In an embodiment of the present disclosure, the method further comprises producing a report stating the called ploidy state of the fetus. In an embodiment of the present disclosure, the method further comprises taking a clinical action based on the called ploidy state of the fetus, wherein the clinical action is selected from one of terminating the pregnancy or maintaining the pregnancy. In an embodiment of the present disclosure, the method can be performed at between 4 and 5 weeks gestation; between 5 and 6 weeks gestation; between 6 and 7 weeks gestation; between 7 and 8 weeks gestation; between 8 and 9 weeks gestation; between 9 and 10 weeks gestation; between 10 and 12 weeks gestation; between 12 and 14 weeks gestation; between 14 and 20 weeks gestation; between 20 and 40 weeks gestation; in the first trimester; in the second trimester; or in the third trimester.

In an embodiment of the present disclosure, a composition is described comprising a sample of preferentially enriched DNA, wherein the sample of preferentially enriched DNA has been preferentially enriched at a plurality of polymorphic loci from a first sample of DNA, wherein the degree of enrichment is selected from the group consisting of at least 10, at least 100, at least 1,000, at least 10,000, at least 100,000, or at least 1,000,000, and wherein the allelic bias between the first sample and the preferentially enriched sample is, on average, selected from the group consisting of less than 1000%, less than 500%, less than 200%, less than 100%, less than 50%, less than 20%, less than 10%, less than 5%, less than 2%, less than 1%, less than 0.5%, less than 0.2%, less than 0.1%, less than 0.05%, less than 0.02%, and less than 0.01%. In an embodiment of the present disclosure, a method is to create such a sample of preferentially enriched DNA.

In an embodiment of the present disclosure, methods are disclosed for determining a fetal aneuploidy by determining the number of copies of maternal and fetal target chromosomes, having target sequences in a mixture of maternal and fetal genetic material, comprising the steps of (a) obtaining maternal tissue containing both maternal and fetal genetic material; (b) obtaining a mixture of maternal and fetal genetic material from said maternal tissue; (c) distributing the genetic material obtained in step b) into a plurality of reaction samples, to randomly provide individual reaction samples that contain a target sequence from a target chromosome and individual reaction samples that do not contain a target sequence from a target chromosome; (d) analyzing the target sequences of genetic material present or absent in said individual reaction samples to provide a first number of binary results representing presence or absence of a presumably euploid fetal chromosome in the reaction samples and a second number of binary results representing presence or absence of a possibly aneuploid fetal chromosome in the reaction samples; (e) calculating an expected distribution of a number of binary results for a presumably euploid fetal chromosome in the reaction samples using the first number; (f) calculating an expected distribution of a number of binary results for a presumably aneuploid fetal chromosome in the reaction samples using the first number and an estimated fraction of fetal DNA found in the mixture of step (b); and (g) using a maximum likelihood approach to determine whether the second number indicates the presence of a fetal aneuploidy.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

Figure 1:
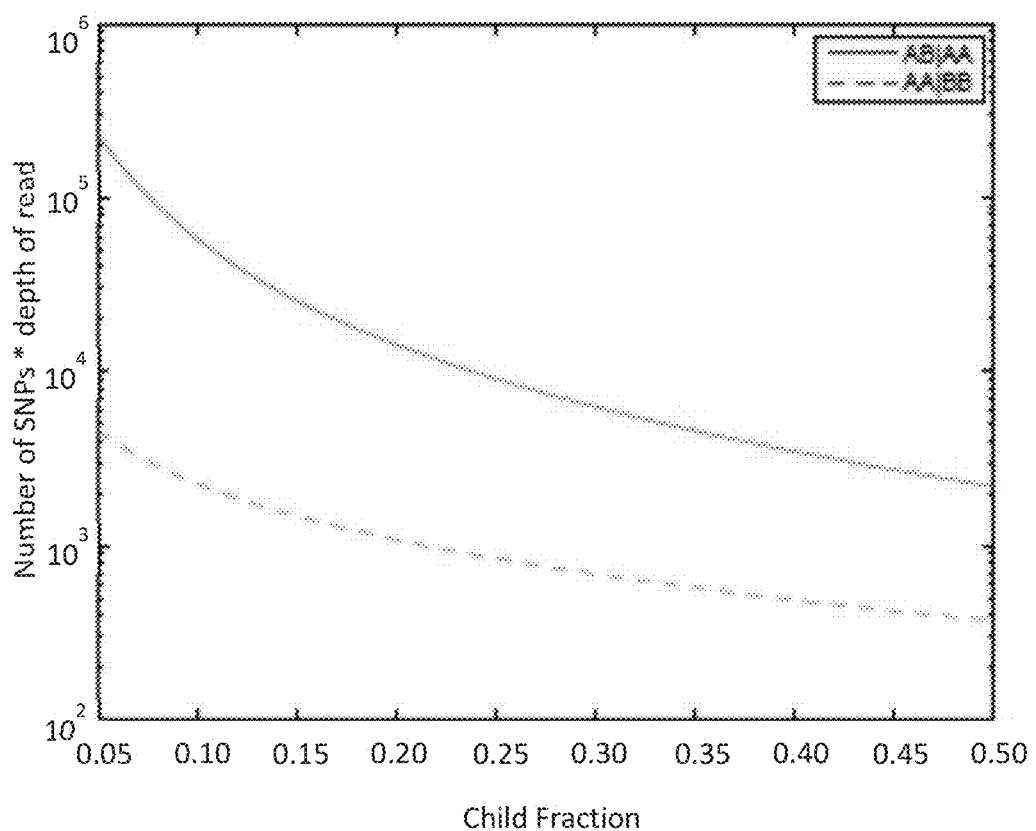
FIG. 1 shows a required number of measurements as a function of child concentration.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

In an embodiment, the present disclosure provides ex vivo methods for determining the ploidy status of a chromosome in a gestating fetus from genotypic data measured from a mixed sample of DNA (i.e., DNA from the mother of the fetus, and DNA from the fetus) and from genotypic data measured from a sample of genetic material from the mother and optionally also from the father, wherein the determining is done by using a joint distribution model to create a set of expected allele distributions for different possible fetal ploidy states given the parental genotypic data, and comparing the expected allelic distributions to the pattern of measured allelic distributions measured in the mixed sample, and choosing the ploidy state whose expected allelic distribution pattern most closely matches the observed allelic distribution pattern. In an embodiment, the mixed sample is derived from maternal blood. In an embodiment, the mixed sample of DNA may be preferentially enriched at a plurality of polymorphic loci. In an embodiment, the preferential enrichment is done in a way that minimizes the allelic bias. In an embodiment, there is a composition of DNA that has been preferentially enriched in at a plurality of loci such that the allelic bias is low.

In an embodiment, the present disclosure provides methods for non-invasive prenatal diagnosis (NPD), specifically, determining the aneuploidy status of a fetus by observing allele distributions at a set of polymorphic alleles in genotypic data measured on DNA mixtures, where certain allele distributions are indicative of an aneuploid fetus, while other allele distributions are indicative of a euploid fetus. In one embodiment, the genotypic data is measured by sequencing DNA mixtures that were derived from maternal plasma. In one embodiment, the DNA sample may be preferentially enriched in molecules of DNA that correspond to the set of alleles whose allele distributions are being calculated.

In one embodiment, the method involves determining whether the distribution of observed allele measurements is indicative of a euploid or an aneuploid fetus using a joint distribution model. The use of a joint distribution model is a significant improvement over methods that determine heterozygosity rates by treating polymorpic loci independently in that the resultant determinations are of significantly higher accuracy. Without being bound by any particular theory, it is believed that one reason they are of higher accuracy is that the joint distribution model takes into account the linkage between SNPs, and likelihood of crossovers occurring. Another reason it is believed that they are of higher accuracy is that they can take into account alleles where the total number of reads is low, and the allele ratio method would produce disproportionately weighted stochastic noise.

In one embodiment, the method involves determining whether the distribution of observed allele measurements is indicative of a euploid or an aneuploid fetus using a maximum likelihood technique. The use of a maximum likelihood technique is a significant improvement over methods that use single hypothesis rejection technique in that the resultant determinations will be made with significantly higher accuracy. One reason is that single hypothesis rejection techniques set cut off thresholds based on only one measurement distribution rather than two, meaning that the thresholds are usually not optimal. Another reason is that the maximum likelihood technique allows the optimization of the cut off threshold for each individual sample instead of determining a cut off threshold to be used for all samples regardless of the particular characteristics of each individual sample. Another reason is that the use of a maximum likelihood technique allows the calculation of a confidence for each ploidy call.

In one embodiment, the method involves determining whether the distribution of observed allele measurements is indicative of a euploid or an aneuploid fetus without comparing the distribution of observed allele measurements on a suspect chromosome to a distribution of observed allele measurements on a reference chromosome that is expected to be disomic. This is a significant improvement over methods that require the use of a reference chromosome to determine whether a suspect chromosome is euploid or aneuploid. One example of where a ploidy calling technique that requires a reference chromosome would make an incorrect call is in the case of a 69XXX trisomic fetus, which would be called euploid since there is no reference diploid chromosome, while the method described herein would be able to determine that the fetus was trisomic.

In one embodiment, the method disclosed herein demonstrates how observing allele distributions at polymorphic alleles can be used to determine the ploidy state of a fetus with greater accuracy than methods in the prior art. In one embodiment, the method involves using algorithms that analyze the distribution of alleles found for alleles that have different parental contexts, and comparing the observed allele distributions to the expected allele distributions for different ploidy states for the different parental contexts (different parental genotypic patterns). This is an improvement over methods that do not utilize allele distribution patterns for alleles from a plurality of different parental contexts because it allows the use of significantly more genetic measurement data from a set of sequence data in the ploidy determination, resulting in a more accurate determination. In one embodiment, the method involves determining whether the distribution of observed allele measurements is indicative of a euploid or an aneuploid fetus using observed allelic distributions measured at loci where the mother is heterozygous. This is an improvement over methods that do not use observed allelic distributions are loci where the mother is heterozygous because it allows the use of about twice as much genetic measurement data from a set of sequence data in the ploidy determination, resulting in a more accurate determination.

In one embodiment, the method disclosed herein uses selective enrichment techniques that preserve the allele distributions that are present in the original sample of DNA. In some embodiments the amplification and/or selective enrichment technique may involve targeted amplification, hybrid capture, or circularizing probes. In some embodiments, methods for amplification or selective enrichment may involve using probes where the hybridizing region on the probe is separated from the variable region of the polymorphic allele by a small number of nucleotides. This separation results in lower amounts of allelic bias. This separation results in lower amounts of allelic bias. This is an improvement over methods that involve using probes where the hybridizing region on the probe is designed to hybridize at the base pair directly adjacent to the variable region of the polymorphic allele. This is an improvement over other methods that involve amplification and/or selective enrichment methods that do not preserve the allele distributions that are present in the original sample of DNA well. Low allelic bias is critical for ensuring that the measured genetic data is representative of the original sample in methods that involve either calculating allele ratios or allele measurement distributions. Since prior methods did not focus on polymorphic regions of the genome, or on the allele distributions, it was not obvious that techniques that preserved the allele distributions would result in more accurate ploidy state determinations. Since prior methods did not focus on using allelic distributions to determine ploidy state, it was not obvious that a composition where a plurality of loci were preferentially enriched with low allelic bias would be particularly valuable for determining a ploidy state of a fetus.

The methods described herein are particularly advantageous when used on samples where a small amount of DNA is available, or where the percent of fetal DNA is low. This is due to the correspondingly higher allele drop out rate that occurs when only a small amount of DNA is available, or the correspondingly higher fetal allele drop out rate when the percent of fetal DNA is low. A high allele drop out rate, meaning that a large percentage of the alleles were not measured for the target individual, results in poorly accurate fetal fractions calculations, and poorly accurate ploidy determinations. Since the method disclosed herein uses a joint distribution model that takes into account the linkage in inheritance patterns between SNPs, significantly more accurate ploidy determinations may be made.

It is possible to determine the ploidy state of an individual based on measurements when that individual's DNA is mixed with DNA of a related individual. In the case of free floating DNA found in maternal plasma, the DNA from the mother, with known karyotype and known genotype, is mixed with DNA of the fetus, with unknown karyotype and unknown genotype. It is possible to use the known genotypic information from one or both parents to predict a plurality of potential compositions of the DNA in the mixed sample for different ploidy states, different chromosome contributions from each parent to the fetus, and optionally, different fetal DNA fractions in the mixture. Each potential composition may be referred to as a hypothesis. The ploidy state of the fetus can then be determined by looking at the actual measurements, and determining which potential compositions are most likely given the observed data.

Non-Invasive Prenatal Diagnosis (NPD)

The process of non-invasive prenatal diagnosis involves a number of steps. Some of the steps may include: (1) obtaining the genetic material from the fetus; (2) enriching the genetic material of the fetus, ex vivo; (3) amplifying the genetic material, ex vivo; (4) preferentially enriching specific loci in the genetic material, ex vivo; (5) genotyping the genetic material, ex vivo; and (6) analyzing the genotypic data, on a computer, and ex vivo. Methods to reduce to practice these six and other relevant steps are described herein. At least some of the method steps are not directly applied on the body. In an embodiment, the present disclosure relates to methods of treatment and diagnosis applied to tissue and other biological materials isolated and separated from the body. At least some of the method steps are executed on a computer.

Some embodiments of the present disclosure allow a clinician to determine the genetic state of a fetus that is gestating in a mother in a non-invasive manner such that the health of the baby is not put at risk by the collection of the genetic material of the fetus, and that the mother is not required to undergo an invasive procedure. Moreover, in certain aspects, the present disclosure allows the fetal genetic state to be determined with high accuracy, significantly greater accuracy than, for example, the non-invasive maternal serum analyte based screens, such as the triple test, that are in wide use in prenatal care.

The accuracy of the methods disclosed herein is a result of an informatics approach to analysis of the genotype data, as described herein. Modern technological advances have resulted in the ability to measure large amounts of genetic information from a genetic sample using such methods as high throughput sequencing and genotyping arrays. The methods disclosed herein allow a clinician to take greater advantage of the large amounts of data available, and make a more accurate diagnosis of the fetal genetic state. The details of a number of embodiments are given below. Different embodiments may involve different combinations of the aforementioned steps. Various combinations of the different embodiments of the different steps may be used interchangeably.

In one embodiment, a blood sample is taken from a pregnant mother, and the free floating DNA in the plasma of the mother's blood, which contains a mixture of both DNA of maternal origin, and DNA of fetal origin, is used to determine the ploidy status of the fetus. In one embodiment of the present disclosure, a key step of the method involves preferential enrichment of those DNA sequences in a mixture of DNA that correspond to polymorphic alleles in a way that the allele ratios and/or allele distributions remain mostly consistent upon enrichment. In one embodiment of the present disclosure, the method involves sequencing a mixture of DNA that contains both DNA of maternal origin, and DNA of fetal origin. In one embodiment of the present disclosure, a key step of the method involves using measured allele distributions to determine the ploidy state of a fetus that is gestating in a mother.

This application makes reference to U.S. Utility application Ser. No. 11/603,406, filed Nov. 28, 2006; U.S. Utility application Ser. No. 12/076,348, filed Mar. 17, 2008; PCT Utility Application Serial No. PCT/US09/52730, filed Aug. 4, 2009; PCT Utility Application Serial No. PCT/US10/050, 824, filed Sep. 30, 2010. Some of the vocabulary used in this filing may have its antecedents in these references. Some of the concepts described herein may be better understood in light of the concepts found in these three references.

Screening Maternal Blood Containing Free Floating Fetal DNA

The methods described herein may be used to help determine the genotype of a child, fetus, or other target individual where the genetic material of the target is found in the presence of a quantity of other genetic material. In this disclosure, the discussion focuses on determining the genetic state of a fetus where the fetal DNA is found in maternal blood, but this example is not meant to limit to possible contexts that this method may be applied to. In addition, the method may be applicable in cases where the amount of target DNA is in any proportion with the non-target DNA; for example, the target DNA could make up anywhere between 0.000001 and 99.999999% of the DNA present. In addition, the non-target DNA does not necessarily need to be from one individual, or even from a related individual, as long as genetic data from non-target individual(s) is known. In one embodiment of the present disclosure, the method can be used to determine genotypic data of a fetus from maternal blood that contains fetal DNA. It may also be used in a case where there are multiple fetuses in the uterus of a pregnant woman, or where other contaminating DNA may be present in the sample, for example from other already born siblings.

This technique may make use of the phenomenon of fetal blood cells gaining access to maternal circulation through the placental villi. Ordinarily, only a very small number of fetal cells enter the maternal circulation in this fashion (not enough to produce a positive Kleihauer-Betke test for fetal-maternal hemorrhage). The fetal cells can be sorted out and analyzed by a variety of techniques to look for particular DNA sequences, but without the risks that these latter two invasive procedures inherently have. This technique may also make use of the phenomenon of free floating fetal DNA gaining access to maternal circulation by DNA release following apoptosis of placental tissue where the placental tissue in question contains DNA of the same genotype as the fetus. The free floating DNA found in maternal plasma has been shown to contain fetal DNA in proportions as high as 30-40% fetal DNA.

In one embodiment of the present disclosure, blood may be drawn from a pregnant woman. Research has shown that maternal blood may contain a small amount of free floating DNA from the fetus, in addition to free floating DNA of maternal origin. In addition, there also may be enucleated fetal blood cells containing DNA of fetal origin, in addition to many blood cells of maternal origin, which typically do not contain nuclear DNA. There are many methods know in the art to isolate fetal DNA, or create fractions enriched in fetal DNA. For example, chromatography has been show to create certain fractions that are enriched in fetal DNA.

Once the sample of maternal blood, plasma, or other fluid, drawn in a relatively non-invasive manner, and that contains an amount of fetal DNA, either cellular or free floating, either enriched in its proportion to the maternal DNA, or in its original ratio, is in hand, one may genotype the DNA found in said sample. The method described herein can be used to determine genotypic data of the fetus. For example, it can be used to determine the ploidy state at one or more chromosomes, it can be used to determine the identity of one or a set of SNPs, including insertions, deletions, and translocations. It can be used to determine one or more haplotypes, including the parent of origin of one or more genotypic features.

Note that this method will work with any nucleic acids that can be used for any genotyping and/or sequencing methods, such as the ILLUMINA INFINIUM ARRAY platform, AFFYMETRIX GENECHIP, ILLUMINA GENOME ANALYZER, or LIFE TECHNOLOGIES' SOLID SYSTEM. This includes extracted free-floating DNA from plasma or amplifications (e.g. whole genome amplification, PCR) of the same; genomic DNA from other cell types (e.g. human lymphocytes from whole blood) or amplifications of the same. For preparation of the DNA, any extraction or purification method that generates genomic DNA suitable for the one of these platforms will work as well. In one embodiment, storage of the samples may be done in a way that will minimize degradation (e.g. at −20 C or lower).

Parental Support

Some embodiments may be used in combination with the PARENTAL SUPPORT™ (PS) method, embodiments of which are described in U.S. application Ser. No. 11/603,406, U.S. application Ser. No. 12/076,348, and international application PCT/US09/52730, which are incorporated herein by reference in their entirety. PARENTAL SUPPORT™ is an informatics based approach that can be used to analyze genetic data. In some embodiments, the methods disclosed herein may be considered as part of the PARENTAL SUPPORT™ method. In some embodiments, The PARENTAL SUPPORT™ method is a collection of methods that may be used to determine the genetic data, with high accuracy, of one or a small number of cells, specifically to determine disease-related alleles, other alleles of interest, and/or the ploidy state of the cell(s). PARENTAL SUPPORT™ may refer to any of these methods. PARENTAL SUPPORT™ is an example of an informatics based method.

The PARENTAL SUPPORT™ method makes use of known parental genetic data, i.e. haplotypic and/or diploid genetic data of the mother and/or the father, together with the knowledge of the mechanism of meiosis and the imperfect measurement of the target DNA, and possible of one or more related individuals, in order to reconstruct, in silico, the genotype at a plurality of alleles, and/or the ploidy state of an embryo or of any target cell(s), and the target DNA at the location of key loci with a high degree of confidence. The PARENTAL SUPPORT™ method can reconstruct not only single nucleotide polymorphisms (SNPs) that were measured poorly, but also insertions and deletions, and SNPs or whole regions of DNA that were not measured at all. Furthermore, the PARENTAL SUPPORT™ method can both measure multiple disease-linked loci as well as screen for aneuploidy, from a single cell. In some embodiments, the PARENTAL SUPPORT™ method may be used to characterize one or more cells from embryos biopsied during an IVF cycle to determine the genetic condition of the one or more cells.

The PARENTAL SUPPORT™ method allows the cleaning of noisy genetic data. This may be done by inferring the correct genetic alleles in the target genome (embryo) using the genotype of related individuals (parents) as a reference. PARENTAL SUPPORT™ may be particularly relevant where only a small quantity of genetic material is available (e.g. PGD) and where direct measurements of the genotypes are inherently noisy due to the limited amounts of genetic material. The PARENTAL SUPPORT™ method is able to reconstruct highly accurate ordered diploid allele sequences on the embryo, together with copy number of chromosomes segments, even though the conventional, unordered diploid measurements may be characterized by high rates of allele dropouts, drop-ins, variable amplification biases and other errors. The method may employ both an underlying genetic model and an underlying model of measurement error. The genetic model may determine both allele probabilities at each SNP and crossover probabilities between SNPs. Allele probabilities may be modeled at each SNP based on data obtained from the parents and model crossover probabilities between SNPs based on data obtained from the HapMap database, as developed by the International HapMap Project. Given the proper underlying genetic model and measurement error model, maximum a posteriori (MAP) estimation may be used, with modifications for computationally efficiency, to estimate the correct, ordered allele values at each SNP in the embryo.

One aspect of the PARENTAL SUPPORT™ technology is a chromosome copy number calling algorithm that in some embodiments uses parental genotype contexts. To call the chromosome copy number, the algorithm may use the phenomenon of locus dropout (LDO) combined with distributions of expected embryonic genotypes. During whole genome amplification, LDO necessarily occurs. LDO rate is concordant with the copy number of the genetic material from which it is derived, i.e., fewer chromosome copies result in higher LDO, and vice versa. As such, it follows that loci with certain contexts of parental genotypes behave in a characteristic fashion in the embryo, related to the probability of allelic contributions to the embryo. For example, if both parents have homozygous BB states, then the embryo should never have AB or AA states. In this case, measurements on the A detection channel are expected to have a distribution determined by background noise and various interference signals, but no valid genotypes. Conversely, if both parents have homozygous AA states, then the embryo should never have AB or BB states, and measurements on the A channel are expected to have the maximum intensity possible given the rate of LDO in a particular whole genome amplification. When the underlying copy number state of the embryo differs from disomy, loci corresponding to the specific parental contexts behave in a predictable fashion, based on the additional allelic content that is contributed by, or is missing from, one of the parents. This allows the ploidy state at each chromosome, or chromosome segment, to be determined. The details of one embodiment of this method are described elsewhere in this disclosure.

The techniques outlined above, in some cases, are able to determine the genotype of an individual given a very small amount of DNA originating from that individual. This could be the DNA from one or a small number of cells, or it could be from an even smaller amount of DNA, for example, DNA found in maternal blood.

In the context of non-invasive prenatal diagnosis, the techniques described above may not be sufficient to determine the genotype and/or the ploidy state, or the partial genotype or partial ploidy state (meaning the genetic state of a subset of alleles or chromosomes) of an individual. This may be especially true when the DNA of the target individual is found in maternal blood, and the amount of maternal DNA present in the sample may be greater than the amount of DNA from the target individual. In other cases, the amount of maternal DNA present in the sample may be in a sufficiently great amount of DNA that it makes the determination of the genetic state of the target individual difficult.

DEFINITIONS

Single Nucleotide Polymorphism (SNP) refers to a single nucleotide that may differ between the genomes of two members of the same species. The usage of the term should not imply any limit on the frequency with which each variant occurs.

To Call a SNP refers to the act of making a decision about the true state of a particular base pair, taking into account the direct and indirect evidence.

Sequence refers to a DNA sequence or a genetic sequence. It refers to the primary, physical structure of the DNA molecule or strand in an individual. It refers to the sequence of nucleotides found in that DNA molecule, or the complementary strand to the DNA molecule.

Locus refers to a particular region of interest on the DNA of an individual, which may refer to a SNP, the site of a possible insertion or deletion, or the site of some other relevant genetic variation. Disease-linked SNPs may also refer to disease-linked loci.

Polymorphic Allele, also "Polymorphic Locus," refers to an allele or locus where the genotype varies between individuals within a given species. Some examples of polymorphic alleles include single nucleotide polymorphisms, short tandem repeats, deletions, duplications, and inversions.

Allele refers to the genes that occupy a particular locus.

To Call an Allele refers to the act of determining the genetic state at a particular locus of DNA. This may involve calling a SNP, a plurality of SNPs, or determining whether or not an insertion or deletion is present at that locus, or determining the number of insertions that may be present at that locus, or determining whether some other genetic variant is present at that locus.

Correct Allele Call refers to an allele call that correctly reflects the true state of the actual genetic material of an individual.

To Clean Genetic Data refers to the act of taking imperfect genetic data and correcting some or all of the errors or fill in missing data at one or more loci. In the presently disclosed embodiments, this may involve using the genetic data of related individuals and the method described herein.

Genetic Data also "Genotypic Data" refers to the data describing aspects of the genome of one or more individuals. It may refer to one or a set of loci, partial or entire sequences, partial or entire chromosomes, or the entire genome. It may refer to the identity of one or a plurality of nucleotides; it may refer to a set of sequential nucleotides, or nucleotides from different locations in the genome, or a combination thereof. Genotypic data is typically in silico, however, it is also possible to consider physical nucleotides in a sequence as chemically encoded genetic data. Genotypic Data may be said to be "on," "of," "at," "from" or "on" the individual(s). Genotypic Data may refer to output measurements from a genotyping platform where those measurements are made on genetic material.

Genetic Material also "Genetic Sample" refers to physical matter, such as tissue or blood, from one or more individuals containing DNA or RNA Imperfect Genetic Data refers to genetic data with any of the following: allele dropouts, uncertain base pair measurements, incorrect base pair measurements, missing base pair measurements, uncertain measurements of insertions or deletions, uncertain measurements of chromosome segment copy numbers, spurious signals, missing measurements, other errors, or combinations thereof.

Noisy Genetic Data, also "Incomplete Genetic Data," refers to imperfect genetic data.

Uncleaned Genetic Data, also "Crude Genetic Data," refers to genetic data as measured, that is, where no method has been used to correct for the presence of noise or errors in the raw genetic data.

Confidence refers to the statistical likelihood that the called SNP, allele, set of alleles, ploidy call, or determined number of chromosome segment copies correctly represents the real genetic state of the individual.

Ploidy Calling, also "Chromosome Copy Number Calling," or "Copy Number Calling" (CNC), refers to the act of determining the quantity and chromosomal identity of one or more chromosomes present in a cell.

Aneuploidy refers to the state where the wrong number of chromosomes are present in a cell. In the case of a somatic human cell it refers to the case where a cell does not contain 22 pairs of autosomal chromosomes and one pair of sex chromosomes. In the case of a human gamete, it refers to the case where a cell does not contain one of each of the 23 chromosomes. In the case of a single chromosome, it refers to the case where more or less than two homologous but non-identical chromosomes are present, and where each of the two chromosomes originate from a different parent.

Ploidy State refers to the quantity and chromosomal identity of one or more chromosomes in a cell.

Chromosomal Identity refers to the referent chromosome number. Normal humans have 22 types of numbered autosomal chromosomes, and two types of sex chromosomes. It may also refer to the parental origin of the chromosome. It may also refer to a specific chromosome inherited from the parent. It may also refer to other identifying features of a chromosome.

The State of the Genetic Material or simply "Genetic State" refers to the identity of a set of SNPs on the DNA, to the phased haplotypes of the genetic material, and to the sequence of the DNA, including insertions, deletions, repeats and mutations. It may also refer to the ploidy state of one or more chromosomes, chromosomal segments, or set of chromosomal segments.

Allelic Data refers to a set of genotypic data concerning a set of one or more alleles. It may refer to the phased, haplotypic data. It may refer to SNP identities, and it may refer to the sequence data of the DNA, including insertions, deletions, repeats and mutations. It may include the parental origin of each allele.

Allelic State refers to the actual state of the genes in a set of one or more alleles. It may refer to the actual state of the genes described by the allelic data.

Allelic Distribution refers to the distribution of the set of alleles observed at a set of loci. An allelic distribution for one locus is an allele ratio.

Allelic Distribution Pattern refers to a set of different allele distributions for different parental contexts. Certain allelic distribution patterns may be indicative of certain ploidy states.

Allelic Bias refers to the degree to which the measured ratio of alleles at a heterozygous locus is different to the ratio that was present in the original sample of DNA. The degree of allelic bias at a particular locus is equal to the observed allelelic ratio at that locus, as measured, divided by the ratio of alleles in the original DNA sample at that locus. Allelic bias may be defined to be greater than one, such that if the calculation of the degree of allelic bias returns a value, x, that is less than 1, then the degree of allelic bias may be restated as 1/x.

Matched Copy Error, also "Matching Chromosome Aneuploidy" (MCA), refers to a state of aneuploidy where one cell contains two identical or nearly identical chromosomes. This type of aneuploidy may arise during the formation of the gametes in mitosis, and may be referred to as a mitotic non-disjunction error. Matching trisomy may refer to the case where three copies of a given chromosome are present in an individual and two of the copies are identical.

Unmatched Copy Error, also "Unique Chromosome Aneuploidy" (UCA), refers to a state of aneuploidy where one cell contains two chromosomes that are from the same parent, and that may be homologous but not identical. This type of aneuploidy may arise during meiosis, and may be referred to as a meiotic error. Unmatching trisomy may refer to the case where three copies of a given chromosome are present in an individual and two of the copies are from the same parent, and are homologous, but are not identical.

Homologous Chromosomes refers to chromosomes that contain the same set of genes that normally pair up during meiosis.

Identical Chromosomes refers to chromosomes that contain the same set of genes, and for each gene they have the same set of alleles that are identical, or nearly identical.

Allele Drop Out (ADO) refers to the situation where one of the base pairs in a set of base pairs from homologous chromosomes at a given allele is not detected.

Locus Drop Out (LDO) refers to the situation where both base pairs in a set of base pairs from homologous chromosomes at a given allele are not detected.

Homozygous refers to having similar alleles as corresponding chromosomal loci.

Heterozygous refers to having dissimilar alleles as corresponding chromosomal loci.

Heterozygosity Rate refers to the rate of individuals in the population having heterozygous alleles at a given locus. The heterozygosity rate may also refer to the expected or measured ratio of alleles, at a given locus in an individual, or a sample of DNA.

Highly Informative Single Nucleotide Polymorphism (HISNP) refers to a SNP where the fetus has an allele that is not present in the mother's genotype.

Chromosomal Region refers to a segment of a chromosome, or a full chromosome.

Segment of a Chromosome refers to a section of a chromosome that can range in size from one base pair to the entire chromosome.

Chromosome refers to either a full chromosome, or also a segment or section of a chromosome.

Copies refers to the number of copies of a chromosome segment, to identical copies, or to non-identical, homologous copies of a chromosome segment wherein the different copies of the chromosome segment contain a substantially similar set of loci, and where one or more of the alleles are different. Note that in some cases of aneuploidy, such as the M2 copy error, it is possible to have some copies of the given chromosome segment that are identical as well as some copies of the same chromosome segment that are not identical.

Haplotype refers to a combination of alleles at multiple loci that are transmitted together on the same chromosome. Haplotype may refer to as few as two loci or to an entire chromosome depending on the number of recombination events that have occurred between a given set of loci. Haplotype can also refer to a set of single nucleotide polymorphisms (SNPs) on a single chromatid that are statistically associated.

Haplotypic Data, also "Phased Data" or "Ordered Genetic Data," refers to data from a single chromosome in a diploid or polyploid genome, i.e., either the segregated maternal or paternal copy of a chromosome in a diploid genome.

Phasing refers to the act of determining the haplotypic genetic data of an individual given unordered, diploid (or polyploidy) genetic data. It may refer to the act of determining which of two genes at an allele, for a set of alleles found on one chromosome, are associated with each of the two homologous chromosomes in an individual.

Phased Data refers to genetic data where the haplotype has been determined.

Unordered Genetic Data refers to pooled data derived from measurements on two or more chromosomes in a diploid or polyploid genome, e.g., both the maternal and paternal copies of a particular chromosome in a diploid genome.

Hypothesis refers to a set of possible ploidy states at a given set of chromosomes, or a set of possible allelic states at a given set of loci. The set of possibilities may contain one or more elements.

Copy Number Hypothesis, also "Ploidy State Hypothesis," refers to a hypothesis concerning the number of copies of a particular chromosome in an individual. It may also refer to a hypothesis concerning the identity of each of the chromosomes, including the parent of origin of each chromosome, and which of the parent's two chromosomes are present in the individual. It may also refer to a hypothesis concerning which chromosomes, or chromosome segments, if any, from a related individual correspond genetically to a given chromosome from an individual.

Allelic Hypothesis refers to a possible allelic state for a given set of alleles. A set of allelic hypotheses may refer to a set of hypotheses that describe, together, all of the possible allelic states in the set of alleles. It may also refer to a hypothesis concerning which chromosomes, or chromosome segments, if any, from a related individual correspond genetically to a given chromosome from an individual.

Target Individual refers to the individual whose genetic data is being determined. In one context, only a limited amount of DNA is available from the target individual. In one context, the target individual is a fetus. In some embodiments, there may be more than one target individual. In some embodiments, each fetus that originated from a pair of parents may be considered to be target individuals.

Related Individual refers to any individual who is genetically related to, and thus shares haplotype blocks with, the target individual. In one context, the related individual may be a genetic parent of the target individual, or any genetic material derived from a parent, such as a sperm, a polar body, an embryo, a fetus, or a child. It may also refer to a sibling, parent or a grandparent.

Sibling refers to any individual whose parents are the same as the individual in question. In some embodiments, it may refer to a born child, an embryo, or a fetus, or one or more cells originating from a born child, an embryo, or a fetus. A sibling may also refer to a haploid individual that originates from one of the parents, such as a sperm, a polar body, or any other set of haplotypic genetic matter. An individual may be considered to be a sibling of itself.

Fetal refers to "of the fetus," but it also may refer to "of the placenta". In a pregnant woman, some portion of the placenta is genetically similar to the fetus, and the free floating fetal DNA found in maternal blood may have originated from the portion of the placenta with a genotype that matches the fetus. Note that the genetic information in half of the chromosomes in a fetus were inherited from the mother of the fetus. In some embodiments, the DNA from these maternally inherited chromosomes that came from a fetal cell are considered to be "of fetal origin," not "of maternal origin."

DNA of Fetal Origin refers to DNA that was originally part of a cell whose genotype was essentially equivalent to that of the fetus.

DNA of Maternal Origin refers to DNA that was originally part of a cell whose genotype was essentially equivalent to that of the mother.

Child is used interchangeably with the terms embryo, blastomere, and fetus. Note that in the presently disclosed embodiments, the concepts described apply equally well to individuals who are a born child, a fetus, an embryo or a set of cells therefrom. The use of the term child may simply be meant to connote that the individual referred to as the child is the genetic offspring of the parents.

Parent refers to the genetic mother or father of an individual. An individual typically has two parents, a mother and a father. A parent may be considered to be an individual.

Parental Context refers to the genetic state of a given SNP, on each of the two relevant chromosomes for each of the two parents of the target.

Develop As Desired, also "Develop Normally," refers to a viable embryo implanting in a uterus and resulting in a pregnancy. It may also refer to the pregnancy continuing and resulting in a live birth. It may also refer to the born child being free of chromosomal abnormalities. It may also refer to the born child being free of other undesired genetic conditions such as disease-linked genes. The term "develop as desired" encompasses anything that may be desired by parents or healthcare facilitators. In some cases, "develop as desired" may refer to an unviable or viable embryo that is useful for medical research or other purposes.

Insertion Into a Uterus refers to the process of transferring an embryo into the uterine cavity in the context of in vitro fertilization.

Clinical Decision refers to any decision to take or not take an action that has an outcome that affects the health or survival of an individual. In the context of prenatal diagnosis, a clinical decision refers to a decision to abort or not abort a fetus. A clinical decision may also refer to a decision to conduct further testing, to take actions to mitigate an undesirable phenotype, or to take actions to prepare for the birth of a child with abnormalities.

Platform Response refers to the mathematical characterization of the input/output characteristics of a genetic measurement platform, and may be used as a measure of the statistically predictable measurement differences. The platform response may concern the mathematical characterization of expected possible error rates in a set of data measured from a genotyping platform.

Informatics Based Method refers to a method designed to determine the ploidy state at one or more chromosomes or the allelic state at one or more alleles by statistically inferring the most likely state, rather than by directly physically measuring the state. In one embodiment of the present disclosure, the informatics based technique may be one disclosed in this patent. In one embodiment of the present disclosure it may be PARENTAL SUPPORT™.

Primary Genetic Data refers to the analog intensity signals that are output by a genotyping platform. In the context of SNP arrays, primary genetic data refers to the intensity signals before any genotype calling has been done. In the context of sequencing, primary genetic data refers to the analog measurements, analogous to the chromatogram, that comes off the sequencer before the identity of any base pairs have been determined, and before the sequence has been mapped to the genome.

Secondary Genetic Data refers to processed genetic data that are output by a genotyping platform. In the context of a SNP array, the secondary genetic data refers to the allele calls made by software associated with the SNP array reader, wherein the software has made a call whether a given allele is present or not present in the sample. In the context of sequencing, the secondary genetic data refers to the base pair identities of the sequences have been determined, and possibly also the sequences have been mapped to the genome.

Non-Invasive Prenatal Diagnosis (NPD), or also "Non-Invasive Prenatal Screening" (NPS), refers to a method of determining the genetic state of a fetus that is gestating in a mother using genetic material found in the mother's blood, where the genetic material is obtained by drawing the mother's intravenous blood.

Preferential Enrichment of DNA that corresponds to a locus, or preferential enrichment of DNA at a locus, refers to any method that results in the percentage of molecules of DNA in a post-enrichment DNA mixture that correspond to the locus being higher than the percentage of molecules of DNA in the pre-enrichment DNA mixture that correspond to the locus. The method may involve selective amplification of DNA molecules that correspond to a locus. The method may involve removing DNA molecules that do not correspond to the locus. The method may involve a combination of methods. The degree of enrichment is defined as the percentage of molecules of DNA in the post-enrichment mixture that correspond to the locus divided by the percentage of molecules of DNA in the pre-enrichment mixture that correspond to the locus. Preferential enrichment may be carried out at a plurality of loci. In some embodiments of the present disclosure, the degree of enrichment is greater than 20. In some embodiments of the present disclosure, the degree of enrichment is greater than 200. When preferential enrichment is carried out at a plurality of loci, the degree of enrichment may refer to the average degree of enrichment of all of the loci.

Amplification refers to a method that increases the number of copies of a molecule of DNA.

Selective Amplification refers to a method that increases the number of copies of a particular molecule of DNA, or molecules of DNA that correspond to a particular region of DNA. It may also refer to a method that increases the number of copies of a particular targeted molecule of DNA, or targeted region of DNA more than it increases non-targeted molecules or regions of DNA. Selective amplification may be a method of preferential enrichment.

Targeting refers to a method used to preferentially enrich those molecules of DNA that correspond to a set of loci, in a mixture of DNA.

Joint Distribution Model refers to a model that defines the probability of events defined in terms of multiple random variables, given a plurality of random variables defined on the same probability space, where the probabilities of the variable are linked.

Different Implementations of the Presently Disclosed Embodiments

Any of the embodiments disclosed herein may be implemented in digital electronic circuitry, integrated circuitry, specially designed ASICs (application-specific integrated circuits), computer hardware, firmware, software, or in combinations thereof. Apparatus of the presently disclosed embodiments can be implemented in a computer program product tangibly embodied in a machine-readable storage device for execution by a programmable processor; and method steps of the presently disclosed embodiments can be performed by a programmable processor executing a program of instructions to perform functions of the presently disclosed embodiments by operating on input data and generating output. The presently disclosed embodiments can be implemented advantageously in one or more computer programs that are executable and/or interpretable on a programmable system including at least one programmable processor, which may be special or general purpose, coupled to receive data and instructions from, and to transmit data and instructions to, a storage system, at least one input device, and at least one output device. Each computer program can be implemented in a high-level procedural or object-oriented programming language, or in assembly or machine language if desired; and in any case, the language can be a compiled or interpreted language. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Any of the methods described herein may include the output of data in a physical format, such as on a computer screen, or on a paper printout. In explanations of any embodiments elsewhere in this document, it should be understood that the described methods may be combined with the output of the actionable data in a format that can be acted upon by a physician. In addition, the described methods may be combined with the actual execution of a clinical decision that results in a clinical treatment, or the execution of a clinical decision to make no action. Some of the embodiments described in the document for determining genetic data pertaining to a target individual may be combined with the decision to select one or more embryos for transfer in the context of IVF, optionally combined with the process of transferring the embryo to the womb of the prospective mother. Some of the embodiments described in the document for determining genetic data pertaining to a target individual may be combined with the notification of a potential chromosomal abnormality, or lack thereof, with a medical professional, optionally combined with the decision to abort, or to not abort, a fetus in the context of prenatal diagnosis. Some of the embodiments described herein may be combined with the output of the actionable data, and the execution of a clinical decision that results in a clinical treatment, or the execution of a clinical decision to make no action.

Hypotheses

A hypothesis may refer to a possible genetic state. It may refer to a possible ploidy state. It may refer to a possible allelic state. A set of hypotheses refers to a set of possible genetic states. In some embodiments, a set of hypotheses may be designed such that one hypothesis from the set will correspond to the actual genetic state of any given individual. In some embodiments, a set of hypotheses may be designed such that every possible genetic state may be described by at least one hypothesis from the set. In some embodiments of the present disclosure, one aspect of the method is to determine which hypothesis corresponds to the actual genetic state of the individual in question.

In another embodiment of the present disclosure, one step involves creating a hypothesis. In some embodiments it may be a copy number hypothesis. In some embodiments it may involve a hypothesis concerning which segments of a chromosome from each of the related individuals correspond genetically to which segments, if any, of the other related individuals. Creating a hypothesis may refer to the act of setting the limits of the variables such that the entire set of possible genetic states that are under consideration are encompassed by those variables.

A "copy number hypothesis," also called a "ploidy hypothesis," or a "ploidy state hypothesis," may refer to a hypothesis concerning a possible ploidy state for a given chromosome, or section of a chromosome, in the target individual. It may also refer to the ploidy state at more than one of the chromosomes in the individual. A set of copy number hypotheses may refer to a set of hypotheses where each hypothesis corresponds to a different possible ploidy state in an individual. A set of hypotheses concern to a set of possible ploidy states, a set of possible parental haplotype contributions, a set of possible fetal DNA percentages in the mixed sample, or combinations thereof.

A normal individual contains one of each chromosome from each parent. However, due to errors in meiosis and mitosis, it is possible for an individual to have 0, 1, 2, or more of a given chromosome from each parent. In practice, it is rare to see more that two of a given chromosomes from a parent. In this disclosure, the embodiments only consider the possible hypotheses where 0, 1, or 2 copies of a given chromosome come from a parent. In some embodiments, for a given chromosome, there are nine possible hypotheses: the three possible hypothesis concerning 0, 1, or 2 chromosomes of maternal origin, multiplied by the three possible hypotheses concerning 0, 1, or 2 chromosomes of paternal origin. Let (m,f) refer to the hypothesis where m is the number of a given chromosome inherited from the mother, and f is the number of a given chromosome inherited from the father. Therefore, the nine hypotheses are (0,0), (0,1), (0,2), (1,0), (1,1), (1,2), (2,0), (2,1), and (2,2). These may also be written as $H_{00}$, $H_{01}$, $H_{02}$, $H_{10}$, $H_{12}$, $H_{20}$, $H_{21}$, and $H_{22}$. The different hypotheses correspond to different ploidy states. For example, (1,1) refers to a normal disomic chromosome; (2,1) refers to a maternal trisomy, and (0,1) refers to a paternal monosomy. In some embodiments, the case where two chromosomes are inherited from one parent and one chromosome is inherited from the other parent may be further differentiated into two cases: one where the two chromosomes are identical (matched copy error), and one where the two chromosomes are homologous but not identical (unmatched copy error). In these embodiments, there are sixteen possible hypotheses. It should be understood that it is possible to use other sets of hypotheses, and a different number of hypotheses.

In some embodiments of the present disclosure, the ploidy hypothesis may refer to a hypothesis concerning which chromosome from other related individuals correspond to a chromosome found in the target individual's genome. In some embodiments, a key to the method is the fact that related individuals can be expected to share haplotype blocks, and using measured genetic data from related individuals, along with a knowledge of which haplotype blocks match between the target individual and the related individual, it is possible to infer the correct genetic data for a target individual with higher confidence than using the target individual's genetic measurements alone. As such, in some embodiments, the ploidy hypothesis may concern not only the number of chromosomes, but also which chromosomes in related individuals are identical, or nearly identical, with one or more chromosomes in the target individual.

An allelic hypothesis, or an "allelic state hypothesis" may refer to a hypothesis concerning a possible allelic state of a set of alleles. In some embodiments, a key to this method is, as described above, related individuals may share haplotype blocks, which may help the reconstruction of genetic data that was not perfectly measured. An allelic hypothesis may also refer to a hypothesis concerning which chromosomes, or chromosome segments, if any, from a related individual correspond genetically to a given chromosome from an individual. The theory of meiosis tells us that each chromosome in an individual is inherited from one of the two parents, and this is a nearly identical copy of a parental chromosome. Therefore, if the haplotypes of the parents are known, that is, the phased genotype of the parents, then the genotype of the child may be inferred as well. (The term child, here, is meant to include any individual formed from two gametes, one from the mother and one from the father). In one embodiment of the present disclosure, the allelic hypothesis describes a possible allelic state, at a set of alleles, including the haplotypes, as well as which chromosomes from related individuals may match the chromosome(s) which contain the set of alleles.

Once the set of hypotheses have been defined, when the algorithms operate on the input genetic data, they may output a determined statistical probability for each of the hypotheses under consideration. The probabilities of the various hypotheses may be determined by mathematically calculating, for each of the various hypotheses, the value that the probability equals, as stated by one or more of the expert techniques, algorithms, and/or methods described elsewhere in this disclosure, using the relevant genetic data as input.

Once the probabilities of the different hypotheses are estimated, as determined by a plurality of techniques, they may be combined. This may entail, for each hypothesis, multiplying the probabilities as determined by each technique. The product of the probabilities of the hypotheses may be normalized. Note that one ploidy hypothesis refers to one possible ploidy state for a chromosome.

The process of "combining probabilities," also called "combining hypotheses," or combining the results of expert techniques, is a concept that should be familiar to one skilled in the art of linear algebra. One possible way to combine probabilities is as follows: When an expert technique is used to evaluate a set of hypotheses given a set of genetic data, the output of the method is a set of probabilities that are associated, in a one-to-one fashion, with each hypothesis in the set of hypotheses. When a set of probabilities that were determined by a first expert technique, each of which are associated with one of the hypotheses in the set, are combined with a set of probabilities that were determined by a second expert technique, each of which are associated with the same set of hypotheses, then the two sets of probabilities are multiplied. This means that, for each hypothesis in the set, the two probabilities that are associated with that hypothesis, as determined by the two expert methods, are multiplied together, and the corresponding product is the output probability. This process may be expanded to any number of expert techniques. If only one expert technique is used, then the output probabilities are the same as the input probabilities. If more than two expert techniques are used, then the relevant probabilities may be multiplied at the same time. The products may be normalized so that the probabilities of the hypotheses in the set of hypotheses sum to 100%.

In some embodiments, if the combined probabilities for a given hypothesis are greater than the combined probabilities for any of the other hypotheses, then it may be considered that that hypothesis is determined to be the most likely. In some embodiments, a hypothesis may be determined to be the most likely, and the ploidy state, or other genetic state, may be called if the normalized probability is greater than a threshold. In one embodiment, this may mean that the number and identity of the chromosomes that are associated with that hypothesis may be called as the ploidy state. In one embodiment, this may mean that the identity of the alleles that are associated with that hypothesis may be called as the allelic state. In some embodiments, the threshold may be between about 50% and about 80%. In some embodiments the threshold may be between about 80% and about 90%. In some embodiments the threshold may be between about 90% and about 95%. In some embodiments the threshold may be between about 95% and about 99%. In some embodiments the threshold may be between about 99% and about 99.9%. In some embodiments the threshold may be above about 99.9%.

Parental Contexts

The parental context may refer to the genetic state of a given SNP, on each of the two relevant chromosomes for each of the two parents of the target. Note that in one embodiment, the parental context does not refer to the allelic state of the target, rather, it refers to the allelic state of the parents. The parental context for a given SNP may consist of four base pairs, two paternal and two maternal; they may be the same or different from one another. It is typically written as "$m_1m_2|f_1f_2$," where $m_1$ and $m_2$ are the genetic state of the given SNP on the two maternal chromosomes, and $f_1$ and $f_2$ are the genetic state of the given SNP on the two paternal chromosomes. In some embodiments, the parental context may be written as "$f_1f_2|m_1m_2$." Note that subscripts "1" and "2" refer to the genotype, at the given allele, of the first and second chromosome; also note that the choice of which chromosome is labeled "1" and which is labeled "2" is arbitrary.

Note that in this disclosure, A and B are often used to generically represent base pair identities; A or B could equally well represent C (cytosine), G (guanine), A (adenine) or T (thymine). For example, if, at a given allele, the mother's genotype was T on one chromosome, and G on the homologous chromosome, and the father's genotype at that allele is G on both of the homologous chromosomes, one may say that the target individual's allele has the parental context of AB|BB; it could also be said that the allele has the parental context of AB|AA. Note that, in theory, any of the four possible nucleotides could occur at a given allele, and thus it is possible, for example, for the mother to have a genotype of AT, and the father to have a genotype of GC at a given allele. However, empirical data indicate that in most cases only two of the four possible base pairs are observed at a given allele. In this disclosure the discussion assumes that only two possible base pairs will be observed at a given allele, although the embodiments disclosed herein could be modified to take into account the cases where this assumption does not hold.

A "parental context" may refer to a set or subset of target SNPs that have the same parental context. For example, if one were to measure 1000 alleles on a given chromosome on a target individual, then the context AA|BB could refer to the set of all alleles in the group of 1,000 alleles where the genotype of the mother of the target was homozygous, and the genotype of the father of the target is homozygous, but where the maternal genotype and the paternal genotype are dissimilar at that locus. If the parental data is not phased, and thus AB=BA, then there are nine possible parental contexts: AA|AA, AA|AB, AA|BB, AB|AA, AB|AB, AB|BB, BB|AA, BB|AB, and BB|BB. If the parental data is phased, and thus AB≠BA, then there are sixteen different possible parental contexts: AA|AA, AA|AB, AA|BA, AA|BB, AB|AA, AB|AB, AB|BA, AB|BB, BA|AA, BA|AB, BA|BA, BA|BB, BB|AA, BB|AB, BB|BA, and BB|BB. Every SNP allele on a chromosome, excluding some SNPs on the sex chromosomes, has one of these parental contexts. The set of SNPs wherein the parental context for one parent is heterozygous may be referred to as the heterozygous context.

Use of Parental Contexts in Sequencing

Non-invasive prenatal diagnosis is an important technique that can be used to determine the genetic state of a fetus from genetic material that is obtained in a non-invasive manner, for example from a blood draw on the pregnant mother. The blood could be separated and the plasma isolated, and size selection could also be used to isolate the DNA of the appropriate length. This isolated DNA can then be measured by a number of means, such as by hybridizing to a genotyping array and measuring the fluorescence, or by sequencing on a high throughput sequencer.

When sequencing is used for ploidy calling of a fetus in the context of non-invasive prenatal diagnosis, there are a number of ways to use the sequence data. The most common way one could use the sequence data is to simply count the number of reads that map to a given chromosome. For example, imagine if you are trying to figure out the ploidy state of chromosome 21 on the fetus. Further imagine that the DNA in the sample is comprised of 10% DNA of fetal origin, and 90% DNA of maternal origin. In this case, you could look at the average number of reads on a chromosome which can be expected to be disomic, for example chromosome 3, and compare that to the number of read on chromosome 21, where the reads are adjusted for the number of base pairs on that chromosome that are part of a unique sequence. If the fetus were euploid, one would expect the amount of DNA per unit of genome to be about equal at all locations (subject to stochastic variations). On the other hand, if the fetus were trisomic at chromosome 21, then one would expect there to be more slightly more DNA per genetic unit from chromosome 21 than the other locations on the genome. Specifically one would expect there to be about 5% more DNA from chromosome 21 in the mixture. When sequencing is used to measure the DNA, one would expect about 5% more uniquely mappable reads from chromosome 21 per unique segment than from the other chromosomes. One could use the observation of an amount of DNA from a particular chromosome that is higher than a certain threshold, when adjusted for the number of sequences that are uniquely mappable to that chromosome, as the basis for an aneuploidy diagnosis. Another method that may be used to detect aneuploidy is similar to that above, except that parental contexts could be taken into account.

When considering which alleles to target, one may consider the likelihood that some parental contexts are likely to be more informative than others. For example, AA|BB and the symmetric context BB|AA are the most informative contexts, because the fetus is known to carry an allele that is different from the mother. For reasons of symmetry, both AA|BB and BB|AA contexts may be referred to as AA|BB. Another set of informative parental contexts are AA|AB and BB|AB, because in these cases the fetus has a 50% chance of carrying an allele that the mother does not have. For reasons of symmetry, both AA|AB and BB|AB contexts may be referred to as AA|AB. A third set of informative parental contexts are AB|AA and AB|BB, because in these cases the fetus is carrying a known paternal allele, and that allele is also present in the maternal genome. For reasons of symmetry, both AB|AA and AB|BB contexts may be referred to as AB|AA. A fourth parental context is AB|AB where the fetus has an unknown allelic state, and whatever the allelic state, it is one in which the mother has the same alleles. The fifth parental context is AA|AA, where the mother and father are heterozygous.

Sample Preparation

In some embodiments, the method may involve amplifying DNA. One method of amplifying DNA is polymerase chain reaction (PCR). One method of amplifying DNA is whole genome amplification (WGA). There are three major methods available for WGA: ligation-mediated PCR (LM-PCR), degenerate oligonucleotide primer PCR (DOP-PCR), and multiple displacement amplification (MDA). In LM-PCR, short DNA sequences called adapters are ligated to blunt ends of DNA. These adapters contain universal amplification sequences, which are used to amplify the DNA by PCR. In DOP-PCR, random primers that also contain universal amplification sequences are used in a first round of annealing and PCR. Then, a second round of PCR is used to amplify the sequences further with the universal primer sequences. MDA uses the phi-29 polymerase, which is a highly processive and non-specific enzyme that replicates DNA and has been used for single-cell analysis. The major limitations to amplification of material from a single cell are (1) necessity of using extremely dilute DNA concentrations or extremely small volume of reaction mixture, and (2) difficulty of reliably dissociating DNA from proteins across the whole genome. Regardless, single-cell whole genome amplification has been used successfully for a variety of applications for a number of years. There are other method of amplifying DNA from a sample of DNA.

There are numerous difficulties in using DNA amplification in these contexts. Amplification of single-cell DNA (or DNA from a small number of cells, or from smaller amounts of DNA) by PCR can fail completely, as reported in 5-10% of the cases. This is often due to contamination of the DNA, the loss of the cell, its DNA, or accessibility of the DNA during the PCR reaction. Other sources of error that may arise in measuring the fetal DNA by amplification and microarray analysis include transcription errors introduced by the DNA polymerase where a particular nucleotide is incorrectly copied during PCR, and microarray reading errors due to imperfect hybridization on the array. The biggest problem, however, remains allele drop-out (ADO) defined as the failure to amplify one of the two alleles in a heterozygous cell. ADO can affect up to more than 40% of amplifications and has already caused PGD misdiagnoses. ADO becomes a health issue especially in the case of a dominant disease, where the failure to amplify can lead to implantation of an affected embryo. The need for more than one set of primers per each marker (in heterozygotes) complicate the PCR process. Therefore, more reliable PCR assays are being developed based on understanding the ADO origin. Reaction conditions for single-cell amplifications are under study. The amplicon size, the amount of DNA degradation, freezing and thawing, and the PCR program and conditions can each influence the rate of ADO.

Several techniques are in development to measure multiple SNPs on the DNA of a small number of cells, a single cell (for example, a blastomere), a small number of chromosomes, or from fragments of DNA such as those fragments found in plasma. There are techniques that use Polymerase Chain Reaction (PCR), followed by microarray genotyping analysis. Some PCR-based techniques include whole genome amplification (WGA) techniques such as multiple displacement amplification (MDA), and Molecular Inversion Probes (MIPS) that perform genotyping using multiple tagged oligonucleotides that may then be amplified using PCR with a single pair of primers.

Targeted Sequencing

The use of a method to target certain alleles followed by sequencing as part of a method for allele calling or ploidy calling may confer a number of unexpected advantages. Some methods by which DNA may be targeted, or selectively enriched, include using circularizing probes, linked inverted probes (LIPs), capture by hybridization methods such as SURE SELECT, and targeted PCR amplification strategies.

Some embodiments of the present disclosure involve the use of "Linked Inverted Probes" (LIPs), which have been previously described in the literature. LIPs is a generic term meant to encompass technologies that involve the creation of a circular molecule of DNA, where the probes are designed to hybridize to targeted region of DNA on either side of a targeted allele, such that addition of appropriate polymerases and/or ligases, and the appropriate conditions, buffers and other reagents, will complete the complementary, inverted region of DNA across the targeted allele to create a circular loop of DNA that captures the information found in the targeted allele. LIPs may also be called pre-circularized probes, pre-circularizing probes, or the circularizing probes. The LIPs probe may be a linear DNA molecule between 50 and 500 nucleotides in length, and in a preferred embodiment between 70 and 100 nucleotides in length; in some embodiments, it may be longer or shorter than described herein. Others embodiments of the present disclosure involve different incarnations, of the LIPs technology, such as Padlock Probes and Molecular Inversion Probes (MIPs).

In some embodiments of the present disclosure described herein, the method involves measuring genetic data for use with an informatics based method, such as PARENTAL SUPPORT™ (PS). PARENTAL SUPPORT™ is an informatics based approach to manipulating genetic data, aspects of which are described herein. The ultimate outcome of some of the embodiments is the actionable genetic data of an embryo or a fetus. The algorithms behind the PS method take the measured genetic data of the target individual, often an embryo or fetus, and the measured genetic data from related individuals, and are able to increase the accuracy with which the genetic state of the target individual is known. In one embodiment, the measured genetic data is used in the context of making ploidy determinations during prenatal genetic diagnosis. In another embodiment the measured genetic data is used in the context of making ploidy determinations or allele calls on embryos during in vitro fertilization. There are many methods that may be used to measure the genetic data of the individual and/or the related individuals in the aforementioned contexts. The different methods comprise a number of steps, those steps often involving amplification of genetic material, addition of oligonucleotide probes, ligation of specified DNA strands, isolation of sets of desired DNA, removal of unwanted components of a reaction, detection of certain sequences of DNA by hybridization, detection of the sequence of one or a plurality of strands of DNA by DNA sequencing methods. In some cases the DNA strands may refer to target genetic material, in some cases they may refer to primers, in some cases they may refer to synthesized sequences, or combinations thereof. These steps may be carried out in a number of different orders. Given the highly variable nature of molecular biology, it is generally not obvious which methods, and which combinations of steps, will perform poorly, well, or best in various situations.

Note that in theory it is possible to target any number loci in the genome, anywhere from one loci to well over one million loci. If a sample of DNA is subjected to targeting, and then sequenced, the percentage of the alleles that are read by the sequencer will be enriched with respect to their natural abundance in the sample. The degree of enrichment can be anywhere from one percent (or even less) to tens fold, hundred fold, thousand fold or even many million fold. In the human genome there are roughly 3 billion base pairs, and nucleotides, containing approximately 75 million polymorphic loci. The more loci that are targeted, the smaller the degree of enrichment is possible. The fewer the number of loci that are targeted, the greater degree of enrichment is possible, and the greater depth of read may be achieved at those loci for a given number of sequence reads.

In one embodiment of the present disclosure, the targeting may focus entirely on SNPs. A number of commercial targeting products are available to enrich exons. Surprisingly, targeting exclusively SNPs is particularly advantageous when using a method for NPD that relies on allele distributions. Currently, published methods for NPD using sequencing, for example U.S. Pat. No. 7,888,017, a type of read count analysis where the read counting focuses on counting the number of reads that map to a given chromosome, where the analyzed sequence reads do not focused on regions of the genome that are polymorphic. In one embodiment of the present disclosure, it is possible to use a targeting method that focuses on SNPs to enrich a genetic sample in polymorphic regions of the genome. In one embodiment, it is possible to focus on a small number of SNPs, for example between 1 and 100 SNPs, or a larger number, for example, between 100 and 1,000, between 1,000 and 10,000, between 10,000 and 100,000 or more than 100,000 SNPs. In one embodiment, it is possible to focus on one or a small number of chromosomes that are correlated with live trisomic births, for example chromosomes 13, 18, 21, X and Y, or some combination thereof. In one embodiment, it is possible to enrich the targeted SNPs by a small factor, for example between 1.01 fold and 100 fold, or by a larger factor, for example between 100 fold and 1,000,000 fold. In one embodiment of the present disclosure, it is possible to use a targeting method to create a sample of DNA that is preferentially enriched in polymorphic regions of the genome. In one embodiment, it is possible to use the method to create a sample of DNA that is preferentially enriched in a small number of SNPs, for example between 1 and 100 SNPs, or a larger number of SNPs, for example, between 100 and 50,000 SNPs. In one embodiment, it is possible to use the method to create a DNA sample that is enriched in SNPs located on one or a small number of chromosomes that are correlated with live trisomic births, for example chromosomes 13, 18, 21, X and Y, or some combination thereof. In one embodiment, it is possible to use the method to create a sample of DNA that is preferentially enriched in a small number of SNPs, for example between 1 and 100 SNPs, or a larger number of SNPs, for example, between 100 and 50,000 SNPs. In one embodiment, it is possible to use the method to create a sample of DNA that is enriched targeted SNPs by a small factor, for example between 1.01 fold and 100 fold, or by a larger factor, for example between 100 fold and 1,000,000 fold. In one embodiment, it is possible to use this method to create a mixture of DNA with any of these characteristics where the mixture of DNA contains maternal DNA and also free floating fetal DNA. In one embodiment, it is possible to use this method to create a mixture of DNA that has any combination of these factors. For example, a mixture of DNA that contains maternal DNA and fetal DNA, and that is preferentially enriched in 200 SNPs, all of which are located on either chromosome 18 or 21, and which are enriched an average of 1000 fold. In another example, it is possible to use the method to create a mixture of DNA that is preferentially enriched in 50,000 SNPs that are all located on chromosomes 13, 18, 21, X and Y, and the average enrichment per loci is 200 fold. Any of the targeting methods described herein can be used to create mixtures of DNA that are preferentially enriched in certain loci.

In some embodiments, the method may further comprise measuring the DNA contained in the mixed fraction using a DNA sequencer, and the DNA contained in the mixed fraction contains a disproportionate number of sequences from one or more chromosomes, wherein the one or more chromosomes are taken from the group comprising chromosome 13, chromosome 18, chromosome 21, chromosome X, chromosome Y and combinations thereof.

A Method for Creating Samples that are Highly Enriched for Large Numbers of Alleles in an Unbiased Fashion, and Related Compositions of Matter In one embodiment, the method can be used to determine genotypes (base composition of the DNA at specific loci) and relative proportions of those genotypes from a mixture of DNA molecules, where those DNA molecules may have originated from one or a number of genetically distinct individuals. In one embodiment, the method can be used to determine the genotypes at a set of polymorphic loci, and the relative ratios of the amount of different alleles present at those loci. In one embodiment the polymorphic loci may consist entirely of SNPs. In one embodiment, the polymorphic loci can comprise SNPs, single tandem repeats, and other polymorphic regions. In one embodiment, the method can be used to determine the relative rations of different alleles at a set of polymorphic loci in a mixture of DNA, where the mixture of DNA is comprised of DNA that originates from a mother, and DNA that originates from a fetus. In one embodiment, the relative ratios of different alleles can be determined on a mixture of DNA isolated from blood from a pregnant woman. In one embodiment, the relative ratios of alleles at a set of loci can be used to determine the ploidy state of one or more chromosomes on a fetus that is gestating in the mother.

In one embodiment, the mixture of DNA molecules could be derived from DNA extracted from multiple cells of one individual. In one embodiment, the original collection of cells from which the DNA is derived may contain a mixture of diploid or haploid cells of the same or of different genotypes, if that individual is mosaic (germline or somatic). In one embodiment, the mixture of DNA molecules could also be derived from DNA extracted from single cells. In one embodiment, the mixture of DNA molecules could also be derived form DNA extracted from mixture of two or more cells of the same individual, or of different individuals. In one embodiment, the mixture of DNA molecules could be derived from DNA isolated from biological material that has already liberated from cells such as blood plasma, which is known to contain cell free DNA. In one embodiment, the this biological material may be a mixture of DNA from one or more individuals, as is the case during pregnancy where it has been shown that fetal DNA is present in the mixture.

In one embodiment of the present disclosure, the originating source of DNA is cells. The mixture may contain zero or more copies of a given chromosome. Normal healthy human cells typically contain two copies of each chromosome that were inherited from the two unrelated parents. These copies typically vary at many different locations (loci). The variations may be single nucleotide differences (SNPs), two or more nucleotide differences, insertions or deletions of one or more nucleotides, one or more exact copies of segments of DNA, which are often positioned adjacent to one another but can be located anywhere. Common ancestral relationships may also result in segments within the normal two copies of the DNA being identical or near identical. Germline or somatic mosacism may result in the cells derived form one individual being different in one or more chromosomal locations.

Method to Accurately Determine the Relative Proportion of Alleles at a Given Loci in a Sample:

Current sequencing approaches can be used to estimate the proportion of alleles in the sample. These methods randomly sample sequences from a pool DNA, termed shotgun sequencing. The proportion of a particular allele in the sequencing data is typically very low and can be determined by simple statistics. The human genome contains approximately 3 billion base pairs. So, if the sequencing method used make 100 bp reads, a particular allele will be measured about once in every 30 million sequence reads. In a case where two different alleles at a given loci are present, sufficient sequencing depth will yields a relative allele ratio that will eventually converge on the ratio with which the alleles are actually present in the mixture. More generally the relative ratios will converge on the actual ratios more slowly if there are more than two alleles at a particular locus in the mixture.

In one embodiment of the present disclosure, the method can be used to determine the relative ratios of two or more different haplotypes that contain the same set of loci in a sample of DNA. The different haplotypes could represent two different homologous chromosomes from one individual, three different homologous chromosomes from a trisomic individual, three different homologous haplotypes from a mother and a fetus where one of the haplotypes is shared between the mother and the fetus, three or four haplotypes from a mother and fetus where one or two of the haplotypes are shared between the mother and the fetus, or other combinations. If one or more of the haplotypes are known, or the diploid genotypes of one or more of the individuals are known, then a set of alleles that are polymorphic between the haplotypes can be chosen, and average allele ratios can be determined based on the set of alleles that uniquely originate from each of the haplotypes.

Direct sequencing of such a sample, however, is extremely inefficient as it results in many sequences for regions that are not polymorphic between the different haplotypes in the sample and therefore reveal no information about the proportion of the two haplotypes. Described herein is a method that specifically targets and enriches segments of DNA in the sample that are more likely to be polymorphic in the genome to increase the yield of allelic information obtained by sequencing. Note that for the allele ratios measured in an enriched sample to be truly representative of the actual haplotype ratios it is critical that there is little or no preferential enrichment of one allele as compared to the other allele at a given loci in the targeted segments. Current methods known in the art to target polymorphic alleles are designed to ensure that at least some of any alleles present are detected. However, these methods were not designed for the purpose of measuring the allele ratio of polymorphic alleles present in the original mixture. It is non-obvious that any particular method of target enrichment would be able to produce an enriched sample wherein the proportion of various alleles in the enriched sample is about the same as to the ratios of the alleles in the original unamplified sample. While enrichment methods may be designed, in theory, to accomplish such an aim, an ordinary person skilled in the art is aware that there is a great deal of stochastic or deterministic bias in current methods. On embodiment of the method described herein allows a plurality of alleles found in a mixture of DNA that correspond to a given locus in the genome to be amplified, or preferentially enriched in a way that the degree of enrichment of each of the alleles is nearly the same. Another way to say this is that the method allows the relative quantity of the alleles present in the mixture as a whole to be increased, while the ratio between the alleles that correspond to each locus remains essentially the same as they were in the original mixture of DNA. For the purposes of this disclosure, for the ratio to remain essentially the same, it is mean that the ratio of the alleles in the original mixture divided by the ratio of the alleles in the resulting mixture is between 0.5 and 1.5, between 0.8 and 1.2, between 0.9 and 1.1, between 0.95 and 1.05, between 0.98 and 1.02, between 0.99 and 1.01, between 0.995 and 1.005, between 0.998 and 1.002, between 0.999 and 1.001, or between 0.9999 and 1.0001.

In one embodiment, once a mixture has been preferentially enriched at the set of target loci, it may be sequenced using any one of the previous, current, or next generation of sequencing instruments that sequences a clonal sample (a sample generated from a single molecule; examples include ILLUMINA GAIIx, ILLUMINA HiSEQ, LIFE TECHNOLO- GIES SOLiD, 5500XL). The ratios can be evaluated by sequencing through the specific alleles within the targeted region. These sequencing reads can be analyzed and counted according the allele type and the rations of different alleles determined accordingly. For variations that are one to a few bases in length, detection of the alleles will be performed by sequencing and it is essential that the sequencing read span the allele in question in order to evaluate the allelic composition of that captured molecule. The total number of captured molecules assayed for the genotype can be increased by increasing the length of the sequencing read. Full sequencing of all molecules would guarantee collection of the maximum amount of data available in the enriched pool. However, sequencing is currently expensive, and a method that can measure a certain number of allele ratios using a lower number of sequence reads will have great value. In addition, there are technical limitations to the maximum possible length of read as well as accuracy limitations as read lengths increase. The alleles of greatest utility will be of one to a few bases in length, but theoretically any allele shorter than the length of the sequencing read can be used. While allele variations come in all types, the examples provided herein focus on SNPs or variants comprised of just a few neighboring base pairs. Larger variants such as segmental copy number variants can be detected by aggregations of these smaller variations in many cases as whole collections of SNP internal to the segment are duplicated. Variants larger than a few bases, such as STRs require special consideration and some targeting approaches work while others will not. The evaluation of the allelic rations is herein determined There are multiple targeting approaches that can be used to specifically isolate and enrich a one or a plurality of variant positions in the genome. Typically, these rely on taking advantage of invariant sequence flanking the variant sequence. There is prior art related to targeting in the context of sequencing where the substrate is maternal plasma (see, e.g., Liao et al., Clin. Chem.; 57(1): pp. 92-101). However, these approaches all use targeting probes that target exons, and do not focus on targeting polymorphic regions of the genome. In one embodiment of the present disclosure, the method involves using targeting probes that focus exclusively or almost exclusively on polymorphic regions. In one embodiment of the present disclosure, the method involves using targeting probes that focus exclusively or almost exclusively on SNPs. When polymorphic targeted DNA mixtures are sequenced and analyzed using an algorithm that determined ploidy using allele ratios, this targeting method is able to provide far more accurate ploidy determinations for a given number of sequence reads. In some embodiments of the present disclosure, the targeted polymorphic regions consist of at least 10% SNPs, at least 20% SNPs, at least 30% SNPs, at least 40% SNPs, at least 50% SNPs, at least 60% SNPs, at least 70% SNPs, at least 80% SNPs, at least 90% SNPs, at least 95% SNPs, at least 98% SNPs, at least 99% SNPs, at least 99.9% SNPs, exclusively SNPs.

Targeted Sequencing Using Circularizing Probes

One method of measuring genetic data involves the use of circularizing probes. Two papers that discuss a method involving circularizing probes that can be used to measure the genomic data of the target individual include: Porreca et al., Nature Methods, 2007 4(11), pp. 931-936.; and also Turner et al., Nature Methods, 2009, 6(5), pp. 315-316. The methods described in these papers may be used in combination with other methods described herein. Certain steps of the method from these two papers may be used in combination with other steps from other methods described herein.

In one embodiment of the methods, the genetic material of the target individual is amplified, and then the desired allelic genetic information is captured by circularizing appropriately designed oligonucleic probes, such as in the LIPs system. This may be followed by the genetic sequence of the circularized probes being measured to give the desired sequence data. In another embodiment, the appropriately designed oligonucleotides probes may be circularized directly on unamplified genetic material of the target individual, and amplified afterwards. Note that a number of amplification procedures may be used to amplify the original genetic material, or the circularized LIPs, including rolling circle amplification, MDA, or other amplification protocols. Different methods may be used to measure the genetic information on the target genome, for example using high throughput sequencing, Sanger sequencing, other sequencing methods, capture-by-hybridization, capture-by-circularization, multiplex PCR, other hybridization methods, and combinations thereof.

Once the genetic material of the individual has been measured using one or a combination of the above methods, an informatics based method, such as the PARENTAL SUPPORT™ method, along with the appropriate genetic measurements, can then be used to determination the ploidy state of one or more chromosomes on the individual, and/or the genetic state of one or a set of alleles, specifically those alleles that are correlated with a disease or genetic state of interest. Note that the use of LIPs has been reported for multiplexed capture of genetic sequences, followed by genotyping with sequencing. However, the use of sequencing data resulting from a LIPs-based strategy for the amplification of the genetic material found in a single cell, a small number of cells, or extracellular DNA, has not been used for the purpose of determining the ploidy state of a target individual.

Applying an informatics based method to determine the ploidy state of an individual from genetic data as measured by hybridization arrays, such as the ILLUMINA INFINIUM array, or the AFFYMETRIX gene chip has been described in documents references elsewhere in this document. However, the method described herein shows improvements over methods described previously in the literature. For example, the LIPs based approach followed by high throughput sequencing unexpectedly provides better genotypic data due to the approach having better capacity for multiplexing, better capture specificity, better uniformity, and low allelic bias. Greater multiplexing allows more alleles to be targeted, giving more accurate results. Better uniformity results in more of the targeted alleles being measured, giving more accurate results. Lower rates of allelic bias result in lower rates of miscalls, giving more accurate results. More accurate results result in an improvement in clinical outcomes, and better medical care.

In one embodiment of the present disclosure, a pregnant mother would like to determine if her fetus is afflicted with any gross chromosomal abnormalities. She goes to her doctor, and gives a sample of her blood, and she and her husband gives samples of their own DNA from cheek swabs. A laboratory researcher genotypes the parental DNA using the MDA protocol to amplify the parental DNA, and ILLUMINA INFINIUM arrays to measure the genetic data of the parents at a large number of SNPs. The researcher then spins down the blood, takes the plasma, and isolates a sample of free-floating DNA using size exclusion chromatography. Alternately, the researcher uses one or more fluorescent antibodies, such as one that is specific to fetal hemoglobin to isolate a nucleated fetal red blood cell. The researcher then takes the isolated or enriched fetal genetic material and amplifies it using a library of 70-mer oligonucleotides appropriately designed such that two ends of each oligonucleotide corresponded to the flanking sequences on either side of a target allele. Upon addition of a polymerase, ligase, and the appropriate reagents, the oligonucleotides underwent gap-filling circularization, capturing the desired allele. An exonuclease was added, heat-inactivated, and the products were used directly as a template for PCR amplification. The PCR products were sequenced on an ILLUMINA GENOME ANALYZER. The sequence reads were used as input for the PARENTAL SUPPORT™ method, which then predicted the ploidy state of the fetus.

It is important to note that LIPs may be used as a method for targeting specific loci in a sample of DNA for genotyping by methods other than sequencing. For example, LIPs may be used to target DNA for genotyping using SNP arrays or other DNA or RNA based microarrays.

The Use of Linked Inverted Probes for Genotyping SNPs, Repeat Expansion and Large Deletions Alleles In one embodiment of the present disclosure, inverted probes may be used to genotype a wide variety of loci, for example, not just SNPs, but also large repeats such as triple repeats and tandem repeats, or large deletions. There are a number of diseases that are characterized by such repeats and/or deletions. Methods of amplification and genotyping that have been described in the literature have a number of problems that preclude their use in a large scale multiplexed fashion.

The LIPs technologies, of which MIPs and PADLOCK PROBES are a subset, share a common feature in that they involve a synthesized DNA fragment in which the ends are specifically constructed to form complementary base-pairing to a target DNA under suitable reaction conditions, herein called the "probe," or the "pre-circularized probe," or the "pre-circularizing probe," or the "circularizing probe." Furthermore the ends of said probe are designed in a manner such that the 5-prime (5') and 3-prime (3') ends of the probe are oriented towards one another annealing of the probe, herein generally called "inverted-linked probes," to the target DNA, herein called "the template." Consequently, addition of dNTPs, polymerase, ligase, and suitable buffers, results in polymerization from the 3' end of the probe, herein referred to as "the extension," filling in the gap between the 3' and 5' ends of the probe with nucleotides complementary to the template DNA. Once the gap is completely filled, ligase catalyzes the formation of a covalent phosphodiester bond between the now adjacent 3' and 5' ends of the probe creating a complete circular molecule of DNA. There is no necessary upper limit to size of the gap between the 3' and 5' ends of the fragment that can be filled with complementary bases. A practical upper limit may be determined by the reaction conditions, the processivity of the polymerase, and the ability to amplify the fragment by subsequent PCR based methods.

The region of interest between the original 3' and 5' ends of the fragment may be amplified by various techniques after the circle, now intertwined with the template, has been released from the target DNA. Release may be achieved by breakage of the template molecule or by breakage of the now circular probe. This may be done along the backbone of the probe as not to disturb the newly polymerized target sequence. Amplification of the target region, herein referred to as "probe amplification," may then be accomplished by various PCR techniques or by rolling circle amplification (if the probe remains a circle).

In some embodiments of the present disclosure, this technique may be used to accomplish specific targeting and amplification of sequences in the genome. In addition, this technique enables efficient multiplexing, i.e. mixing in the same reaction vessel, of probes to distinct template targets. The physical linking of the two complementary sequences into a single probe backbone has the effect of limiting cross-reactions between unintended combinations of target sequences, as typically occurs with multiplex PCR. All of the newly extended probes may be amplified simultaneously using amplification primers or techniques common to all the probes. The resulting amplified sequences may be analyzed for size, size distribution, allele constitution, or specific sequence by various methods. Gel separation can reveal size and size distribution. Microarrays and quantitative PCR can reveal allele constitution using either target specific hybridization or probe specific hybridization, where probes are individually tagged with distinct sequences. Sequencing by methods, such as the Sanger dideoxy method, could also reveal sequence in certain circumstances. Sequencing using other methods, such as the clonal (e.g. polony, bridge) or single molecule sequencing methods, can reveal the sequence as well as counts of individual molecules in the amplified pool. Furthermore, sequencing enables mixing and sequencing multiple probe amplification pools from different individuals. One way to accomplish this would be for each initial probe pool applied to a sample to either contain a different synthesized sequence that could be used differentiate different samples, or a specific distinguishing sequence could be added and covalently linked to the products of the probe amplification. These sample specific sequences could then be detected during the sequence process allowing disambiguation as to from which sample each particular sequence instance was derived. In one embodiment, one could add probes after amplification; the order and timing of addition of the various reagents and probes may be different.

In one embodiment, LIPs may be used to detect certain disease alleles that are not easily detected using other PCR based techniques. Alleles of certain diseases are not amenable to PCR based amplification. For example, the disease Fragile X, an X-linked disorder, is caused by tandem expansion of a tri-nucleotide repeat of the DNA nucleotides CGG. When the number of repeats is greater than 45 repeats become unstable and become prone to further expansion. A chromosome with greater than 200 repeats is considered to have the full mutation. Both males, who only have one X chromosome, and heterozygous females, will show characteristics of the disease at repeats greater than about 200 triplets in size. One challenge in PCR based screening techniques is that PCR, while usually capable of amplifying the normal size range of alleles, will often fail to amplify expanded alleles due the highly repetitive nature of the DNA. Consequently, PCR based tests used on heterozygous individuals may yield a false negative test result when only the normal allele is detected.

In one embodiment, this problem may be solved by using at least two, but also possibly three or more distinct linked inverted probes. The first probe may be designed so that both ends are complementary to the DNA sequence flanking the repetitive sequence prone to expansion, herein called the "spanning probe." Upon binding, this probe would straddle the entire repeat region, enabling detection and amplification of the normal allele and some size range of expanded alleles. A second probe, herein called the "non-spanning probe," may be designed such that one end of the probe is complementary to the non-repetitive sequence upstream of the repeat and the other end complementary to the repeat itself. Similarly, another non-spanning probe may also be designed with one end complementary to the downstream non-repetitive DNA sequence and the other end complementary to the repetitive sequence. The spanning probe would be expected to extend and amplify in the presence of the normal allele as well as some size range of expanded alleles. However, for the same reasons that PCR fails at the largest size ranges of these repeat alleles, this probe may fail at the larger size ranges of the expanded allele. However, the non-spanning probes allow detection of these alleles. These probes bind to one side of the repeat, anchoring the probe while the other end of the probe is free to find to bind to numerous places within the repeat. Extension and amplification of these probes then yields a distribution of differently sized fragments. The size distribution can be detected through various methods including DNA separation techniques (e.g. agarose gel), or by direct sequencing of the amplified probes any clonal sequencing method. Collectively, the spanning and one or both of the non-spanning probes may be used to detect the presence of all possible genotypes, by sequencing, for example.

For an allele that can be extended and amplified by the spanning probe, the size of the allele may be readily observed upon analysis. If in a normal individual there are two different size normal alleles, both may be detectable by the spanning probe. If the size of one or both alleles is abnormal, but still within the limits of detection of the spanning probe, then again both alleles may be detectable. If the one or both of the alleles is so large such that it cannot be extended or amplified with the spanning probe, then the data from one or both of the non-spanning probes may be used to determine or estimate the repeat length, as both an internal positive control and as a means to demonstrate the presence of an allele that is larger than normal size rage. With normal PCR methods, large repeats simply fail to amplify. Consequently, in the circumstance where an individual is heterozygous for a normal allele and a greatly expanded allele and the expanded allele fails to amplify, then the individual will falsely appear to be homozygous for the normal allele. However, the combination of the spanning probe and non-spanning probes allow detection of the normal allele and observation of the expanded allele. Even though the non-spanning probe may not extend and amplify the largest possible fragments, the presence of any bands larger than the normal size will indicate the presence of an abnormal allele.

In one embodiment, LIPs may be used to detect large deletions with defined or potentially poorly defined end points. Large deletions are responsible for a number of important human disorders. For example, Hemophilia A can be caused by large deletions of varying size in the Factor VIII gene on the X chromosome; Duchenne and Becker Muscular Dystrophy can be caused by large deletions of varying size in the DMD gene, also on the X chromosome). There is a challenge in detecting large mutations using traditional PCR methods. Two PCR based approaches for detecting large deletions are (a) to design multiple PCR within and flanking the region of the deletion and (b) design a set of PCR assay including ones that spans the entire deletion (both endpoints) as well as each endpoint individually. In (a), an individual that is homozygous or hemizygous for the deletion, the PCR assays within the mutation may fail to amplify while the ones flanking the mutation may amplify. However, this method cannot be used to detect a heterozygote as all PCR assays will amplify. In (b) if the endpoints of the deletion are known it is possible to design a PCR assay that can yield a product that spans the breakpoint of the mutation yielding a chimeric fragment in the presence of the mutation. In the normal allele, this PCR amplification will likely fail due to the large distances involved (many kilobases). However, the normal allele can be detected through the use of assays that span just one endpoint. When the exact endpoints of the deletion are not known it can be much more challenging to design a PCR assay capable of detecting various forms of the deletion reliably. Trial and error must typically be employed in each instance. In one embodiment, the ability to multiplex linked inverted probes can be used to design a series of probes can be created that can detect deletions of any size.

In one embodiment, to detect deletions of any size, one may design a collection of linked inverted probes that spanning various distances from one or both of the farthest known endpoints, in addition to a small number of probes spaced at various intervals to detect the normal allele. Each of the spanning probes may have one end complementary to the non-deleted region. The other end of each distinct probe may be complementary to some region at some variable large distance from non-deleted end. The distance between the probe ends could be too large to extend and amplify using typical approaches, but in the presence of a large deletion, a previously distant binding site for one or more of the probes could be brought to within distance that could be amplified and extended. The resulting product may be detected by an array (detecting presence absence only of an amplified probe) or by sequencing as previously described. Sequencing of the probe may reveal a chimeric fragment of DNA with the two previously flanking DNA sequences now flanking one another. The number of probes required could be determined by the length of the gap that could be extended, amplified, and extended as well as the maximum possible length of the deletion.

LIPs and Sequencing

The use of LIPs followed by sequencing as part of a method for allele calling or ploidy calling for the purpose of prenatal diagnosis may confer a number of unexpected advantages. In some embodiments of the present disclosure, the method involves measuring genetic data for use with an informatics based method, such as PARENTAL SUPPORT™ (PS). The ultimate outcome of some of the embodiments is the actionable genetic data of an embryo or a fetus. The algorithms behind the PS method take the measured genetic data of the target individual, often an embryo or fetus, and the measured genetic data from related individuals, and are able to increase the accuracy with which the genetic state of the target individual is known. In one embodiment, the measured genetic data is used in the context of making ploidy determinations during prenatal genetic diagnosis. In another embodiment the measured genetic data is used in the context of making ploidy determinations or allele calls on embryos during in vitro fertilization. There are many methods that may be used to measure the genetic data of the individual and/or the related individuals in the aforementioned contexts. The different methods comprise a number of steps, those steps often involving amplification of genetic material, addition of oligonucleotide probes, ligation of specified DNA strands, isolation of sets of desired DNA, removal of unwanted components of a reaction, detection of certain sequences of DNA by hybridization, detection of the sequence of one or a plurality of strands of DNA by DNA sequencing methods. In some cases the DNA strands may refer to target genetic material, in some cases they may refer to primers, in some cases they may refer to synthesized sequences, or combinations thereof. These steps may be carried out in a number of different orders. Given the highly variable nature of molecular biology, it is generally not obvious which methods, and which combinations of steps, will perform poorly, well, or best in various situations.

Disclosed herein is a method to overcome the disadvantages of the circularizing probes methods known in the literature. In one embodiment of the present disclosure, the genetic material of the target individual is amplified before circularizing probes are added. In this situation, the small amount of genetic material may be amplified using a wide variety of techniques, for example, multiple displacement amplification or polymerase chain reaction. Other methods of amplification are outlined herein. Once the genetic material from the target individual has been amplified, methods described in the literature that use circularizing probes. Note that the methods known in the art for using circularizing probes involve adding the probes to unamplified, genomic DNA.

For example, after the preamplification step of the target genetic material, the amplified the nucleic acid sequence may be mixed with a probe that can hybridize with two neighboring regions of the target sequence, one on either side. After hybridization, the ends of the probe may be connected by adding a polymerase, a means for ligation, and any necessary reagents to allow the circularization of the probe. After circularization, an exonuclease may be added to digest to non-circularized genetic material, followed by detection of the circularized probe.

The detection of the circularized probe may be done in a number of ways, as described in the literature. For example, it may be isolated, for example by chromatography, it may be amplified, for example by rolling circle amplification, and it may be detected by hybridization, for example using ILLUMINA BEAD ARRAYS or AFFYMETRIX GENECHIP, or it may be sequenced using Sanger sequencing, or a high throughput sequencing platform such as the ILLUMINA SOLEXA GENOME ANALYZER.

In some embodiments the detection of the target genetic material may be done in a multiplexed fashion. The number of genetic target sequences that may be run in parallel can range from one to ten, ten to one hundred, one hundred to one thousand, one thousand to ten thousand, ten thousand to one hundred thousand, one hundred thousand to one million, or one million to ten million.

In some embodiments, this method may be used to genotype a single cell, a small number of cells, two to five cells, six to ten cells, ten to twenty cells, twenty to fifty cell, fifty to one hundred cells, one hundred to one thousand cells, or a small amount of extracellular DNA, for example from one to ten picograms, from ten to one hundred pictograms, from one hundred pictograms to one nanogram, from one to ten nanograms, from ten to one hundred nanograms, or from one hundred nanograms to one microgram.

In one embodiment, the method may be used in the context of in vitro fertilization, where it may be desirable to genotype a single cell blastomere biopsied from a cleavage stage embryo for the purposes of determining the genetic state of the embryo. Or, it may be used to genotype a small number of cells biopsied from the trophectoderm, or from the inner cell mass, of a day 5 embryo, also for the purposes of determining the genetic state of the embryo. In another embodiment, it may be used in the context of non-invasive prenatal diagnosis to genotype isolated single fetal cells found in maternal blood. In another embodiment, in the context of prenatal diagnosis, it may be used to genotype free floating DNA found in maternal blood. In all of these embodiments, the target genetic data that is measured is expected to be actionable, and may be used to make clinical decisions.

Reducing Allele Bias Using Circularizing Probes

One method to target specific locations for sequencing is to synthesize probes in which the 3' and 5' ends of the probes anneal to target DNA at locations adjacent to and on either side of the targeted region, in an inverted manner, such that the addition of DNA polymerase and DNA ligase results in extension from the 3' end, adding bases to single stranded probe that are complementary to the target molecule (gap-fill), followed by ligation of the new 3' end to the 5' end of the original probe resulting in a circular DNA molecule that can be subsequently isolated from background DNA. The probe ends are designed to flank the targeted region of interest. One aspect of this approach is commonly called MIPS and has been used in conjunction with array technologies to determine the nature of the sequence filled in. One drawback to the use of MIPs in the context of measuring allele ratios is that the hybridization, circularization and amplification steps do not happed at equal rates for different alleles at the same loci. This results in measured allele ratios that are not representative of the actual allele ratios present in the original mixture.

In one embodiment of the present disclosure, this approach has been modified to be easily amenable to sequencing as a means of interrogating the filled in sequence. In order to retain the original allelic proportions of the original sample at least one key consideration must be taken into account. The variable positions among different alleles in the gap-fill region must not be too close to the probe binding sites as there can be initiation bias by the DNA polymerase resulting in differential of the variants. Another consideration is that additional variations may be present in the probe binding sites that are correlated to the variants in the gap-fill region which can result unequal amplification from different alleles. In one embodiment of the present disclosure, the 3' ends and 5' ends of the pre-circularized probe are designed to hybridize to bases that are one or a few positions away from the variant positions (polymorphic regions) of the targeted allele. The number of bases between the polymorphic region (SNP or otherwise) and the base to which the 3' end and/or 5' of the pre-circularized probe is designed to hybridize may be one base, it may be two bases, it may be three bases, it may be four bases, it may be five bases, it may be six bases, it may be seven to ten bases, it may be eleven to fifteen bases, or it may be sixteen to twenty bases. The forward and reverse primers may be designed to hybridize a different number of bases away from the polymorphic region. Circularizing probes can be generated in large numbers with current DNA synthesis technology allowing very large numbers of probes to be generated and potentially pooled, enabling interrogation of many loci simultaneously. It has been reported to work with more than 300,000 probes.

Note that this strategy maybe equally well used with PCR primers. In one embodiment, in order to retain the original allelic proportions of the original sample the variable positions among different alleles in the region adjacent to the probe binding site must not be too close to the probe binding sites as there can be initiation bias by the DNA polymerase resulting in differential of the variants. In one embodiment of the present disclosure, the 3' end of the PCR probe is designed to hybridize to bases that are one or a few positions away from the variant positions (polymorphic regions) of the targeted allele. The number of bases between the polymorphic region (SNP or otherwise) and the base to which the 3 end of the PCR probe is designed to hybridize may be one base, it may be two bases, it may be three bases, it may be four bases, it may be five bases, it may be six bases, it may be seven to ten bases, it may be eleven to fifteen bases, or it may be sixteen to twenty bases. The forward and reverse primers may be designed to hybridize a different number of bases away from the polymorphic region.

Targeted Sequencing Using Capture by Hybridization Approaches

Targeting of a specific set of sequences in a target genome can be accomplished in a number of ways. Elsewhere in this document is a description of how LIPs can be used to target a specific set of sequences, but in all of those applications, other targeting methods can be used equally well for the same ends.

One example of another targeting method is the capture by hybridization approach. Some examples of commercial capture by hybridization technologies include AGILENT's SURE SELECT and ILLUMINA's TRUSEQ. In capture by hybridization, a set of oligonucleotides that is complimentary or mostly complimentary to the desired targeted sequences is allowed to hybridize to a mixture of DNA, and then physically separated from the mixture. Once the desired sequences have hybridized to the targeting oligonucleotides, the effect of physically removing the targeting oligonucleotides is to also remove the targeted sequences. Once the hybridized oligos are removed, they can be heated to above their melting temperature and they can be amplified. Some ways to physically remove the targeting oligonucleotides is by covalently bonding the targeting oligos to a solid support, for example a magnetic bead, or a chip. Another way to physically remove the targeting oligonucleotides is by covalently bonding them to a molecular moiety with a strong affinity for another molecular moiety. And example of such a molecular pair is biotin and streptavidin, such as is used in SURE SELECT. Thus that targeted sequences could be covalently attached to a biotin molecule, and after hybridization, a solid support with streptavidin affixed can be used to pull down the biotinylated oligos, to which are hybridized the targeted sequences.

Another method of targeting is hybrid capture. In this method probes that are complementary to the targets of interest are synthesized and then used to hybridize to the target molecules. The hybridized molecules can be separated by various published techniques from the non-hybridized (untargeted) molecules. This probe was originally developed to target and enrich large fractions of the genome with relative uniformity between targets. In this application, it is important that all targets be amplified with enough uniformity that all regions could be detected by sequencing, however, no regard was paid to retaining the proportion of alleles in original sample. Following capture, the alleles present in the sample can be determined by direct sequencing of the captured molecules. The ratios can be evaluated by sequencing through the specific alleles within the targeted region. These sequencing reads can be analyzed and counted according the allele type. However, using the current technology, the measured allele ratios of the captured sequences at a given loci are typically not representative of the original allele ratios.

Probe length, target molecule length, and sequencing read length can all be adjusted to improve the amount of useful enrichment and the uniformly of the enrichment of the different alleles in the original sample In one embodiment, detection of the alleles is performed by sequencing. In order to capture the allele identity at the polymorphic site, it is essential that the sequencing read span the allele in question in order to evaluate the allelic composition of that captured molecule. Since the capture molecules are often of variable lengths upon sequencing cannot be guaranteed to overlap the variant positions unless the entire molecule is sequenced. However, cost considerations as well as technical limitations as to the maximum possible length and accuracy of sequencing reads make sequencing the entire molecule unfeasible. In one embodiment, the read length can be increased from about 30 to about 50 or about 70 bases can greatly increase the number of reads that overlap the variant positions within the targeted sequences.

Another way to increase the number of reads that interrogate the position of interest is to decrease the length of the probe, as long as it does not result in bias in the underlying enriched alleles. The length of the synthesized probe should be long enough such that two probes designed to hybridize to two different alleles found at one locus will hybridize with near equal affinity to the various alleles in the original sample. Currently, methods known in the art describe probes that are longer than 90 bases. However, if the allele is one or a few bases, a probe between 25 and 90 bases is sufficient to ensure equal enrichment from all alleles. When the mixture of DNA that is to be enriched using the hybrid capture technology is a mixture containing free floating DNA isolated from blood, for example maternal blood, the average length of DNA is quite short, typically less than 200 bases. Using shorter probes results in a greater chance that the hybrid capture probes will capture desired DNA fragments. Larger variations may require longer probes. In one embodiment, the variations of interest are one (a SNP) to a few bases in length. In one embodiment, targeted regions in the genome can be preferentially enriched using hybrid capture probes wherein the hybrid capture probes are of a length below 90 bases, and can be as low as 80 bases, as low as 70 bases, as low as 60 bases, as low as 50 bases, as low as 40 bases, as low as 30 bases, or as low as 25 bases. In one embodiment, to increase the chance that the desired allele is sequenced, the length of the probe that is designed to hybridize to the regions flanking the polymorphic allele location can be decreased from above 90 bases, to about 80 bases, or to about 70 bases, or to about 60 bases, or to about 50 bases, or to about 40 bases, or to about 30 bases, or to about 25 bases.

There is a minimum overlap between the synthesized probe and the target molecule in order to enable capture. This synthesized probe can be made as short as possible while still being larger than this minimum required overlap. The effect of using a shorter probe length to target a polymorphic region is that there will be more molecules that overlapping the target allele region. The state of fragmentation of the original DNA molecules also affects the number of reads that will overlap the targeted alleles. Some DNA samples such as plasma samples are already fragmented due to biological processes that take place in vivo. However, samples with longer fragments by benefit from fragmentation prior to sequencing library preparation and enrichment. When both probes and fragments are short (~60-80 bp) maximum specificity may be achieved relatively few sequence reads failing to overlap the critical region of interest.

In one embodiment, the hybridization conditions can be adjusted to maximize uniformity in the capture of different alleles present in the original sample. In one embodiment, hybridization temperatures are decreased to minimize differences in hybridization bias between alleles. Methods known in the art avoid using lower temperatures for hybridization because lowering the temperature has the effect of increasing hybridization of probes to unintended targets. However, when the goal is to preserve allele ratios with maximum fidelity, the approach of using lower hybridization temperatures provides optimally accurate allele ratios, despite the fact that the current art teaches away from this approach. Hybridization temperature can also be increased to require greater overlap between the target and the synthesized probe so that only targets with substantial overlap of the targeted region are captured. In some embodiments of the present disclosure, the hybridization temperature is lowered from the normal hybridization temperature to about 40° C., to about 45° C., to about 50° C., to about 55° C., to about 60° C., to about 65, or to about 70° C.

In one embodiment, the hybrid capture probes can be designed such that the region of the capture probe with DNA that is complementary to the DNA found in regions flanking the polymorphic allele is not immediately adjacent to the DNA that is immediately adjacent to the polymorphic region.

Instead, the capture probe can be designed such that the region of the capture probe that is designed to hybridize to the DNA flanking the polymorphic region of the target is separated from the portion of the capture probe that will be in van der Waals contact with the polymorphic region by a small molecular moiety that is equivalent in length to one or a small number of bases, and which has a binding energy that is roughly independent of the sequence to which is in contact. In one embodiment, the hybrid capture probe is designed to hybridize to a region that is flanking the polymorphic allele but does not cross it; this may be termed a flanking capture probe. The length of the flanking capture probe may be as low as about 120 bases, as low as about 110 bases, as low as about 100 bases, as low as about 90 bases, and can be as low as about 80 bases, as low as about 70 bases, as low as about 60 bases, as low as about 50 bases, as low as about 40 bases, as low as about 30 bases, or as low as about 25 bases.

Targeted Sequencing Using PCR Approaches

In some embodiments, PCR can be used to target specific locations of the genome. In plasma samples, the original DNA is highly fragmented (~100-200 bp, 150 peak). In PCR, both forward and reverse primers must anneal to the same fragment to enable amplification. Therefore, if the fragments are short, the PCR assays must amplify relatively short regions as well. Like MIPS, if the polymorphic positions are too close the polymerase binding site, it could result in biases in the amplification from different alleles. Currently, PCR primers that target polymorphic regions, such as SNPs, are typically designed such that the 3' end of the primer will hybridize to the base immediately adjacent to the polymorphic base or bases. In one embodiment of the present disclosure, the 3' ends of both the forward and reverse PCR primers are designed to hybridize to bases that are one or a few positions away from the variant positions (polymorphic regions) of the targeted allele. The number of bases between the polymorphic region (SNP or otherwise) and the base to which the 3' end of the primer is designed to hybridize may be one base, it may be two bases, it may be three bases, it may be four bases, it may be five bases, it may be six bases, it may be seven to ten bases, it may be eleven to fifteen bases, or it may be sixteen to twenty bases. The forward and reverse primers may be designed to hybridize a different number of bases away from the polymorphic region.

PCR assay can be generated in large numbers, however, the interactions between different PCR assays makes it difficult to multiplex them beyond about one hundred assays. Various complex molecular approaches can be used to increase the level of multiplexing, but it may still be limited to fewer than 1000 assays per reaction. Samples with large quantities of DNA can be split among multiple sub-reactions and then recombined before sequencing. For samples where either the overall sample or some subpopulation of DNA molecules is limited, splitting the sample would introduce statistical noise. In one embodiment, a small or limited quantity of DNA may refer to an amount below 10 pg, between 10 and 100 pg, between 100 pg and 1 ng, between 1 and 10 ng, or between 10 and 100 ng. Note that while this method is particularly useful on small amounts of DNA where other methods that involve splitting into multiple pools can cause significant problems related to introduced stochastic noise, this method still provides the benefit of minimizing bias when it is run on samples of any quantity of DNA. In these situations a pre-amplification step may be used to increase the overall sample quantity. However, this pre-amplification step should not appreciably alter the allelic ratios.

In one embodiment, the method can generate hundreds to thousands of PCR products (can be 10,000 and more), e.g. for genotyping by sequencing or some other genotyping method, from limited samples such as single cells or DNA from body fluids. Currently, performing multiplex PCR reactions of more than 5 to 10 targets presents a major challenge and is often hindered by primer side products, such as primer dimers, and other artifacts. In next generation sequencing the vast majority of the sequencing reads would sequence such artifacts and not the desired target sequences in a sample. In general, to perform targeted sequencing of multiple (n) targets of a sample (greater than 10, 50 or 1000's), one can split the sample into n parallel reactions that amplify one individual target, which is problematic for samples with a limited amount of DNA. This has been performed in PCR multiwell plates or can be done in commercial platforms such as the Fluidigm Access Array (48 reactions per sample in microfluidic chips) or droplet PCR by Rain Dance Technologies (100 s to a few thousands of targets). Described here is a method to effectively amplify many PCR reactions, that is applicable to cases where only a limited amount of DNA is available. In one embodiment, the method may be applied for analysis of single cells, body fluids, biopsies, environmental and/or forensic samples.

Solution:

A) Generate and amplify a library with adaptor sequences on both ends of DNA fragments. Divide into multiple reactions after library amplification.

B) Generate (and possibly amplify) a library with adaptor sequences on both ends of DNA fragments. Perform 1000-plex amplification of selected targets using one target specific "Forward" primer per target and one tag specific primer. One can perform a second amplification from this product using "Reverse" target specific primers and one (or more) primer specific to a universal tag that was introduced as part of the target specific forward primers in the first round.

C) Perform a 1000-plex preamplification of selected target for a limited number of cycles. Divide the product into multiple aliquots and amplify subpools of targets in individual reactions (for example, 50 to 500-plex, though this can be used all the way down to singleplex). Pool products of parallel subpools reactions.

D) During these amplifications primers may carry sequencing compatible tags (partial or full length) such that the products can easily be sequenced.

There is significant diagnostic value in accurately determining the relative proportion of alleles present in a sample. The interpretation of the result depends on the source of the material. In some embodiments of the present disclosure, the allelic ratio information can be used to determine the genetic state of an individual. In some embodiments of the present disclosure, this information can be used to determine the genetic state of a plurality of individuals from one DNA sample, wherein the DNA sample contains DNA from each of the plurality of individuals. In one embodiment, the allelic ratio information can be used to determine copy number of whole chromosomes from individual cells, or bulk samples. In one embodiment, the allelic ratio information can be used to determine copy number of parts, regions, or segments of chromosomes individual cells, or bulk samples. In one embodiment, the allelic ratio information can be used to determine the relative contribution of different cell types in mosaic samples. In one embodiment, the allelic ratio information can be used to determine the fraction of fetal DNA in maternal plasma samples as well as the chromosome copy number of the fetal chromosomes.

Generation of Targeted Sequencing Libraries by PCR of Greater than 100 Targets

We are looking for a protocol that permits the targeted amplification of over a hundred to several thousand or more target sequences (e.g. SNP loci) from genomic DNA obtained from plasma. The amplified sample should be free of primer dimer products and be preferably unbiased between alleles and target loci. If during or after amplification the products are appended with sequencing compatible adaptors, analysis of these products can be performed by next-gen sequencing.

The initial solution to the problem of amplifying e.g. 5000 SNPs is to perform one 5000-plex PCR amplification of the total plasma DNA sample. However, experience shows that such high multiplexing (1042-plex was attempted in house) leads to the generation of primer dimer products that are far in excess of the desired amplification products. These can be reduced empirically by eliminating primers that form these mischief products and by performing in silico selection of primers. However, the larger the number of assays, the more insurmountable this problem becomes.

One solution is to split the 5000-plex reaction into several lower-plexed amplifications, e.g. one hundred 50-plex or fifty 100-plex reactions. However, if the sample DNA is limited, such as in non-invasive prenatal diagnostics from pregnancy plasma, dividing the sample between multiple reactions should be avoided. Note that this approach could be used to perform targeted amplification in a manner that would result in low amounts of allelic bias for 50-500 loci, for 500 to 5,000 loci, for 5,000 to 50,000 loci, or even for 50,000 to 500,000 loci.

Described herein is a method to first globally amplify the plasma DNA of a sample and then divide the sample up into multiple multiplexed target enrichment reactions with moderate target sequences per reaction. In one embodiment, the method can be used for preferentially enriching a DNA mixture at a plurality of loci, the method comprising generating and amplifying a library from a mixture of DNA where the molecules in the library have adaptor sequences ligated on both ends of the DNA fragments, dividing the amplified library into multiple reactions, performing a first round of multiplex amplification of selected targets using one target specific "forward" primer per target and one or a plurality of adaptor specific universal "reverse" primers. In one embodiment, the method may further comprise performing a second amplification using "reverse" target specific primers and one or a plurality of primers specific to a universal tag that was introduced as part of the target specific forward primers in the first round. In one embodiment, the method may be used for preferentially enriching a DNA mixture at a plurality of loci, the method comprising performing a multiplex preamplification of selected targets for a limited number of cycles, dividing the product into multiple aliquots and amplifying sub-pools of targets in individual reactions, and pooling products of parallel subpools reactions. In one embodiment, the primers carry partial or full length sequencing compatible tags.

Workflow:
1. Extract plasma DNA
2. Prepare fragment library with universal adaptors on both ends of fragments.
3. Amplify library using universal primers specific to the adaptors.
4. Divide the amplified sample "library" into multiple aliquots. Perform multiplex (e.g. 100-plex, or 1000-plex with one target specific primer per target and a tag-specific primer) amplifications on aliquots.
5. Pool aliquots of one sample.
6. Barcode sample if not already done.
7. Mix samples, adjust concentration.
8. Perform sequencing.

The workflow may contain multiple sub-steps that comprise one of the listed steps (e.g. step 2. Library preparation may comprise 3 enzymatic steps (blunt ending, dA tailing and adaptor ligation) and 3 purification steps).

Steps of the workflow may be combined, divided up or performed in different order (e.g. bar coding and pooling of samples).

It is important to note that the amplification of a library can be performed in such a way that it is biased to amplify short fragments more efficiently. In this manner it is possible to preferentially amplify shorter sequences, e.g. mono-nucleo-somal DNA fragments as the cell free fetal DNA (of placental origin) found in the circulation of pregnant women.

PCR Assays:
  Can have the tags for sequencing (usually a truncated form of 15-25 bases). After multiplexing, PCR multiplexes of a sample are pooled and then the tags are completed (including bar coding) by a tag-specific PCR (could also be done by ligation).
  The full sequencing tags can be added in the same reaction as the multiplexing. In the first cycles targets are amplified with the target specific primers, subsequently the tag-specific primers take over to complete the SQ-adaptor sequence.
  The PCR primers carry no tags. After m.p. PCR the sequencing tags are appended to the amplification products by ligation.

Sequencing Results:
  The 12 samples were pooled at equal volumes
  Pool cleaned into 100 ul Elution buffer
  Pool diluted to 30 nM (was 75 nM)
  Sent for sequencing
  QC by qPCR Preparation of 15 Cy Replicates
(Orange: 8 Replicates with Barcodes 5 to 12)
  15 Cycles STA
    (RED STA protocol: 95C×10 min; 95C×15 s, 65C×1 min, 60C×4 min, 65C×30 s, 72C×30 s; 72C×2 min)
  Used the 50 nM primers reactions
  Performed a first ExoSAP straight from product→failed to remove all primers (Bioanalyzer): just leave this step out in the future.
  Dilute 1/10 (adding 90 ul H2O)
  2 ul in 14 ul ExoSAP reaction→dilute to 50 ul=1/25 dilution in this step=total 1/250
  Append SQ tags (longer, full F-SQ and R-m.p. adaptor without barcodes):
    1 ul DNA in 10 ul PCR: F-SQ×R-SQ-m.p.; concentrations: 200 nM?
    15 cycles: 95C×10 min; 95C×15 s, 60C×30 s, 65C×15 s, 72C×30 s; 72C×2 min
    Add 90 ul H2O, use 1 ul for next step, primer carry over will be 1/100 of conc in this reaction
  Barcoding PCR (p. 9 quick book):
    1 ul DNA in 10 ul PCR: F-SQ×R-SQ-BC1 to 12-lib.; concentrations: 1 uM
    15 cycles: 95C×10 min; 95C×15 s, 60C×15 s, 72C×30 s; 72C×2 min
    Add 40 ul H2O
→check 1 ul on Bioanalyzer DNA1000 chip→pool samples→clean up→Bioanalyzer, adjust conc→sequencing
Prep of 30 cy Replicate (Yellow: 1 Replicates with Barcode 4 into Sequencing)
  30 Cycles STA
    (Yellow STA protocol: 95C×10 min; 95C×15 s, 65C×1 min, 60C×4 min, 65C×30 s, 72C×30 s; 72C×2 min)
    Used the 50 nM primers reactions
    Performed a first ExoSAP straight from product→failed to remove all primers (Bioanalyzer): just leave this step out in the future.
    Dilute 1/10 (adding 90 ul H2O)
    Dilute 1/100→1/25 dilution=total 1/25,000
    Probably did not perform ExoSAP clean up, small uncertainty from notes
    Append SQ Tags (Longer, Full F-SQ and R-m.p. Adaptor without Barcodes):
    1 ul DNA in 10 ul PCR: F-SQ×R-SQ-m.p.; concentrations: 200 nM?
    15 cycles: 95C×10 min; 95C×15 s, 60C×30 s, 65C×15 s, 72C×30 s; 72C×2 min
    Add 90 ul H2O, use 1 ul for next step, primer carry over will be 1/100 of conc in this reaction
    Barcoding PCR (p. 9 Quick Book):
    1 ul DNA in 10 ul PCR: F-SQ×R-SQ-BC1 to 12-lib.; concentrations: 1 uM
    15 cycles: 95C×10 min; 95C×15 s, 60C×15 s, 72C×30 s; 72C×2 min
    Add 40 ul H2O
→check 1 ul on Bioanalyzer DNA1000 chip→pool samples→clean up→Bioanalyzer, adjust conc→sequencing
Prep of 1000-Plex Reactions
(Blue: 1000-Plex; from Amplified SQ Libraries (p. 32 Lab Book BZ1))
    BC2=ASQ8=pregnancy plasma 2666 or 2687; BC3=ASQ4=apo sup 16777
    15 Cycles STA
    (RED STA protocol: 95C×10 min; 95C×15 s, 65C×1 min, 60C×4 min, 65C×30 s, 72C×30 s; 72C×2 min)
    50 nM target specific tagged R-primers and 200 nM F-SQ-primer
    Performed a first ExoSAP straight from product→failed to remove all primers (Bioanalyzer): just leave this step out in the future.
    Dilute 1/5 (adding 40 ul H2O)
    2 ul in 14 ul ExoSAP reaction→dilute to 100 ul=1/50 dilution in this step=total 1/250
    Append SQ Tags (Longer, Full F-SQ and R-m.p. Adaptor without Barcodes):
    1 ul DNA in 10 ul PCR: F-SQ×R-SQ-m.p.; concentrations: 200 nM?
    15 cycles: 95C×10 min; 95C×15 s, 60C×30 s, 65C×15 s, 72C×30 s; 72C×2 min
    Add 90 ul H2O, use 1 ul for next step, primer carry over will be 1/100 of conc in this reaction
    Barcoding PCR (p. 9 Quick Book):
    1 ul DNA in 10 ul PCR: F-SQ×R-SQ-BC1 to 12-lib.; concentrations: 1 uM
    15 cycles: 95C×10 min; 95C×15 s, 60C×15 s, 72C×30 s; 72C×2 min
    Add 40 ul H2O
→check 1 ul on Bioanalyzer DNA1000 chip→pool samples→clean up→Bioanalyzer, adjust conc→sequencing
Compositions of DNA When performing an informatics analysis on sequencing data measured on a mixture of fetal and maternal blood to determine genomic information pertaining to the fetus, for example the ploidy state of the fetus, it may be advantageous to measure the allele ratios at certain alleles. Unfortunately, in many cases, such as when attempting to determine the ploidy state of a fetus from the DNA mixture found in the plasma of a maternal blood sample, the amount of DNA available is not sufficient to directly measure the allele ratios in the mixture. In these cases, amplification of the DNA mixture will provide sufficient numbers of DNA molecules that the desired allele ratios may be measured. However, current methods of amplification typically used in the amplification of DNA for sequencing are often very biased, meaning that they do not amplify both alleles at a polymorphic locus by the same amount. A biased amplification can result in allele ratios that are quite different from the allele ratios in the original mixture. Conventional methods do not use statistical measurements of allele ratios at a large number of polymorphic loci. In contrast, in an embodiment of the present disclosure, amplification or enrichment methods that specifically enrich polymorphic alleles and preserve allelic ratios is advantageous.

A number of methods are described herein that may be used to preferentially enrich a sample of DNA at a plurality of loci in a way that minimizes allelic bias. Some examples are using circularizing probes to target a plurality of loci where the 3' ends and 5' ends of the pre-circularized probe are designed to hybridize to bases that are one or a few positions away from the polymorphic regions of the targeted allele. Another is to use PCR probes where the 3' end PCR probe is designed to hybridize to bases that are one or a few positions away from the polymorphic regions of the targeted allele. Another is to use a split and pool approach to create mixtures of DNA where the preferentially enriched loci are enriched with low allelic bias without the drawbacks of direct multiplexing. Another is to use a hybrid capture approach where the capture probes are designed such that the region of the capture probe that is designed to hybridize to the DNA flanking the polymorphic region of the target is separated from the polymorphic region by one or a small number of bases.

In the case where allelic ratio measurements at polymorphic loci are used to determine the ploidy state of an individual, it is desirable to preserve the ratio of alleles in a sample of DNA as it is prepared for genetic measurements. This preparation may involve WGA amplification, targeted amplification, selective enrichment techniques, hybrid capture techniques, circularizing probes or other methods meant to amplify the amount of DNA and/or selectively enhance the presence of molecules of DNA that correspond to certain alleles.

In some embodiments of the present disclosure, there is a set of DNA probes designed to target loci where the loci have maximal minor allele frequencies. In some embodiments of the present disclosure, there is a set of probes that are designed to target where the loci have the maximum likelihood of the fetus having a highly informative SNP at that loci. In some embodiments of the present disclosure, there is a set of probes that are designed to target loci where the probes are optimized for a given population subgroup. In some embodiments of the present disclosure, there is a set of probes that are designed to target loci where the probes are optimized for a given mix of population subgroups. In some embodiments of the present disclosure, there is a set of probes that are designed to target loci where the probes are optimized for a given pair of parents which are from different population subgroups that have different minor allele frequency profiles. In some embodiments of the present disclosure, there is a circularized strand of DNA that contains at least one basepair that annealed to a piece of DNA that is of fetal origin. In some embodiments of the present disclosure, there is a circularized strand of DNA that contains at least one basepair that annealed to a piece of DNA that is of placental origin. In some embodiments of the present disclosure, there is a circularized strand of DNA that circularized while at least some of the nucleotides were annealed to DNA that was of fetal origin. In some embodiments of the present disclosure, there is a circularized strand of DNA that circularized while at least some of the nucleotides were annealed to DNA that was of placental origin. In some embodiments of the present disclosure, there is a set of probes wherein some of the probes target single tandem repeats, and some of the probes target single nucleotide polymorphisms. In some embodiments, the loci are selected for the purpose of non-invasive prenatal diagnosis. In some embodiments, the probes are used for the purpose of non-invasive prenatal diagnosis. In some embodiments, the loci are targeted using a method that could include circularizing probes, MIPs, capture by hybridization probes, probes on a SNP array, or combinations thereof. In some embodiments, the probes are used as circularizing probes, MIPs, capture by hybridization probes, probes on a SNP array, or combinations thereof. In some embodiments, the loci are sequenced for the purpose of non-invasive prenatal diagnosis.

In the case where the relative informativeness of a sequence is greater when combined with relevant parent contexts, it follows that maximizing the number of sequence reads that contain a SNP for which the parental context is known may maximize the informativeness of the set of sequencing reads on the mixed sample. In one embodiment the number of sequence reads that contain a SNP for which the parent contexts are known may be enhanced by using qPCR to preferentially amplify specific sequences. In one embodiment the number of sequence reads that contain a SNP for which the parent contexts are known may be enhanced by using circularizing probes (for example, MIPs) to preferentially amplify specific sequences. In one embodiment the number of sequence reads that contain a SNP for which the parent contexts are known may be enhanced by using a capture by hybridization method (for example SURESELECT) to preferentially amplify specific sequences. Different methods may be used to enhance the number of sequence reads that contain a SNP for which the parent contexts are known. In one embodiment of the present disclosure, the targeting may be accomplished by extension ligation, ligation without extension, capture by hybridization, or PCR.

In a sample of fragmented genomic DNA, a fraction of the DNA sequences map uniquely to individual chromosomes; other DNA sequences may be found on different chromosomes. Note that DNA found in plasma, whether maternal or fetal in origin is typically fragmented, often at lengths under 500 bp. In a typical genomic sample, roughly 3.3% of the mappable sequences will map to chromosome 13; 2.2% of the mappable sequences will map to chromosome 18; 1.35% of the mappable sequences will map to chromosome 21; 4.5% of the mappable sequences will map to chromosome X in a female; 2.25% of the mappable sequences will map to chromosome X (in a male); and 0.73% of the mappable sequences will map to chromosome Y (in a male). These are the chromosomes that are most likely to be aneuploid in a fetus. Also, among short sequences, approximately 1 in 20 sequences will contain a SNP, using the SNPs contained on dbSNP. The proportion may well be higher given that there may be many SNPs that have not been discovered.

In one embodiment of the present disclosure, targeting methods may be used to enhance the fraction of DNA in a sample of DNA that map to a given chromosome such that the fraction significantly exceeds the percentages listed above that are typical for genomic samples. In one embodiment of the present disclosure, targeting methods may be used to enhance the fraction of DNA in a sample of DNA such that the percentage of sequences that contain a SNP are significantly greater than what may be found in typical for genomic samples. In one embodiment of the present disclosure, targeting methods may be used to target DNA from a chromosome or from a set of SNPs in a mixture of maternal and fetal DNA for the purposes of prenatal diagnosis.

Note that a method has been reported (U.S. Pat. No. 7,888,017) for determining fetal aneuploidy by counting the number of reads that map to a suspect chromosome and comparing it to the number of reads that map to a reference chromosome, and using the assumption that an over abundance of reads on the suspect chromosome corresponds to a triploidy in the fetus at that chromosome. Those methods for prenatal diagnosis would not make use of targeting of any sort, nor do they describe the use of targeting for prenatal diagnosis.

By making use of targeting approaches in sequencing the mixed sample, it may be possible to achieve a certain level of accuracy with fewer sequence reads. The accuracy may refer to sensitivity, it may refer to specificity, or it may refer to some combination thereof. The desired level of accuracy may be between 90% and 95%; it may be between 95% and 98%; it may be between 98% and 99%; it may be between 99% and 99.5%; it may be between 99.5% and 99.9%; it may be between 99.9% and 99.99%; it may be between 99.99% and 99.999%, it may be between 99.999% and 100%. Levels of accuracy above 95% may be referred to as high accuracy.

There are a number of published methods in the prior art that demonstrate how one may determine the ploidy state of a fetus from a mixed sample of maternal and fetal DNA, for example: G. J. W. Liao et al. Clinical Chemistry 2011; 57(1) pp. 92-101. These methods target thousands of locations along each chromosome. The number of locations along a chromosome that may be targeted while still resulting in a high accuracy ploidy determination on a fetus, for a given number of sequence reads, from a mixed sample of DNA is unexpectedly low. In one embodiment of the present disclosure, an accurate ploidy determination may be made by using targeted sequencing, using any method of targeting, for example qPCR, capture by hybridization, or circularizing probes, wherein the number of loci along a chromosome that need to be targeted may be between 1,000 and 500 loci; it may be between 500 and 300 loci; it may be between 300 and 200 loci; it may be between 200 and 150 loci; it may be between 150 and 100 loci; it may be between 100 and 50 loci; it may be between 50 and 20 loci; it may be between 20 and 10 loci. Optimally, it may be between 100 and 500 loci. The high level of accuracy may be achieved by targeting a small number of loci and executing an unexpectedly small number of sequence reads. The number of reads may be between 5 million and 2 million reads; the number of reads may be between 2 million and 1 million; the number of reads may be between 1 million and 500,000; the number of reads may be between 500,000 and 200,000; the number of reads may be between 200,000 and 100,000; the number of reads may be between 100,000 and 50,000; the number of reads may be between 50,000 and 20,000; the number of reads may be between 20,000 and 10,000; the number of reads may be below 10,000.

In some embodiments, there is a composition comprising a mixture of DNA of fetal origin, and DNA of maternal origin, wherein the percent of sequences that uniquely map to chromosome 13 is greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome 18 is greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome 21 is greater than 2%, greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome X is greater than 6%, greater than 7%, greater than 8%, greater than 9%, greater than 10%, greater than 12%, greater than 15%, greater than 20%, greater than 25%, or greater than 30%. In some embodiments of the present disclosure, there is a composition comprising a mixture of DNA of fetal origin, and DNA of maternal origin, wherein the percent of sequences that uniquely map to chromosome Y is greater than 1%, greater than 2%, greater than 3%, greater than 4%, greater than 5%, greater than 6%, greater than 7%, greater than 8%, greater than 9%, greater than 10%, greater than 12%, greater than 15%, greater than 20%, greater than 25%, or greater than 30%.

In some embodiments, there is a composition comprising a mixture of DNA of fetal origin, and DNA of maternal origin, wherein the percent of sequences that uniquely map to a chromosome, that contains at least one single nucleotide polymorphism is greater than 0.2%, greater than 0.3%, greater than 0.4%, greater than 0.5%, greater than 0.6%, greater than 0.7%, greater than 0.8%, greater than 0.9%, greater than 1%, greater than 1.2%, greater than 1.4%, greater than 1.6%, greater than 1.8%, greater than 2%, greater than 2.5%, greater than 3%, greater than 4%, greater than 5%, greater than 6%, greater than 7%, greater than 8%, greater than 9%, greater than 10%, greater than 12%, greater than 15%, or greater than 20%, and where the chromosome is taken from the group 13, 18, 21, X, or Y. In some embodiments of the present disclosure, there is a composition comprising a mixture of DNA of fetal origin, and DNA of maternal origin, wherein the percent of sequences that uniquely map to a chromosome and that contain at least one single nucleotide polymorphism from a set of single nucleotide polymorphisms is greater than 0.15%, greater than 0.2%, greater than 0.3%, greater than 0.4%, greater than 0.5%, greater than 0.6%, greater than 0.7%, greater than 0.8%, greater than 0.9%, greater than 1%, greater than 1.2%, greater than 1.4%, greater than 1.6%, greater than 1.8%, greater than 2%, greater than 2.5%, greater than 3%, greater than 4%, greater than 5%, greater than 6%, greater than 7%, greater than 8%, greater than 9%, greater than 10%, greater than 12%, greater than 15%, or greater than 20%, where the chromosome is taken from the set of chromosome 13, 18, 21, X and Y, and where the number of single nucleotide polymorphisms in the set of single nucleotide polymorphisms is between 1 and 10, between 10 and 20, between 20 and 50, between 50 and 100, between 100 and 200, between 200 and 500, between 500 and 1,000, between 1,000 and 2,000, between 2,000 and 5,000, between 5,000 and 10,000, between 10,000 and 20,000, between 20,000 and 50,000, and between 50,000 and 100,000.

In theory, each cycle in the amplification doubles the amount of DNA present, however, in reality, the degree of amplification is slightly lower than two. In theory, amplification, including targeted amplification, will result in bias free amplification of a DNA mixture. When DNA is amplified, the degree of allelic bias typically increases with the number of amplification steps. In some embodiments, the methods described herein involve amplifying DNA with a low level of allelic bias. Since the allelic bias compounds, one can determine the per cycle allelic bias by calculating the nth root of the overall bias where n is the base 2 logarithm of degree of enrichment. In some embodiments, there is a composition comprising a second mixture of DNA, where the second mixture of DNA has been preferentially enriched at a plurality of polymorphic loci from a first mixture of DNA where the degree of enrichment is at least 10, at least 100, at least 1,000, at least 10,000, at least 100,000 or at least 1,000,000, and where the ratio of the alleles in the second mixture of DNA at each locus differs from the ratio of the alleles at that locus in the first mixture of DNA by a factor that is, on average, less than 1,000%, 500%, 200%, 100%, 50%, 20%, 10%, 5%, 2%, 1%, 0.5%, 0.2%, 0.1%, 0.05%, 0.02%, or 0.01%. In some embodiments, there is a composition comprising a second mixture of DNA, where the second mixture of DNA has been preferentially enriched at a plurality of polymorphic loci from a first mixture of DNA where the per cycle allelic bias for the plurality of polymorphic loci is, on average, less than 10%, 5%, 2%, 1%, 0.5%, 0.2%, 0.1%, 0.05%, or 0.02%. In some embodiments, the plurality of polymorphic loci comprises at least 10 loci, at least 20 loci, at least 50 loci, at least 100 loci, at least 200 loci, at least 500 loci, at least 1,000 loci, at least 2,000 loci, at least 5,000 loci, at least 10,000 loci, at least 20,000 loci, or at least 50,000 loci.

Allele Distributions

In one embodiment, the goal of the method is to detect fetal copy number based on a maternal blood sample which contains some free-floating fetal DNA. In some embodiments, the fraction of fetal DNA compared to the mother's DNA is unknown. The combination of a targeting method, such as LIPs, followed by sequencing results in a platform response that consists of the count of observed sequences associated with each allele at each SNP. The set of possible alleles, either A/T or C/G, is known at each SNP. Without loss of generality, the first allele will be labeled A and the second allele will be labeled B. Thus, the measurement at each SNP consists of the number of A sequences ($N_A$) and the number of B sequences ($N_B$). These will be transformed for the purpose of future calculations into the total sequence count (n) and the ratio of A alleles to total (r). The sequence count for a single SNP will be referred to as the depth of read. The fundamental principal which allows copy number identification from this data is that the ratio of A and B sequences will reflect the ratio of A and B alleles present in the DNA being measured.

$$n = N_A + N_B$$

$$r = N_A / (N_A + N_B)$$

Measurements will be initially aggregated over SNPs from the same parent context based on unordered parent genotypes. Each context is defined by the mother genotype and the father genotype, for a total of 9 contexts. For example, all SNPs where the mother's genotype is AA and the father's genotype is BB are members of the AA|BB context. The A allele is defined as present at ratio $r_m$ in the mother genotype and ratio $r_f$ in the father genotype. For example, the allele A is present at ratio $r_m=1$ where the mother is AA and ratio $r_f=0.5$ where the father is AB. Thus, each context defines values for $r_m$ and $r_f$. Although the child genotypes cannot always be predicted from the parent genotypes, the allele ratio averaged over a large number of SNPs can be predicted based on the assumption that a parent AB genotype will contribute A and B at equal rates.

Consider a copy number hypothesis for the child of the form $(n_m, n_f)$ where $n_m$ is the number of mother copies and $n_f$ is the number of father copies of the chromosome. The expected allele ratio $r_c$ in the child (averaged over SNPs in a particular parent context) depends on the allele ratios of the parent contexts and the parent copy numbers.

$$r_c = \frac{n_m r_m + n_f r_f}{n_m + n_f} \quad (1)$$

In a mixture of maternal and fetal blood, allele copies will be contributed from both the mother directly and from the child. Assume that the fraction of child DNA present in the mixture is $\delta$. Then in the mixture, the ratio r of the A allele in a given context is a linear combination of the mother ratio $r_m$ and the child ratio $r_c$, which can be reduced to a linear combination of the mother ratio and father ratio using equation 1.

$$r = (1-\delta)r_m + \delta r_c \quad (2)$$
$$= \left(1 - \frac{\delta n_f}{n_m + n_f}\right)r_m + \frac{\delta n_f}{n_m + n_f}r_f$$

Equation 2 predicts the expected ratio of A alleles for SNPs in a given context as a function of the copy number hypothesis $(n_m, n_f)$. Note that the allele ratio on individual SNPs is not predicted by this equation because these depend on random assignment where at least one parent is heterozygous. Therefore, the set of sequences from all SNPs in a particular context will be combined. Assuming that the context contains m SNPs, and recalling that n sequences will be produced from each SNP, the data from that context consists of N=mn sequences. Each of the N sequences is considered an independent random trial where the theoretical rate of A sequences is the allele ratio r. The measured rate of A sequences $\hat{r}$ is therefore known to be Gaussian distributed with mean r and variance $\sigma^2 = r(1-r)/N$.

Recall that the theoretical allele ratio is a function of the parent copy numbers $(n_m, n_f)$. Thus, each hypothesis h results in a predicted allele ratio $r_i^h$ for the SNP in parent context i. The data likelihood is defined as the probability of a given hypothesis producing the observed data. Thus, the likelihood of measurement $r_i^h$ from context i under hypothesis h is a binomial distribution, which can be approximated for large N as a Gaussian distribution with the following mean and variance. The mean is determined by the context and the hypothesis as described in equation 2.

$$p(\hat{r}_i | h) = N(\hat{r}_i; \mu, \sigma)$$
$$\mu = r_i^h$$
$$\sigma = \sqrt{\frac{r_i^h(1-r_i^h)}{N_i}}$$

The measurements on each of the nine contexts are assumed independent given the parent copy numbers, due to the common assumption of independent noise on each SNP. Thus, the data from a particular chromosome consists of the sequence measurements from contexts i ranging from 1 to 9. The likelihood of the observed allele ratios $\{\hat{r}_1 \ldots, \hat{r}_9\}$ from the whole chromosome is therefore the product of the individual context likelihoods:

$$p(\hat{r}_1 \ldots, \hat{r}_9) = \prod_{i=1}^{9} p(\hat{r}_i | h)$$
$$= \prod_{i=1}^{9} N\left(\hat{r}_i; r_i^h, \sqrt{\frac{r_i^h(1-r_i^h)}{N_i}}\right)$$

Parameter Estimation

Equation 2 predicts the allele ratio as a function of parent copy number hypothesis, but also includes the fraction of child DNA. Therefore, the data likelihood for each chromosome is a function of through its effect on $r_i^h$. This effect is highlighted through the notation $p(\hat{r}_1 \ldots, \hat{r}_9 | h; \delta)$. This parameter cannot be predicted with high accuracy, and therefore must be estimated from the data. A number of different approaches may be used for parameter estimation. One method involves the measurement of chromosomes for which copy number errors are not viable at the stage of development where testing will be performed. The other method measures only chromosomes on which errors are expected to occur.

Measure Some Chromosomes Known to be Disomy

In this method, certain chromosomes will be measured which cannot have copy number errors at the state of development when testing is performed. These chromosomes will be referred to as the training set T. The copy number hypothesis on these chromosomes is (1,1). Assuming that each chromosome is independent, the data likelihood of the measurements from all chromosomes t in T is the product of the individual chromosome likelihoods. The child fraction $\delta$ can be selected to maximize the data likelihood across the chromosomes in T conditioned on the disomy hypothesis. Let $R_t$ represent the set of measurements $\hat{r}_i$ from all contexts i on chromosome t. Then, the maximum likelihood estimate $\delta^*$ solves the following:

$$\delta^* = \operatorname{argmin}_\delta \prod_{t \in T} p(R_t | h = (1,1); \delta)$$

This optimization has only one degree of freedom constrained between zero and one, and therefore can easily be solved using a variety of numerical methods. The solution $\delta^*$ can then be substituted into equation 2 in order to calculate the likelihoods of each hypothesis on each chromosome.

Measure Only Chromosomes which May have Copy Number Errors

If copy number errors are possible on all of the chromosomes being measured, the child concentration must be estimated in parallel with the copy number hypotheses. Note that the same copy number error present on all measured chromosomes will be very difficult to detect. For example, maternal trisomy on all chromosomes at a given child concentration will result in the same theoretical allele ratios as disomy on all chromosomes at lower child concentration, because in both cases the contribution of mother alleles compared to father alleles increases uniformly across all chromosomes and contexts.

A straight forward approach for classification of a limited set of chromosomes t is to consider the joint chromosome hypothesis H, which consists of the joint set of hypotheses for all chromosomes being tested. If the chromosome hypotheses consist of disomy, maternal trisomy and paternal trisomy, the number of possible joint hypotheses is $3^T$ where T is the number of tested chromosomes. A maximum likelihood estimate $\delta^*(H)$ can be calculated conditioned on each joint hypothesis. The likelihood of the joint hypothesis is thus calculated as follows:

$$\delta^*(H) = \operatorname{argmax}_\delta \Pi_{i=1}^T p(R_i|H;\delta)$$

$$p(\text{all data}|H) = \Pi_{i=1}^T p(R_i|H;\delta^*(H))$$

The joint hypothesis likelihoods p(all data|H) can be calculated for each joint hypothesis H, and the maximum likelihood hypothesis is selected, with its corresponding estimate $\delta^*(H)$ of the child fraction.

Performance Specifications

The ability to distinguish between parent copy number hypotheses is determined by models discussed in the previous section. At the most general level, the difference in expected allele ratios under the different hypotheses must be large compared to the standard deviations of the measurements. Consider the example of distinguishing between disomy and maternal trisomy, or hypotheses $h_1=(1,1)$ and $h_2=(2,1)$. Hypothesis 1 predicts allele ratio $r^1$ and hypothesis 2 predictions allele ratio $r^2$, as a function of the mother allele ratio $r_m$ and father allele ratio $r_f$ for the context under consideration.

$$r^1 = \left(1 - \frac{\delta}{2}\right)r_m + \frac{\delta}{2}r_f$$

$$r^2 = \left(1 - \frac{\delta}{3}\right)r_m + \frac{\delta}{3}r_f$$

The measured allele ratio $\hat{r}$ is predicted to be Gaussian distributed, either with mean $r^1$ or mean $r^2$, depending on whether hypothesis 1 or 2 is true. The standard deviation of the measured allele ratio depends similarly on the hypothesis, according to equation 3. In a scenario where one can expect to identify either hypothesis 1 or 2 as truth based on the measurement $\hat{r}$, the means $r^1$, $r^2$ and standard deviations $\sigma^1$, $\sigma^2$ must satisfy a relationship such as the following, which guarantees that the means are far apart compared to the standard deviations. This criterion represents a 2 percent error rate, meaning a 2 percent chance of either false negative or false positive.

$$|r^1 - r^2| > 2\sigma^1 + 2\sigma^2$$

Substituting the copy numbers for disomy (1, 1) and maternal trisomy (2, 1) for hypotheses 1 and 2 results in the following condition:

$$\left|\frac{\delta}{6}(r_f - r_m)\right| > 2\sigma_1 + 2\sigma_2$$

$$\sigma^1 = \sqrt{\frac{r_1(1-r^1)}{N}}$$

-continued $$\sigma^2 = \sqrt{\frac{r_2(1-r^2)}{N}}$$

$$\sigma^2 = \sqrt{\frac{r_2(1-r^2)}{N}}$$

FIG. 1 shows the required number of measurements (number of SNPs multiplied by depth of read) versus child concentration required to satisfy the previous condition. Two different parent contexts are shown. In practice, measurements from multiple contexts may be combined, resulting in a smaller number of required measurements per context.

Overview of the Analysis Method

In one embodiment of the present disclosure, using the parent contexts, and chromosomes known to be euploid, it is possible to estimate, by a set of simultaneous equations, the proportion of DNA in the maternal blood from the mother and the proportion of DNA in the maternal blood from the fetus. These simultaneous equations are made possible by the knowledge of the alleles present on the father. In particular, alleles present on the father and not present on the mother provide a direct measurement of fetal DNA. One may then look at the particular chromosomes of interest, such as chromosome 21, and see whether the measurements on this chromosome under each parental context are consistent with a particular hypothesis, such as $H_{mp}$ where m represents the number of maternal chromosomes and p represents the number of paternal chromosomes e.g. $H_{11}$ representing euploid, $H_{21}$ and $H_{12}$ representing maternal and paternal trisomy respectively.

It is important to note that this method does not use a reference chromosome as a basis by which to compare observed allelic ratios on the chromosome of interest.

This disclosure presents a method by which one may determine the ploidy state of a gestating fetus, at one or more chromosome, in a non-invasive manner, using genetic information determined from fetal DNA found in maternal blood. The fetal DNA may be purified, partially purified, or not purified; genetic measurements may be made on DNA that originated from more than one individual. Informatics type methods can infer genetic information of the target individual, such as the ploidy state, from the bulk genotypic measurements at a set of alleles. The set of alleles may contain various subsets of alleles, wherein one or more subsets may correspond to alleles that are found on the target individual but not found on the non-target individuals, and one or more other subsets may correspond to alleles that are found on the non-target individual and are not found on the target individual. The method may involve using comparing ratios of measured output intensities for various subsets of alleles to expected ratios given various potential ploidy states. The platform response may be determined, and a correction for the bias of the system may be incorporated into the method.

Key Assumptions of the Method:
  The expected amount of genetic material in the maternal blood from the mother is constant across all loci.
  The expected amount of genetic material present in the maternal blood from the fetus is constant across all loci assuming the chromosomes are euploid.
  The chromosomes that are non-viable (all excluding 13, 18, 21, X, Y) are all euploid in the fetus. In one embodiment, only some of the non-viable chromosomes need be euploid on the fetus.

General Problem Formulation:

One may write $y_{ijk} = g_{ijk}(x_{ijk}) + v_{ijk}$ where $x_{ijk}$ is the quantity of DNA on the allele k=1 or 2 (1 represents allele A and 2 represents allele B), j=1 ... 23 denotes chromosome number and i=1 ... N denotes the locus number on the chromosome, $g_{ijk}$ is platform response for particular locus and allele ijk, and $v_{ijk}$ is independent noise on the measurement for that locus and allele. The amount of genetic material is given by $x_{ijk} = am_{ijk} + \Delta c_{ijk}$ where a is the amplification factor (or net effect of leakage, diffusion, amplification etc.) of the genetic material present on each of the maternal chromosomes, $m_{ijk}$ (either 0, 1, 2) is the copy number of the particular allele on the maternal chromosomes, $\Delta$ is the amplification factor of the genetic material present on each of the child chromosomes, and $c_{ijk}$ is the copy number (either 0, 1, 2, 3) of the particular allele on the child chromosomes. Note that for the first simplified explanation, a and $\Delta$ are assumed to be independent of locus and allele i.e. independent of i, j, and k. This gives:

$$y_{ijk} = g_{ijk}(am_{ijk} + \Delta c_{ijk}) + v_{ijk}$$

Approach Using an Affine Model that is Uniform Across all Loci:

One may model g with an affine model, and for simplicity assume that the model is the same for each locus and allele, although it will be understood after reading this disclosure how to modify the approach when the affine model is dependent on i,j,k. Assume the platform response model is $$g_{ijk}(x_{ijk}) = b + am_{ijk} + \Delta c_{ijk}$$

where amplification factors a and $\Delta$ have been used without loss of generality, and a y-axis intercept b has been added which defines the noise level when there is no genetic material. The goal is to estimate a and $\Delta$. It is also possible to estimate b independently, but assume for now that the noise level is roughly constant across loci, and only use the set of equations based on parent contexts to estimate a and $\Delta$. The measurement at each locus is given by $$y_{ijk} = b + am_{ijk} + \Delta c_{ijk} + v_{ijk}$$

Assuming that the noise $v_{ijk}$ is i.i.d. for each of the measurements within a particular parent context, T, one can sum the signals within that parent context. The parent contexts are represented in terms of alleles A and B, where the first two alleles represent the mother and the second two alleles represent the father: T∈{AA|BB, BB|AA, AB|AB, AA|AA, BB|BB, AA|AB, AB|AA, AB|BB, BB|AB}. For each context T, there is a set of loci i,j where the parent DNA conforms to that context, represented i,j∈T. Hence:

$$y_{T,k} = \frac{1}{N_T} \sum_{i,j \in T} y_{i,j,k} = b + a\overline{m_{k,T}} + \Delta \overline{c_{k,T}} + \overline{v_{k,T}}$$

Where $\overline{m_{k,T}}$, $\overline{c_{k,T}}$, and $\overline{v_{k,T}}$ represent the means of the respective values over all the loci conforming to the parent context T, or over all i,j∈T. The mean or expected values $\overline{c_{k,T}}$ will depend on the ploidy status of the child. The table below describes the mean or expected values $\overline{m_{k,T}}$ and $\overline{c_{k,T}}$ for k=1(allele A) or 2(allele B) and all the parent contexts T. One may calculate the expected values assuming different hypotheses on the child, namely euploidy and maternal trisomy. The hypotheses are denoted by the notation $H_{mf}$, where m refers to the number of chromosomes from the mother and f refers to the number of chromosomes from the father e.g. $H_{11}$ is euploid, $H_{21}$ is maternal trisomy. Note that there is symmetry between some of the states by switching A and B, but all states are included for clarity:

| Context | AA/BB | BB/AA | AB/AB | AA/AA | BB/BB | AA/AB | AB/AA | AB/BB | BB/AB |
|---|---|---|---|---|---|---|---|---|---|
| $\overline{m_{A,T}}$ | 2 | 0 | 1 | 2 | 0 | 2 | 1 | 1 | 0 |
| $\overline{m_{B,T}}$ | 0 | 2 | 1 | 0 | 2 | 0 | 1 | 1 | 2 |
| $\overline{c_{A,T}}|H_{11}$ | 1 | 1 | 1 | 2 | 0 | 1.5 | 1.5 | 0.5 | 0.5 |
| $\overline{c_{B,T}}|H_{11}$ | 1 | 1 | 1 | 0 | 2 | 0.5 | 0.5 | 1.5 | 1.5 |
| $\overline{c_{A,T}}|H_{21}$ | 2 | 1 | 1.5 | 3 | 0 | 2.5 | 2 | 1 | 0.5 |
| $\overline{c_{B,T}}|H_{21}$ | 1 | 2 | 1.5 | 0 | 3 | 0.5 | 1 | 2 | 2.5 |

It is now possible to write a set of equations describing all the expected values $y_{T,k}$, which can be cast in matrix form, as follows:

$$Y = B + A_H P + v$$

Where $$Y = \begin{bmatrix} y_{AA|BB,1} & y_{BB|AA,1} & y_{AB|BB,1} & y_{AA|AA,1} & y_{BB|BB,1} & y_{AA|AB,1} & y_{AB|AA,1} & y_{AB|BB,1} & y_{BB|AB,1} \\ y_{AA|BB,2} & y_{BB|AA,2} & y_{AB|AB,2} & y_{AA|AA,2} & y_{BB|BB,2} & y_{AA|AB,2} & y_{AB|AA,2} & y_{AB|BB,2} & y_{BB|AB,2} \end{bmatrix}^T$$

is the matrix of parameters to estimate

B=b$\vec{1}$ where $\vec{b}1$ is the 18×1 matrix of ones
v=$[\overline{v_{A,AA|BB}}\ldots v_{B,BB|AB}]^T$ is the 18×1 matrix of noise terms and $A_H$ is the matrix encapsulating the data in the table, where the values are different for each hypothesis H on the ploidy state of the child. Below are examples of the Matrix $A_H$ for the ploidy hyoptheses $H_{11}$ and $H_{21}$ $$A_{H11} = \begin{bmatrix} 2.0 & 1.0 \\ 0 & 1.0 \\ 1.0 & 1.0 \\ 2.0 & 2.0 \\ 0 & 0 \\ 2.0 & 1.5 \\ 1.0 & 1.5 \\ 1.0 & 0.5 \\ 0 & 0.5 \\ 0 & 1.0 \\ 2.0 & 1.0 \\ 1.0 & 1.0 \\ 0 & 0 \\ 2.0 & 2.0 \\ 0 & 0.5 \\ 1.0 & 0.5 \\ 1.0 & 1.5 \\ 2.0 & 1.5 \end{bmatrix} \quad A_{H21} = \begin{bmatrix} 2.0 & 2.0 \\ 0 & 1.0 \\ 1.0 & 1.5 \\ 2.0 & 3.0 \\ 0 & 0 \\ 2.0 & 2.5 \\ 1.0 & 2.0 \\ 1.0 & 1.0 \\ 0 & 0.5 \\ 0 & 1.0 \\ 2.0 & 2.0 \\ 1.0 & 1.5 \\ 0 & 0 \\ 2.0 & 3.0 \\ 0 & 0.5 \\ 1.0 & 1.0 \\ 1.0 & 2.0 \\ 2.0 & 2.5 \end{bmatrix}$$

In order to estimate a and Δ, or matrix P, aggregate the data across a set of chromosomes that one may assume are euploid on the child sample. This could include all chromosomes j=1 . . . 23 except those that are under test, namely j=13, 18, 21, X and Y. (Note: one could also apply a concordance test for the results on the individual chromosomes in order to detect mosaic aneuploidy on the non-viable chromosomes). In order to clarify notation, define Y' as Y measured over all the euploid chromosomes, and Y" as Y measured over a particular chromosome under test, such as chromosome 21, which may be aneuploid. Apply the matrix $A_{H_{11}}$ to the euploid data in order to estimate the parameters:

$$\hat{P} = \text{argmin}_P \|Y'-B-A_{H_{11}}P\|_2 = (A_{H_{11}}^T A_{H_{11}})^{-1} A_{H_{11}}^T \tilde{Y}$$

where $\tilde{Y}=Y'-B$, i.e., the measured data with the bias removed. The least-squares solution above is only the maximum-likelihood solution if each of the terms in the noise matrix v has a similar variance. This is not the case, most simply because the number of loci $N'_T$ used to compute the mean measurement for each context T is different for each context. As above, use the $N_T'$ to refer to the number of loci used on the chromosomes known to be euploid, and use the C' to denote the covariance matrix for mean measurements on the chromosomes known to be euploid. There are many approaches to estimating the covariance C' of the noise matrix v, which one may assume is distributed as v~N(0, C'). Given the covariance matrix, the maximum-likelihood estimate of P is $$\hat{P} = \text{argmin}_P \|C'^{-1/2}(Y'-B-A_{H_{11}}P)\|_2 = (A_{H_{11}}^T C'^{-1} A_{H_{11}})^{-1} A_{H_{11}}^T C'^{-1} \tilde{Y}$$

One simple approach to estimating the covariance matrix is to assume that all the terms of v are independent (i.e. no off-diagonal terms) and invoke the Central Limit Theorem so that the variance of each term of v scales as $1/N'_T$ so that one may find the 18×18 matrix $$C' = \begin{bmatrix} 1/N'_{AA|BB} & \cdots & 0 \\ \vdots & \ddots & \vdots \\ 0 & \cdots & 1/N'_{BB|AB} \end{bmatrix}$$

Once P' has been estimated, use these parameters to determine the most likely hypothesis on the chromosome under study, such as chromosome 21. In other words, choose the hypothesis:

$$H^* = \text{argmin}_H \|C''^{-1/2}(Y''-B-A_H \hat{P})\|_2$$

Having found H* one may then estimate the degree of confidence that one may have in the determination of H*. Assume, for example, that there are two hypotheses under consideration: $H_{11}$ (euploid) and $H_{21}$ (maternal trisomy). Assume that $H^*=H_{11}$. Compute the distance measures corresponding to each of the hypotheses:

$$d_{11} = \|C''^{-1/2}(Y''-B-A_{H_{11}}\hat{P})\|_2$$

$$d_{21} = \|C''^{-1/2}(Y''-B-A_{H_{21}}\hat{P})\|_2$$

It can be shown that the square of these distance measures are roughly distributed as a Chi-Squared random variable with 18 degrees of freedom. Let $\chi_{18}$ represent the corresponding probability density function for such a variable. One may then find the ratio in the probabilities $p_H$ of each of the hypotheses according to:

$$\frac{p_{H_{11}}}{p_{H_{21}}} = \frac{\chi_{18(d_{11}^2)}}{\chi_{18(d_{21}^2)}}$$

One may then compute the probabilities of each hypothesis by adding the equation $p_{H_{11}}+p_{H_{21}}=1$. The confidence that the chromosome is in fact euploid is given by $p_{H_{11}}$.

Variations on the Method (1) One may modify the above approach for different biases b on each of the channels representing alleles A and B. The bias matrix B is redefined as follows:

$$B = \begin{bmatrix} b_A \vec{1} \\ b_B \vec{1} \end{bmatrix}$$

where $\vec{1}$ is a 9×1 matrix of ones. As discussed above, the parameters $b_e$ and $b_{ib}$ can either be assumed based on a-priori measurements, or can be included in the matrix P and actively estimated (i.e. there is sufficient rank in the equations over all the contexts to do so).

(2) In the general formulation, where $y_{ijk}=g_{ijk}(am_{ijk}+\Delta c_{ijk})+v_{ijk}$, one may directly measure or calibrate the function $g_{ijk}$ for every locus and allele, so that the function (which one may assume is monotonic for the vast majority of genotyping platforms) can be inverted. One may then use the function inverse to recast the measurements in terms of the quantity of genetic material so that the system of equations is linear i.e. $y'_{ijk}=g_{ijk}^{-1}(y_{ijk})=am_{ijk}+\Delta c_{ijk}+v'_{ijk}$. This approach is particularly good when $g_{ijk}$ is an affine function so that the inversion does not produce amplification or biasing of the noise in $v'_{ijk}$.

(3) The method above may not be optimal from a noise perspective since the modified noise term $v'_{ijk}=g_{ijk}^{-1}(v_{ijk})$ may be amplified or biased by the function inversion. Another approach is to linearism the measurements around an operating point i.e. $y_{ijk} = g_{ijk}(am_{ijk} + \Delta c_{ijk}) + v_{ijk}$ may be recast as: $y_{ijk} \approx g_{ijk}(am_{ijk}) + g_{ijk}'(am_{ijk}) \Delta c_{ijk} + v_{ijk}$. Since one may expect no more than 30% of the free-floating DNA in the maternal blood to be from the child, $\Delta \ll a$, and the expansion is a reasonable approximation. Alternatively, for a platform response such as that of the ILLUMINA BEAD ARRAY, which is monotonically increasing and for which the second derivative is always negative, one could improve the linearization estimate according to $y_{ijk} \approx g_{ijk}(am_{ijk}) + 0.5 (g_{ijk}'(am_{ijk}) + g_{ijk}'(am_{ijk} + \Delta c_{ijk})) \Delta c_{ijk} + v_{ijk}$. The resulting set of equations may be solved iteratively for a and $\Delta$ using a method such as Newton-Raphson optimization.

(4) Another general approach is to measure at the total amount of DNA on the test chromosome (mother plus fetus) and compare with the amount of DNA on all other chromosomes, based on the assumption that amount of DNA should be constant across all chromosomes. Although this is simpler, one disadvantage is that it is now known how much is contributed by the child so it is not possible to estimate confidence bounds meaningfully. However, one could look at standard deviation across other chromosome signals that should be euploid to estimate the signal variance and generate a confidence bound. This method involves including measurements of maternal DNA which are not on the child DNA so these measurements contribute nothing to the signal but do contribute directly to noise. In addition, it is not possible to calibrate out the amplification biases amongst different chromosomes. To address this last point, it is possible to find a regression function linking each chromosome's mean signal level to every other chromosomes mean signal level, combine the signal from all chromosome by weighting based on variance of the regression fit, and look to see whether the test chromosome of interest is within the acceptable range as defined by the other chromosomes.

(5) This method may be used in conjunction with other method previously disclosed by Gene Security Network, especially those method that are part of PARENTAL SUPPORT™, such that one may phase the parents so that it is known what is contained on each individual maternal and paternal chromosome. By considering the odds ratio of each of the alleles at heterozygous loci, one may determine which haplotype of the mother is present on the child. Then one can compare the signal level of the measurable maternal haplotype to the paternal haplotype that is present (without background noise from the mother) and see when that ratio of 1:1 is not satisfied due to aneuploidy which causes an imbalance between maternal and paternal alleles.

This list of possible variations on the method is not meant to be exhaustive. Other variation may also be employed.

Maximum Likelihood Model Using Percent Fetal Fraction

Determining the ploidy status of a fetus by measuring the free floating DNA contained in maternal serum, or by measuring the genotypic data contained in any mixed sample, is a non-trivial exercise. There are a number of methods, for example, performing a read count analysis where the presumption is that if the fetus is trisomic at a particular chromosome, then the overall amount of DNA from that chromosome found in the maternal blood will be elevated with respect to a reference chromosome. One way to detect trisomy in such fetuses is to normalize the amount of DNA expected for each chromosome, for example, according to the number of SNPs in the analysis set that correspond to a given chromosome, or according to the number of uniquely mappable portions of the chromosome. Once the measurements have been normalized, any chromosomes for which the amount of DNA measured exceeds a certain threshold are determined to be trisomic. This approach is described in Fan, et al. PNAS, 2008; 105(42); pp. 16266-16271, and also in Chiu et al. BMJ 2011; 342:c7401. In the Chiu et al. paper, the normalization was accomplished by calculating a Z score as follows:

Z score for percentage chromosome 21 in test case= ((percentage chromosome 21 in test case)−(mean percentage chromosome 21 in reference controls))/(standard deviation of percentage chromosome 21 in reference controls).

These methods determine the ploidy status of the fetus using a single hypothesis rejection method. However, they suffer from some significant shortcomings. Since these methods for determining ploidy in the fetus are invariant according to the percentage of fetal DNA in the sample, they use one cut off value; the result of this is that the accuracies of the determinations are not optimal, and those cases where the percentage of fetal DNA in the mixture are relatively low will suffer the worst accuracies.

In one embodiment of the present disclosure, the method used to determine the ploidy state of the fetus involves taking into account the fraction of fetal DNA in the sample. In another embodiment of the present disclosure, the method involves the use of maximum likelihood estimations. In one embodiment of the present disclosure, the method involves calculating the percent of DNA in a sample that is fetal or placental in origin. In one embodiment of the present disclosure, the threshold for calling aneuploidy is adaptively adjusted based on the calculated percent fetal DNA. In some embodiments, the method for estimating the percentage of DNA that is of fetal origin in a mixture of DNA, comprises obtaining a mixed sample that contains genetic material from the mother, and genetic material from the fetus, obtaining a genetic sample from the father of the fetus, measuring the DNA in the mixed sample, measuring the DNA in the father sample, and calculating the percentage of DNA that is of fetal origin in the mixed sample using the DNA measurements of the mixed sample, and of the father sample.

In one embodiment of the present disclosure, the fraction of fetal DNA, or the percentage of fetal DNA in the mixture can be measured. In some embodiments the fraction can be calculated using only the genotyping measurements made on the maternal plasma sample itself, which is a mixture of fetal and maternal DNA. In some embodiments the fraction may be calculated also using the measured or otherwise known genotype of the mother and/or the measured or otherwise known genotype of the father. In some embodiments the percent fetal DNA may be calculated using the measurements made on the mixture of maternal and fetal DNA along with the knowledge of the parental contexts. In one embodiment the fraction of fetal DNA may be calculated using population frequencies to adjust the model on the probability on particular allele measurements.

In one embodiment of the present disclosure, a confidence may be calculated on the accuracy of the determination of the ploidy state of the fetus. In one embodiment, the confidence of the hypothesis of greatest likelihood ($H_{major}$) may be calculated as $(1 - H_{major})/\Sigma(\text{all } H)$. It is possible to determine the confidence of a hypothesis if the distributions of all of the hypotheses are known. It is possible to determine the distribution of all of the hypotheses if the parental genotype information is known. It is possible to calculate a confidence of the ploidy determination if the knowledge of the expected distribution of data for the euploid fetus and the expected distribution of data for the aneuploid fetus are known. It is possible to calculate these expected distributions if the parental genotype data are known. In one embodiment one may use the knowledge of the distribution of a test statistic around a normal hypothesis and around an abnormal hypothesis to determine both the reliability of the call as well as refine the threshold to make a more reliable call. This is particularly useful when the amount and/or percent of fetal DNA in the mixture is low. It will help to avoid the situation where a fetus that is actually aneuploid is found to be euploid because a test statistic, such as the Z statistic does not exceed a threshold that is made based on a threshold that is optimized for the case where there is a higher percent fetal DNA.

Ploidy Calling for a Mother/Child Mixture

Described herein is a method for determining the ploidy state of a fetus given sequence data that was measured on free floating DNA isolated from maternal blood, wherein the free floating DNA contains some DNA of maternal origin, and some DNA of fetal/placental origin. This section will describe one embodiment of the present disclosure in which the ploidy state of the fetus is determined using the calculated fraction of fetal DNA in the mixture that has been analyzed. It will also describe an embodiment in which the fraction of fetal DNA or the percentage of fetal DNA in the mixture can be measured. In some embodiments the fraction can be calculated using only the genotyping measurements made on the maternal blood sample itself, which is a mixture of fetal and maternal DNA. In some embodiments the fraction may be calculated also using the measured or otherwise known genotype of the mother and/or the measured or otherwise known genotype of the father.

For a particular chromosome, suppose there are N SNPs, for which:
Parent genotypes from ILLUMINA data, assumed to be correct: mother $m=(m_1, \ldots, m_N)$, father $f=(f_1, \ldots, f_N)$, where $m_i, f_i \in (AA, AB, BB)$.
Set of NR sequence measurements $S=(s_1, \ldots, s_{nr})$.

Deriving Most Likely Copy Number from Data

For each copy number hypothesis H considered, derive data log likelihood LIK(H) on a whole chromosome and choose the best hypothesis maximizing LIK, i.e.

$$H^* = \underset{H}{\operatorname{argmax}} LIK(H)$$

Copy number hypotheses considered are:
Monosomy:
  maternal H10 (one copy from mother)
  paternal H01 (one copy from father)
Disomy: H11 (one copy each mother and father)
Simple trisomy, no crossovers considered:
  Maternal: H21_matched (two identical copies from mother, one copy from father), H21_unmatched (BOTH copies from mother, one copy from father)
  Paternal: H12_matched (one copy from mother, two identical copies from father), H12_unmatched (one copy from mother, both copies from father)
Composite trisomy, allowing for crossovers (using a joint distribution model):
  maternal H21 (two copies from mother, one from father),
  paternal H12 (one copy from mother, two copies from father)

If there were no crossovers, each trisomy, whether the origin was mitotis, meiosis I, or meiosis II, would be one of the matched or unmatched trisomies. Due to crossovers, true trisomy is a combination of the two. First, a method to derive hypothesis likelihoods for simple hypotheses is described. Then a method to derive hypothesis likelihoods for composite hypotheses is described, combining individual SNP likelihood with crossovers.

LIK(H) for Simple Hypotheses

For simple hypotheses H, LIK(H), the log likelihood of hypothesis H on a whole chromosome, is calculated as the sum of log likelihoods of individual SNPs, i.e.

$$LIK(H) = \sum_i LIK(i, H)$$

This hypothesis does not assume any linkage between SNPs, and therefore does not utilize a joint distribution model.

Log Likelihood Per SNP

On a particular SNP i, define $m_i$=true mother genotype, $f_i$=true father genotype, cf=known or derived child fraction. Let $x_i = P(A|i, S)$ be the probability of having an A on SNP i, given the sequence measurements S. Assuming child hypothesis H, log likelihood of observed data on SNP i is defined as $$LIK(i, H) = \log lik(x_i | m_i, f_i, H, cf) = \sum_c p(c | m_i, f_i, H) * \log lik(x_i | m_i, c, cf)$$

p(c|m, f, H) is the probability of getting true child genotype=c, given parents m, f, and assuming hypothesis H, which can be easily calculated. For example, for H11, H21 matched and H21 unmatched, p(c|m,f,H) is given below.

| | | p(c\|m, f, H) | | | | | | | | | |
|---|---|---|---|---|---|---|---|---|---|---|---|
| | | H11 | | | H21 matched | | | | H21 unmatched | | | |
| m | f | AA | AB | BB | AAA | AAB | ABB | BBB | AAA | AAB | ABB | BBB |
| AA | AA | 1 | 0 | 0 | 1 | 0 | 0 | 0 | 1 | 0 | 0 | 0 |
| AB | AA | 0.5 | 0.5 | 0 | 0.5 | 0 | 0.5 | 0 | 0 | 1 | 0 | 0 |
| BB | AA | 0 | 1 | 0 | 0 | 0 | 1 | 0 | 0 | 0 | 1 | 0 |
| AA | AB | 0.5 | 0.5 | 0 | 0.5 | 0.5 | 0 | 0 | 0.5 | 0.5 | 0 | 0 |
| AB | AB | 0.25 | 0.5 | 0.25 | 0.25 | 0.25 | 0.25 | 0.25 | 0 | 0.5 | 0.5 | 0 |
| BB | AB | 0 | 0.5 | 0.5 | 0 | 0 | 0.5 | 0.5 | 0 | 0 | 0.5 | 0.5 |
| AA | BB | 0 | 1 | 0 | 0 | 1 | 0 | 0 | 0 | 1 | 0 | 0 |
| AB | BB | 0 | 0.5 | 0.5 | 0 | 0.5 | 0 | 0.5 | 0 | 0 | 1 | 0 |
| BB | BB | 0 | 0 | 1 | 0 | 0 | 0 | 1 | 0 | 0 | 0 | 1 | lik($x_i$|m,c,cf) is the likelihood of getting derived probability $x_i$ on SNP i, assuming true mother m, true child c, defined as $pdf_x(x_i)$ of the distribution that $x_i$ should be following if hypothesis H were true. In particular lik($x_i$|m,c,cf)=$pdf_x(x_i)$ In a simple case where Di of NR sequences in S line up to SNP i, X~(1/$D_i$)Bin(p,$D_i$), where p=p(A|m,c,cf)=probability of getting an A, for this mother/child mixture, calculated as:

$$p(A \mid m, c, cf) = \frac{\#A(m) * (1 - cf_{correct}) + \#A(c) * cf_{correct}}{n_m * (1 - cf_{correct}) + n_c * cf_{correct}}$$

where #A(g)=number of A's in genotype g, $n_m$=2 is somy of mother and $n_c$ is somy of the child, (1 for monosomy, 2 for disomy, 3 for trisomy).
$cf_{correct}$ is corrected fraction of the child in the mixture $$cf_{correct} = cf * \frac{n_c}{n_m * (1 - cf) + n_c * cf}$$

If child is a disomy $cf_{correct}$=cf, but for a trisomy fraction of the child in the mix for this chromosome is actually a bit higher $$cf_{correct} = cf * \frac{3}{2 + cf}.$$

In a more complex case where there is not exact alignment, X is a combination of binomials integrated over possible Di reads per SNP.

Using a Joint Distribution Model: LIK(H) for a Composite Hypothesis

In real life, trisomy is usually not purely matched or unmatched, due to crossovers, so in this section results for composite hypotheses H21 (maternal trisomy) and H12 (paternal trisomy) are derived, which combine matched and unmatched trisomy, accounting for possible crossovers.

In the case of trisomy, if there were no crossovers, trisomy would be simply matched or unmatched trisomy. Matched trisomy is where child inherits two copies of the identical chromosome segment from one parent. Unmatched trisomy is where child inherits one copy of each homologous chromosome segment from the parent. Due to crossovers, some segments of a chromosome may have matched trisomy, and other parts may have unmatched trisomy. Described in this section is how to build a joint distribution model for the heterozygosity rates for a set of alleles.

Suppose that on SNP i, LIK(i, Hm) is the fit for matched hypothesis H, and LIK(i, Hu) is the fit for UNmatched hypothesis H, and pc(i)=probability of crossover between SNPs i−1,i. One may then calculate the full likelihood as:

LIK(H)=$\Sigma_{S,E}$LIK(S,E,1:N)

where LIK(S, E, 1: N) is the likelihood starting with hypothesis S, ending in hypothesis E, for SNPs 1:N. S=hypothesis of the first SNP, E=hypothesis of the last SNP, S,E∈(Hm, Hu). Recursivelly one may calculate:

LIK(S,E,1:i)=LIK(i,E)+log(exp(LIK(S,E,1:i−1))*
(1−pc(i))+exp(LIK(S,~E,1:i−1))*pc(i))

where ~E is the other hypothesis (not E). In particular, one may calculate the likelihood of 1:i SNPs, based on likelihood of 1:(i−1) SNPs with either the same hypothesis and no crossover or the opposite hypothesis and a crossover times the likelihood of the SNP i
For SNP i=1:

$$LIK(S, E, 1:1) = \begin{cases} LIK(1, S) & \text{if } S = E \\ 0 & \text{if } S \neq E \end{cases}$$

Then calculate:

LIK(S,E,1:2)=LIK(2,E)+log(exp(LIK(S,E,1))*(1−pc(2))+exp(LIK(S,~E,1))*pc(2))

And so on until i=N.
Deriving Child Fraction

The above formulas assume a known child fraction, which is not always the case. In one embodiment, it is possible to find the most likely child fraction by maximizing the likelihood for disomy on selected chromosomes.

In particular, supposes that LIK(chr, H11, cf)=log likelihood as described above, for the disomy hypothesis, and for child fraction cf on chromosome chr. For selected chromosomes in Cset (usually 1:16). Then the full likelihood is:

LIK(cf)=$\Sigma_{chr \in Cset}$Lik(chr,H11,cf)

and cf*=argmax$_{cf}$LIK(cf).

It is possible to use any set of chromosomes. It is also possible to derive child fraction without paternal data, as follows:
Deriving Copy Number without Paternal Data Recall the formula of the simple hypothesis log likelihood on SNP i $$LIK(i, H) =$$
$$\text{log}lik(x_i \mid m_i, f_i, H, cf) = \sum_c p(c \mid m_i, f_i, H) * \text{log}lik(x_i \mid m_i, c, cf)$$

Determining the probability of the true child given parents p(c|$m_i$, $f_i$, H) requires the knowledge of father genotype. If the father genotype is unknown, but p$A_i$, the population frequency of A allele on this SNP, is known, it is possible to approximate the above likelihood with $$LIK(i, H) = \text{log}lik(x_i \mid m_i, f_i, H, cf) =$$
$$\sum_c p(c \mid m_i, H) * \text{log}lik(x_i \mid m_i, c, H, cf) \text{ where } p(c \mid m_i, H) =$$
$$\sum_f p(c \mid m_i, f, H) * p(f \mid pA_i)$$

where p(f|p$A_i$) is the probability of particular father genotype, given the frequency of A on SNP i.
In particular:

p(AA|p$A_i$)=(p$A_i$)², p(AB|p$A_i$)=2(p$A_i$)*(1−p$A_i$), p(BB|p$A_i$)=(1−p$A_i$)²

Incorporating Data Dropouts

Elsewhere in this disclosure it has been assumed that the probability of getting an A is a direct function of the true mother genotype, the true child genotype, the fraction of the child in the mix, and the child copy number. It is also possible that mother or child alleles can drop out, for example instead of having true child AB in the mix, there is only A, in which case the chance of getting a nexus sequence measurement of A are much higher. Assume that mother dropout rate is MDO, and child dropout rate is CDO. In some embodiments, the mother dropout rate can be assumed to be zero, and child dropout rates are relatively low, so the results in practice are not severely affected by dropouts. Nonetheless, they have been incorporated into the algorithm here. Elsewhere, lik $(x_i|m_i, c, cf)=pdf_X(x_i)$ has been defined as the likelihood of getting $x_i$ probability of A on SNP i, given sequence measurements S, assuming true mother $m_i$, true child c. If there is a dropout in the mother or child, the input data is NOT true mother $(m_i)$ or child (c), but mother after possible dropout $(m_d)$ and child after a possible dropout $(c_d)$. One can then rewrite the above formula as $$lik(x_i | m_i, c, cf) = \sum_{m_d, c_d} p(m_d | m_i) * p(c_d | c) * lik(x_i | m_d, c_d, cf)$$

where $p(m_d|m_i)$ is the probability of new mother genotype $m_d$, given true mother genotype $m_i$, assuming dropout rate mdo, and $p(c_d|c)$ is the probability of new child genotype $c_d$, given true child genotype c, assuming dropout rate CDO. If $nA_T$=number of A alleles in true genotype c, $nA_D$=number of A alleles in 'drop' genotype $c_d$, where $nA_T \geq nA_D$, and similarly $nB_T$=number of B alleles in true genotype c, $nB_D$=number of B alleles in 'drop' genotype $c_d$, where $nB_T \geq nB_D$ and d=dropout rate, then $$p(c_d | c) = \binom{nA_T}{nA_D} * d^{nA_T - nA_D} * (1-d)^{nA_D} * \binom{nB_T}{nB_D} * d^{nB_T - nB_D} * (1-d)^{nB_D}$$

For one set of experimental data, the parent genotypes have been measured, as well as the true child genotype, where the child has maternal trisomy on chromosomes 14 and 21. Sequencing measurements have been simulated for varying values of child fraction, N distinct SNPs, and total number of reads NR. From this data it is possible to derive the most likely child fraction, and derive copy number assuming known or derived child fraction.

Figure 2:
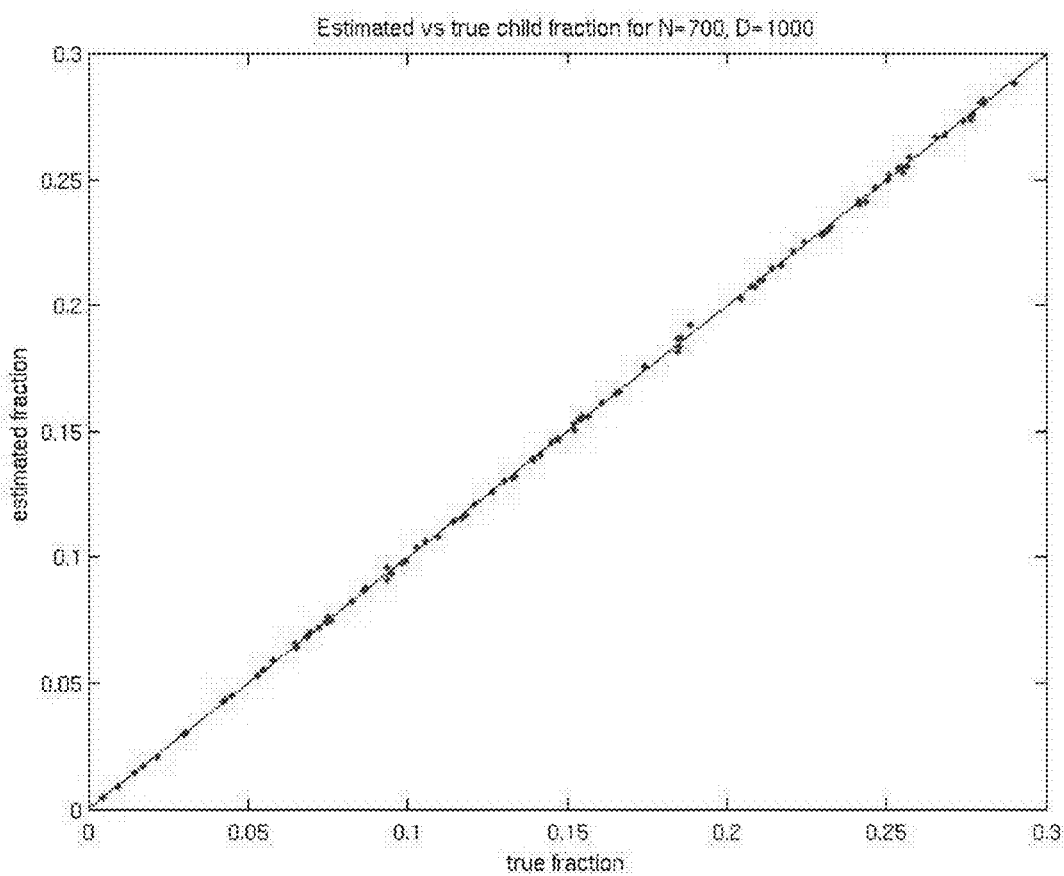
FIG. 2 shows a simulated and estimate child fraction.
Figures 3A, 3B, 3C, 3D, 3E:
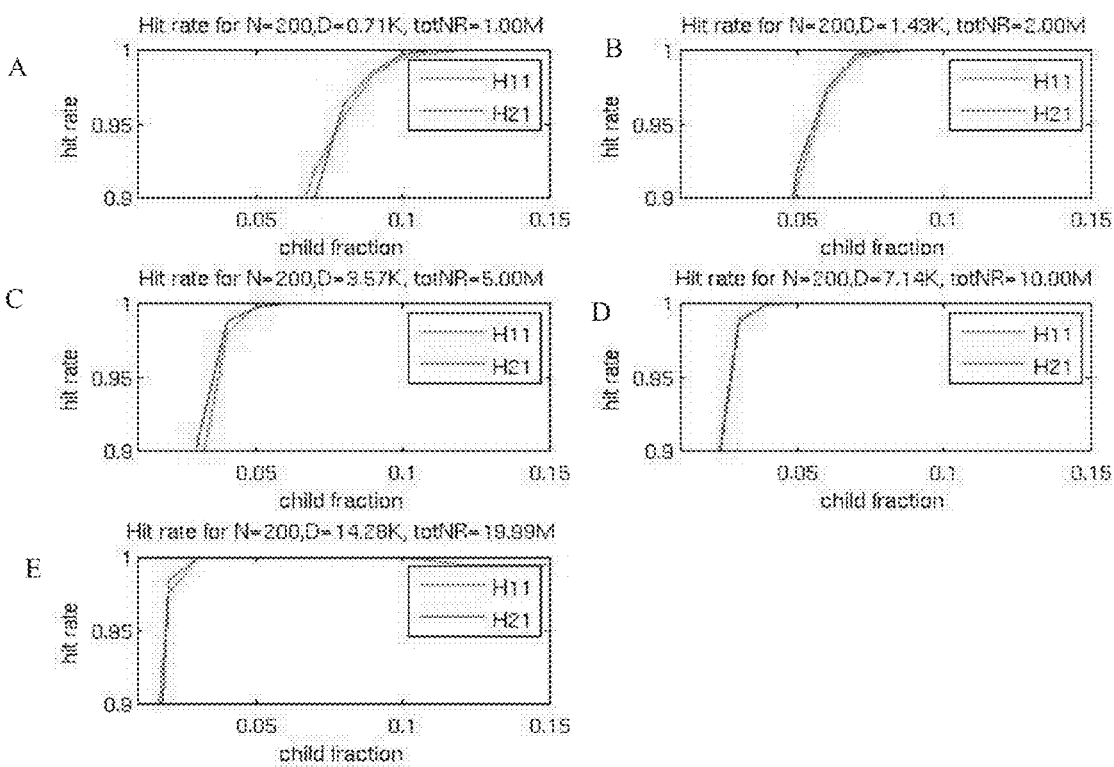
FIGS. 3A-3E show hit rates versus child fraction.
Figure 4:
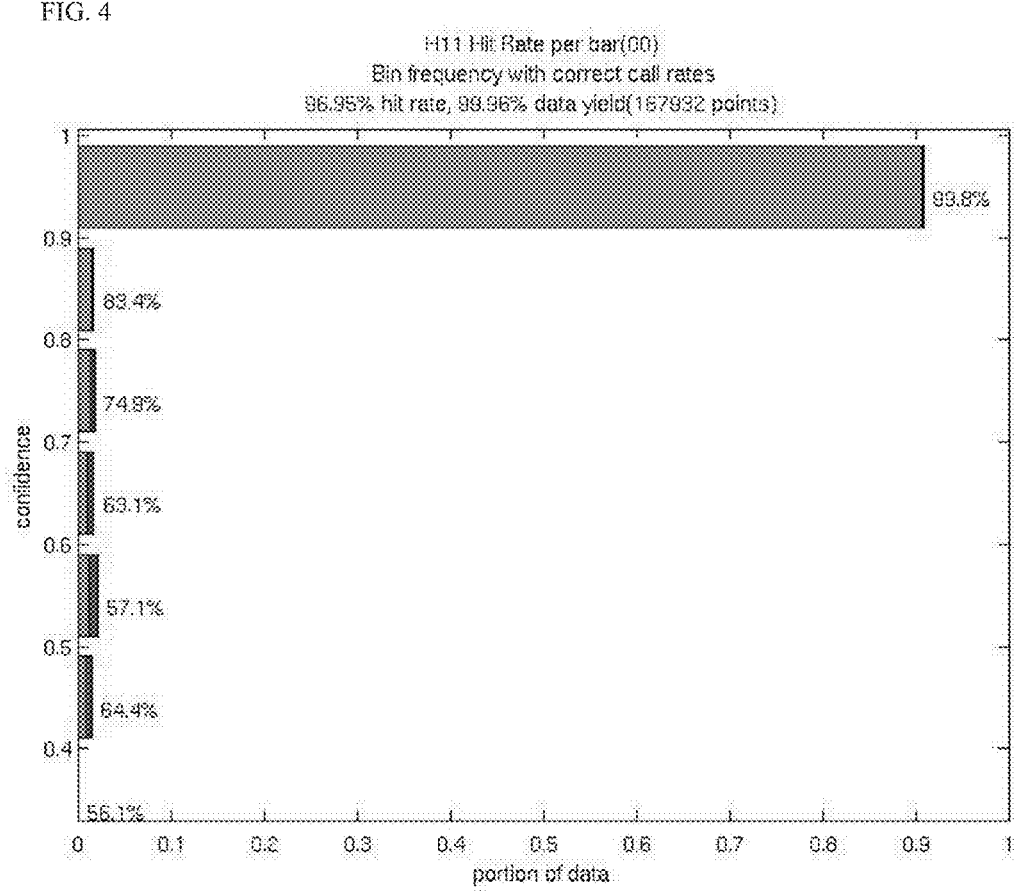
FIG. 4 shows hit rates versus confidence.
Figure 5:
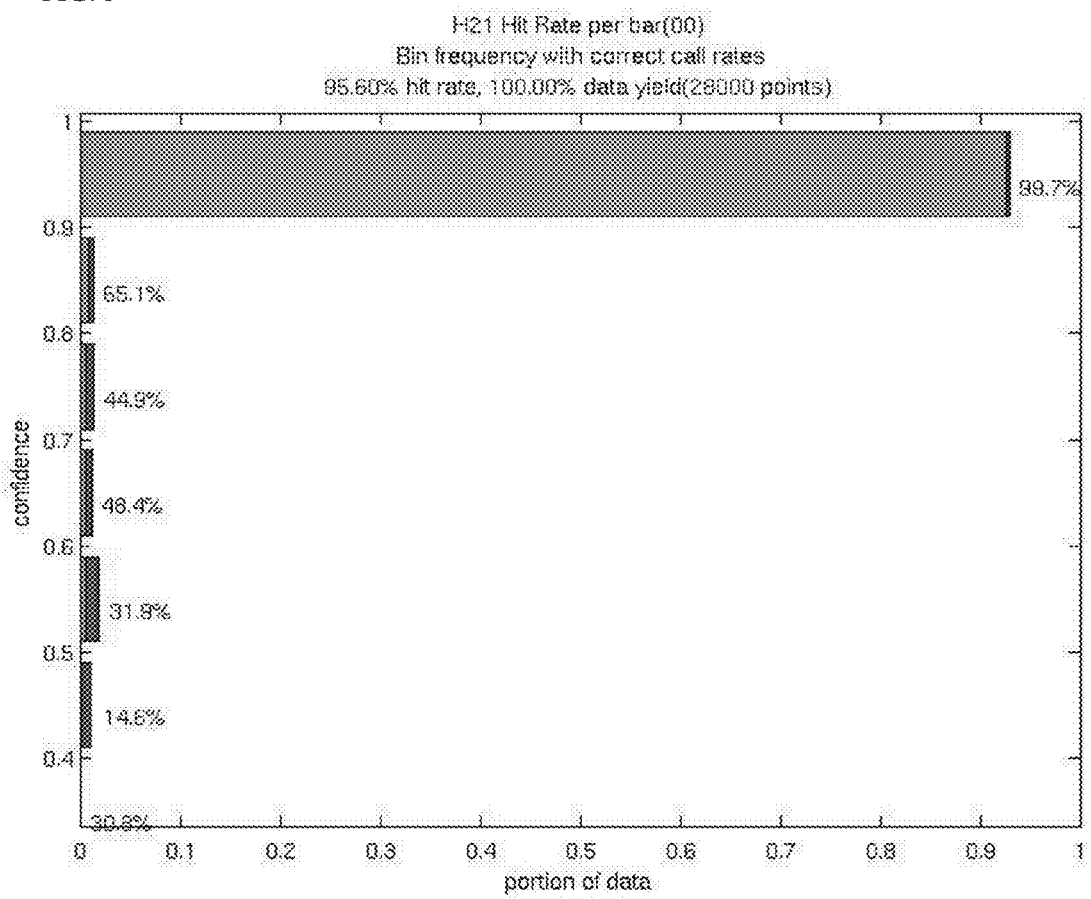
FIG. 5 shows hit rates versus confidence.
Figure 6A:
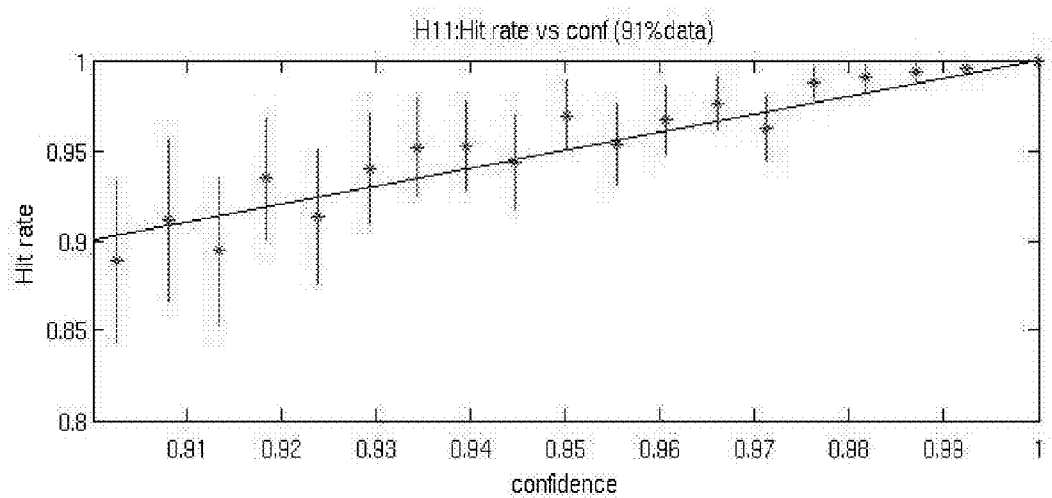
FIGS. 6A and 6B show hit rates versus confidence.
Figure 6B:
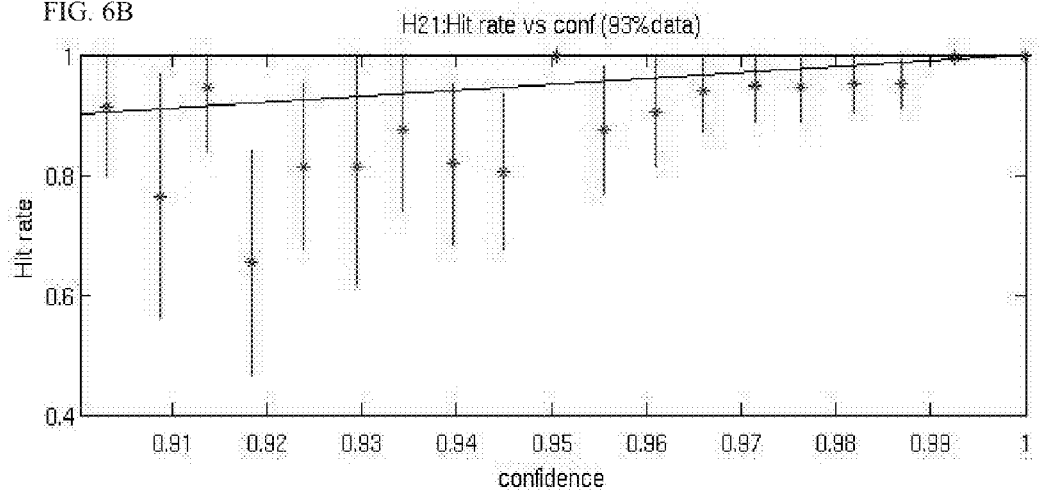
Figure 7A:
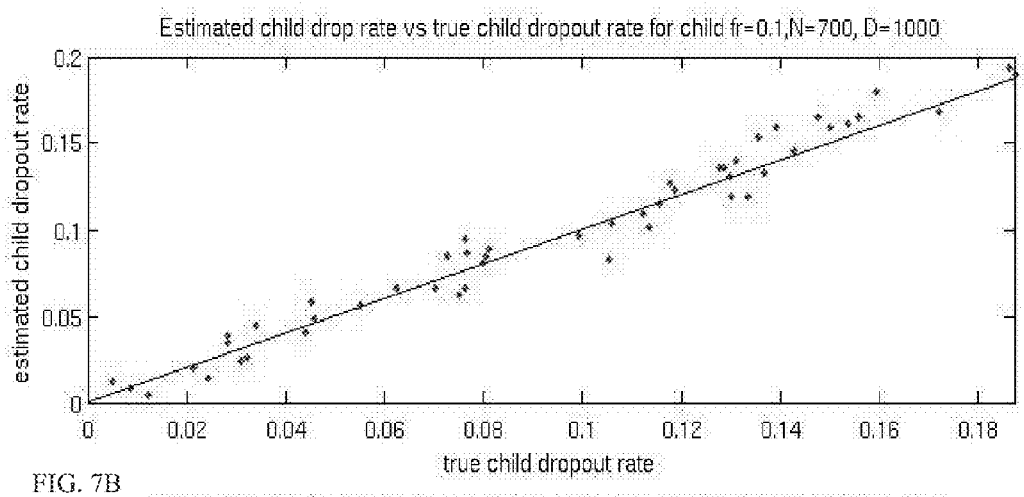
FIGS. 7A and 7B show an estimated versus true dropout rate.
Figure 7B:
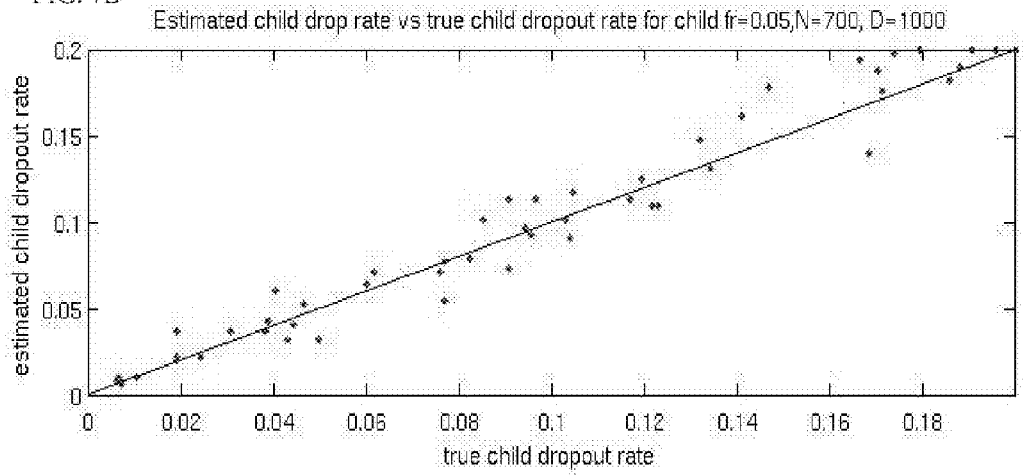
Figures 8A, 8B, 8C, 8D, 8E:
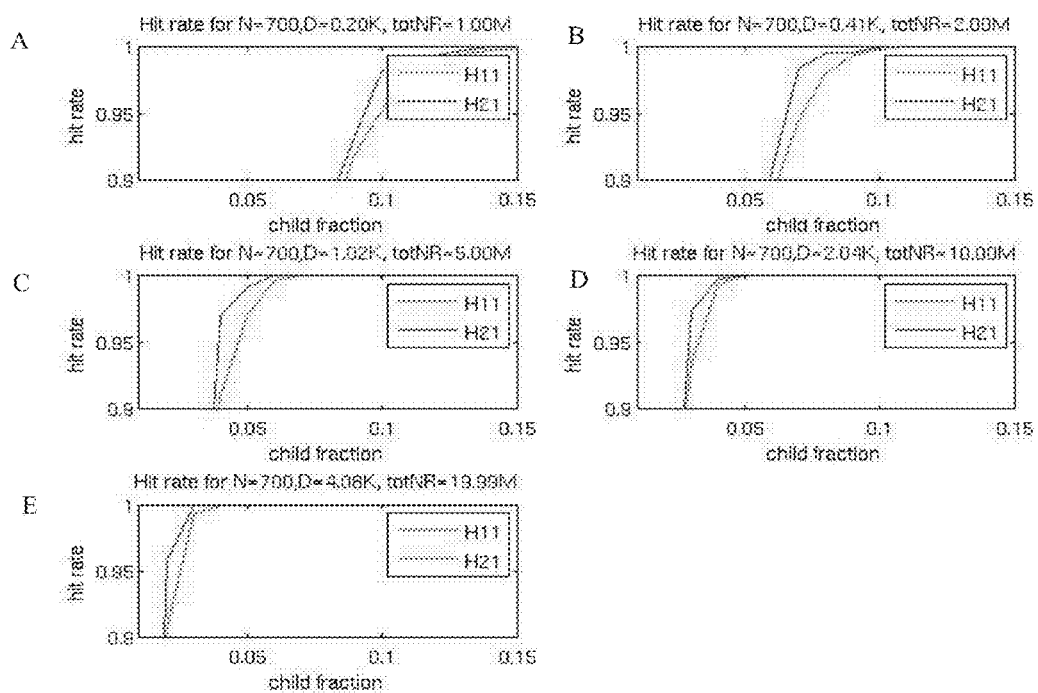
FIGS. 8A-8E show hit rates versus child fraction.

The simulated and estimate child fraction are shown in FIG. 2 for N=700, NR=700,000. The hit rate versus child fraction is shown in FIGS. 3A-3E for N=200 and varying NR, derived copy number hit rate, for true copy number=H11 or H21, versus true child fraction. The hit rate versus confidence is shown in FIGS. 4 and 5 for copy number estimates with combined results for N=200, all child fractions and NR, given as confidence bars and hit rates. The hit rate versus confidence is shown in FIGS. 6A and 6B for copy number estimates with combined results for N=200, all child fractions and NR, checking concordance of hit rates and given confidences, for range of confidence >90%, with error bars. An estimated versus true dropout rate is shown in FIGS. 7A and 7B for child fraction=0.05 and 0.1, N=700, NR=700,000; child dropout rates were estimated for a range of true dropout rates. The mother dropout rate is assumed to be zero. FIGS. 8A-8E show hit rates versus child fraction when the method includes a dropout model, assuming 5% dropout rate.

In one embodiment, the method disclosed herein can be used to determine a fetal aneuploidy by determining the number of copies of maternal and fetal target chromosomes, having target sequences in a mixture of maternal and fetal genetic material. This method may entail obtaining maternal tissue containing both maternal and fetal genetic material; in some embodiments this maternal tissue may be maternal plasma or a tissue isolated from maternal blood. This method may also entail obtaining a mixture of maternal and fetal genetic material from said maternal tissue by processing the aforementioned maternal tissue. This method may entail distributing the genetic material obtained into a plurality of reaction samples, to randomly provide individual reaction samples that contain a target sequence from a target chromosome and individual reaction samples that do not contain a target sequence from a target chromosome, for example, performing high throughput sequencing on the sample. This method may entail analyzing the target sequences of genetic material present or absent in said individual reaction samples to provide a first number of binary results representing presence or absence of a presumably euploid fetal chromosome in the reaction samples and a second number of binary results representing presence or absence of a possibly aneuploid fetal chromosome in the reaction samples. Either of the number of binary results may be calculated, for example, by way of an informatics technique that counts sequence reads that map to a particular chromosome, to a particular region of a chromosome, to a particular locus or set of loci. This method may involve normalizing the number of binary events based on the chromosome length, the length of the region of the chromosome, or the number of loci in the set. This method may entail calculating an expected distribution of the number of binary results for a presumably euploid fetal chromosome in the reaction samples using the first number. This method may entail calculating an expected distribution of the number of binary results for a presumably aneuploid fetal chromosome in the reaction samples using the first number and an estimated fraction of fetal DNA found in the mixture, for example, by multiplying the expected read count distribution of the number of binary results for a presumably euploid fetal chromosome by (1+n/2) where n is the estimated fetal fraction. The fetal fraction may be estimated by a plurality of methods, some of which are described elsewhere in this disclosure. This method may involve using a maximum likelihood approach to determine whether the second number corresponds to the possibly aneuploid fetal chromosome being euploid or being aneuploid. This method may involve calling the ploidy status of the fetus to be the ploidy state that corresponds to the hypothesis with the maximum likelihood of being correct given the measured data.

Using LIPs Plus Sequencing for Ploidy Calling

All data used in the following analysis is primary data as reported in the following publication: Porreca et al., Nature Methods, 2007 4(11), p. 931-936. In an embodiment, the present disclosure relates to a method for determining ploidy state of an individual given the genotypic data as output from a sequencing platform, where the genomic data has been amplified using a massively multiplex amplification procedure involving LIPs followed by ultra-high throughput sequencing.

The data set consists of 16 individuals. ~13,000 MIPs probes were selected. For each individual, 8 million reads were made, for a theoretical average read depth (number of reads/number of probes) of 615.

The 8 million reads must be mapped to locations on a reference genome in order to conduct analysis. This is done using the DNA Nexus web service. The processed data from DNA nexus contains the 8 million reads, in order of genome position, along with their alignment and QC properties.

There are several possible ways to proceed. One may make the copy number call by the total number of reads, and not necessarily the number of SNPs. Alternately, one may make the copy number call by the ratio of reads containing each allele on heterozygous SNPs.

Read Count Analysis

Figure 9:
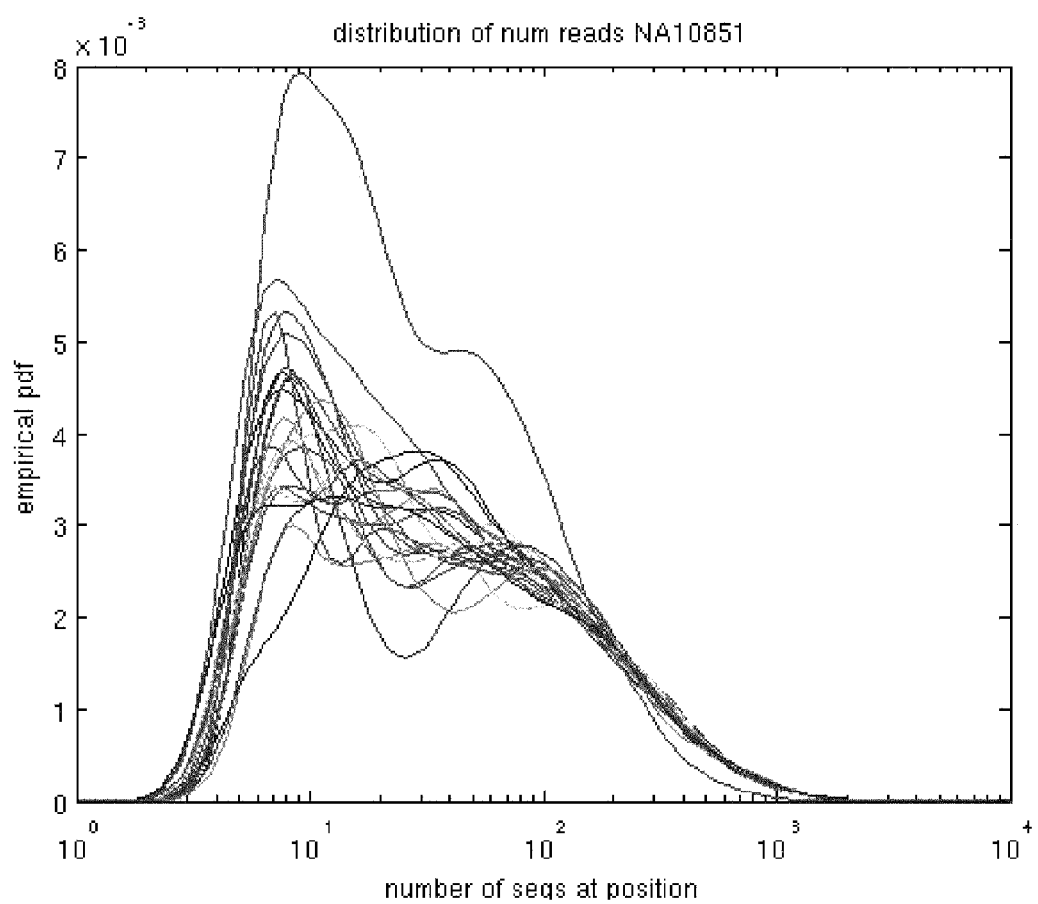
FIG. 9 shows a distribution of reads.
Figure 10:
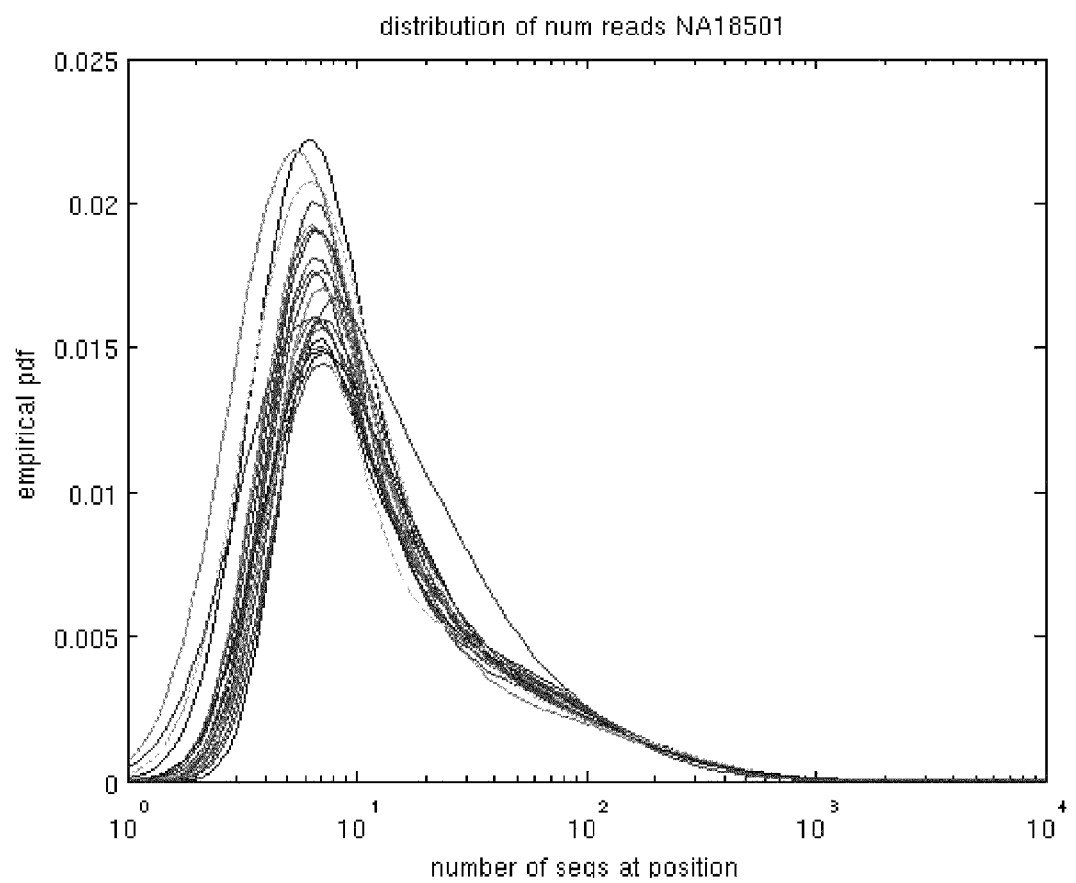
FIG. 10 shows a distribution of reads.

Initially looking only at forward reads, consider the number of reads at each position. If two reads have starting positions less than 5 bases apart, consider them the same and combine. This figure shows the distribution of sequence count over the different positions. FIG. 9 is representative of the data for each of the first 22 chromosomes; note the log scale. The number of reads varies widely from one probe to another. The plot for the last subject in FIG. 10 looks different. Note that its percentile values look the same; 95th percentile depth of read is still about 1000.

Figure 11:
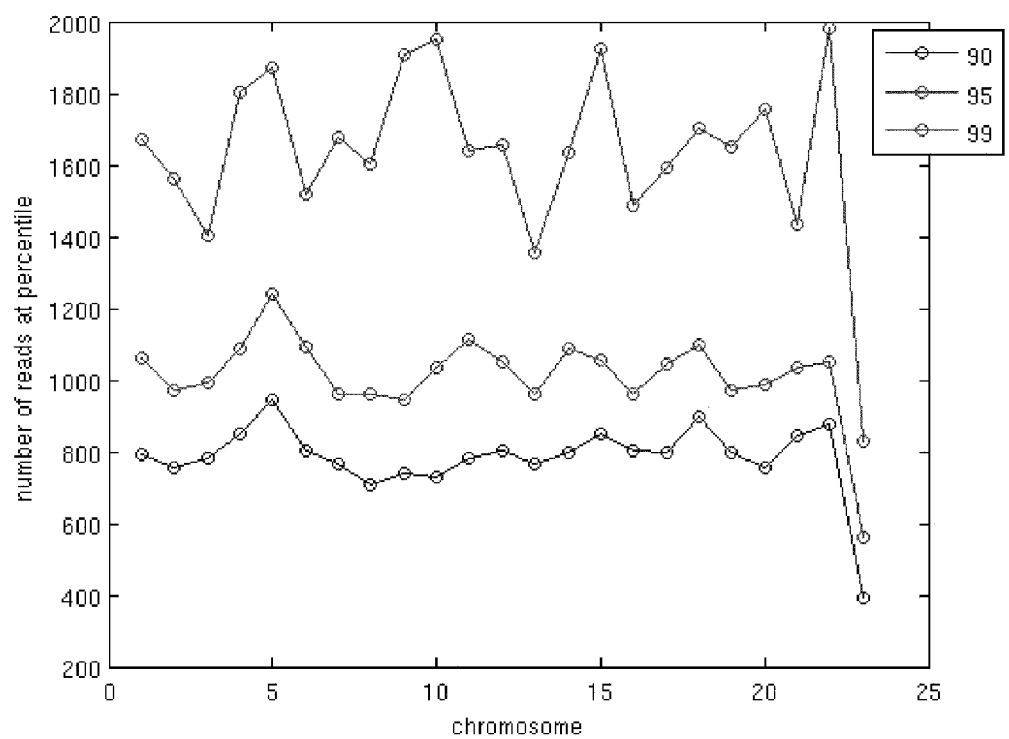
FIG. 11 shows percentiles of the sequence count distributions.
Figure 12:
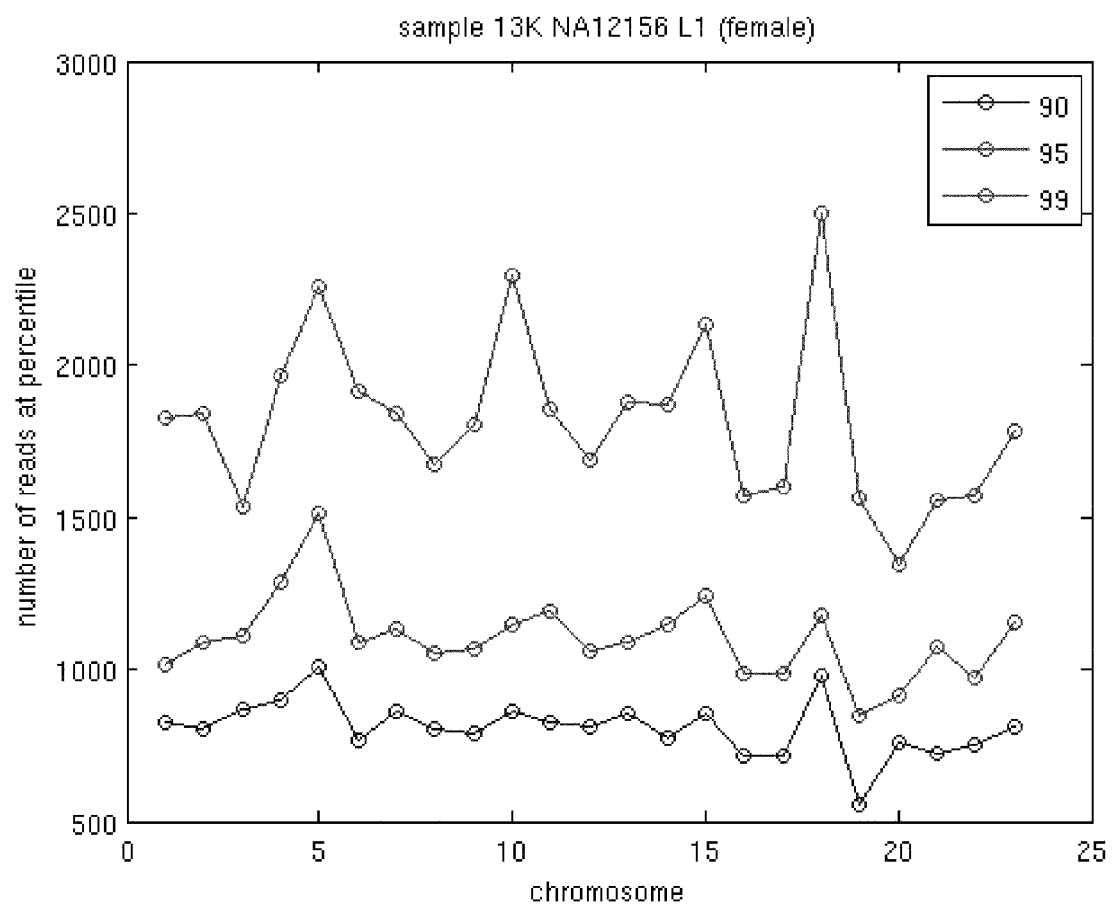
FIG. 12 shows percentiles of the sequence count distributions.

FIGS. 11 and 12 show various percentiles of the sequence count distributions as a function of the chromosome. The last chromosome shown is the X. The sample on the top is male, so the copy number for X is half that of the other chromosomes, which is clearly observable in the data. The sample on the bottom is female.

Figure 13A:
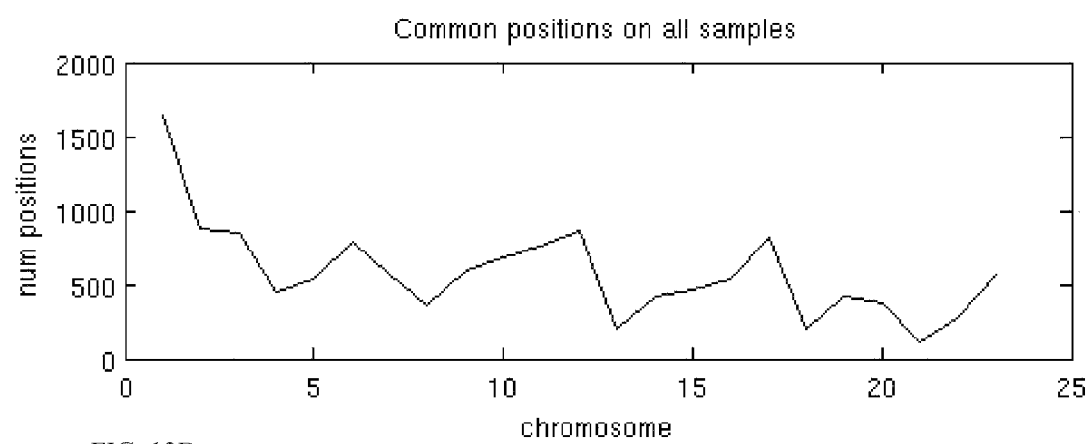
FIGS. 13A and 13B show a number of reads vs. average number of reads.
Figure 13B:
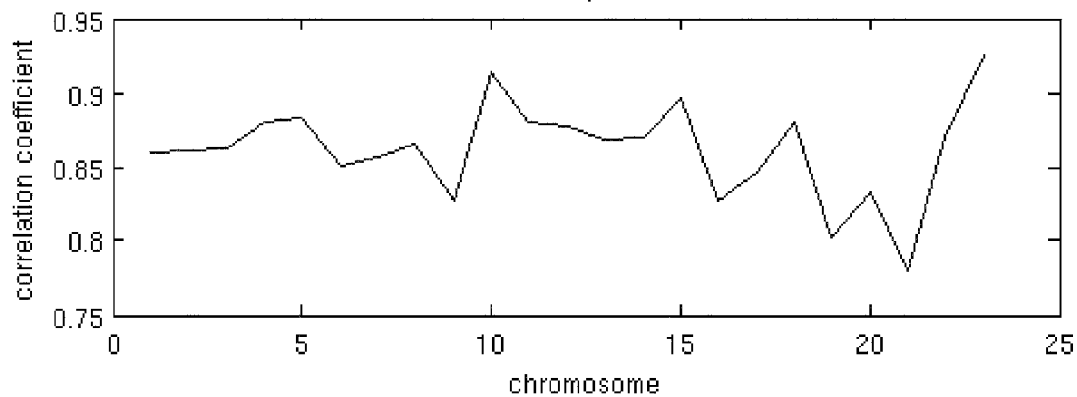

These data indicate that the number of reads for a single sample varies widely from one position to another. An important question in whether that variation is consistent across samples. If so, a model may be created for each probe for how its number of reads varies from the average number of reads, given equal copy number. FIGS. 13A and 13B consider two samples (na10851 and na12156), one chromosome at a time. The plots show the correlation coefficient between the number of reads for the two samples. The high correlation coefficient suggests that variation in the number of reads is due largely to probe characteristics rather than variation between samples. (This data shows only forward reads).

Non-Invasive Prenatal Screening Using Allele Ratios

In one embodiment of the present disclosure, the disclosed method is used to detect fetal copy number by using genetic material found in a maternal blood sample, where the maternal blood sample contains some free-floating fetal DNA. The fraction of fetal DNA compared to the mother's DNA may be unknown. In one embodiment of the present disclosure, the ratio of the identity of alleles can be used to determine the ploidy state of a fetus, as that ratio is characteristic of a given ploidy state. For example, if an individual is homogenous at a given allele, the ratio may be 1:0, if he is heterogeneous, it may be 1:1; and if he is trisomic it could be 1:0 in the case of a homogenous allele, and 2:1 in the case of a heterogeneous allele. This ratio can be hard to detect if it is in the presence of a large quantity of genetic material from another individual whose ploidy state is different from the target individual. The method described herein is one way to accomplish the ploidy determination of such an individual in such a situation. Some background for this method, including nomenclature, definitions, supporting mathematics, and other details may be found in U.S. Utility application Ser. No. 11/603,406, filed Nov. 28, 2006; U.S. Utility application Ser. No. 12/076,348, filed Mar. 17, 2008, and PCT Utility Application Serial No. PCT/US09/052,730.

Claimed herein is a method to determine the ploidy state of a fetus from the fetal genetic material found in a maternal blood sample. The method may involve obtaining a maternal blood sample, and enriching the fetal DNA. The method may involve amplifying and/or genotyping or sequencing the genetic material in the sample. It may involve using the method described herein to determine said ploidy state using data taken from the list comprising: the output of the genotyping, the sequence data, the determined allele identities, the allelic ratios, the intensities of the individual measurements, the separately measured haplotypic and/or diploid genetic data from the mother, the haploid and diploid genetic data from the father, genetic data from other related individuals, and combinations thereof.

In one embodiment of the present disclosure, the results of the ploidy determination may be used for the purpose of making a clinical decision in the context of prenatal diagnosis, where said decision may involve deciding to continue with the pregnancy, to terminate the pregnancy, to conduct further testing, and/or to make a medical intervention. The methods described herein could be used in other contexts as well, for example in archaeology, or forensics, where the goal is to determine ploidy information or other genetic information, where the genetic material from the target individual is in the presence of genetic material from other individuals.

Some of the methods described herein are discussed in the context of using MIPs and/or sequencing, though any targeting and genotyping and technology could equally well apply. The alleles of interest may be SNPs, or they may be larger regions of DNA. The goal of the methods described herein is to determine genotypic data of the target individual in the presence of other, contaminating DNA, originating from other individuals. In one embodiment of the present disclosure, the genotypic data that is desired involves the ploidy state of the target individual. In one embodiment of the present disclosure, the target DNA is fetal DNA, and thus the target individual is a gestating fetus, and where the fetal DNA is isolated, preferentially enriched, or simply measured in maternal blood or plasma, and where the maternal DNA is the genetic material from other individuals. The fetal DNA may be free floating, extracellular DNA, or it may be cellular DNA, for example, from enucleated fetal red blood cells as found in maternal blood or plasma samples. The genetic measurements of the DNA may be done using a combination of amplification methods, and genotyping methods, such as those described in the patent applications listed in this document, and may also include other methods such as rolling circle amplification, bridge sequencing, and other DNA amplification, genotyping and sequencing methods known in the art.

In some embodiments of the method, the parental genetic data may be used to increase the accuracy with which the ploidy determination may be made. In some embodiments of the method, the maternal genetic data may be used to increase the accuracy with which the ploidy determination may be made. In some embodiments, the knowledge of the maternal haplotypic genetic data may be used along with the genetic data measured from free floating DNA found in the blood to determine which haplotypes from the mother and father are present in the fetus. This knowledge may be used to determine the presence or absence of specific disease related genes, or other phenotypically correlated genes, in the genotype of the fetus. It may also be used to infer the more complete genotypic information of the fetus, specifically, allele calls, the presence of insertions, deletions, transpositions, and other genetic modifications that may correlate with diseases, conditions, or other phenotypes.

Simplified Explanation for Allele Ratio Method for Ploidy Calling in NPD

In one embodiment the ploidy state of a gestating fetus may be determined using a method that looks at allele ratios. Some methods determine fetal ploidy state by comparing numerical sequencing output DNA counts from a suspect chromosome to a reference euploid chromosome. In contrast to that concept, the allele ratio method determines fetal ploidy state by looking at allele ratios for different parental contexts on one chromosome. This method has no need to use a reference chromosome. For example, imagine the following possible ploidy states, and the allele ratios for various parental contexts:

(note: ratio 'r' is defined as follows: 1/r = fraction mother DNA/fraction fetal DNA)

| Parent context | A:B Euploidy | Child genotype | A:B P-U tri* | Child genotype | A:B P-M tri* | Child genotype |
|---|---|---|---|---|---|---|
| AA\|BB | 2 + r:r | AB | 2 + r:2r | ABB | 2 + r:2r | ABB |
| BB\|AA | r:2 + r | AB | 2 + 2r:r | AAB | 2 + 2r:r | AAB |
| AA\|AB | 1:0 | AA | 2 + 2r:r | AAB | 1:0 | AAA |
| AA\|AB | 2 + r:r | AB | — | — | 2 + 2r:r | AAB |
| AA\|AB | 4 + 2r:r | average | — | — | 4 + 4r:r | average |

*P-U tri = paternal matching trisomy; P-M tri = paternal matching trisomy;

Note that this table represents only a subset of the parental contexts and a subset of the possible ploidy states that this method is designed to differentiate. In this case, one can determine the A:B ratios for a plurality of alleles from a set of parental contexts in a set of sequencing data. One can then state a number of hypothesis for each ploidy state, and for each value of r; each hypothesis will have an expected pattern of A:B ratios for the different parental contexts. One can then determine which hypothesis best fits the experimental data.

For example, using the above set of parental contexts, and the value of r=0.2, one can rewrite the chart as follows: (For example, one can calculate [# reads of allele A/# reads of allele B]; thus 2+r:r becomes 2+0.2:0.2→2.2:0.2=11)

| Parent context | A/B Euploidy | Child genotype | A/B P-U tri* | Child genotype | A/B P-M tri* | Child genotype |
|---|---|---|---|---|---|---|
| AA\|BB | 11 | AB | 5.5 | ABB | 5.5 | ABB |
| BB\|AA | 0.91 | AB | 12 | AAB | 12 | AAB |
| AA\|AB | infinte | AA | 12 | AAB | infinite | AAA |
| AA\|AB | 11 | AB | — | — | 12 | AAB |
| AA\|AB | 21 | average | — | — | 44 | average |

Now, one can look at the ratios between the A:B ratios for different parental contexts. In this case, one may expect the $A:B_{AA|BB}/A:B_{AA|AB}$ to be 11/21=0.524 on average for euploidy; to be 5.5/12=0.458 on average for a paternal unmatched trisomy, and 5.5/44=0.125 on average for a paternal matching trisomy. The profile of A:B ratios among different contexts will be different for different ploidy states, and the profiles should be distinctive enough that it will be possible to determine the ploidy state for a chromosome with high accuracy. Note that the calculated value of r may be determined using a different method, or it can be determined using a maximum likelihood approach to this method. In one embodiment, the method requires the maternal genotypic knowledge. In one embodiment the method requires paternal genotypic knowledge. In one embodiment the method does not require paternal genotypic knowledge. In an embodiment, the percent fetal fraction and the ratio of maternal to fetal DNA are essentially equivalent, and can be used interchangeably after applying the appropriate linear algebraic transformation. In some embodiments, r=[percent fetal fraction]/[1−percent fetal fraction].

Allele Ratio Analysis at SNPs

The SNP130 database has been linked with Matlab in order to identify sequences that have SNPs in them. The goal is to determine how well the observed allele ratio reflects expected allele ratio in genotype. These are healthy adult samples, so SNPs should either be homozygous, in which case they should have a 1:0 allele ration, or heterozygous, in which case they should have a 1:1 allele ratio.

Figure 14:
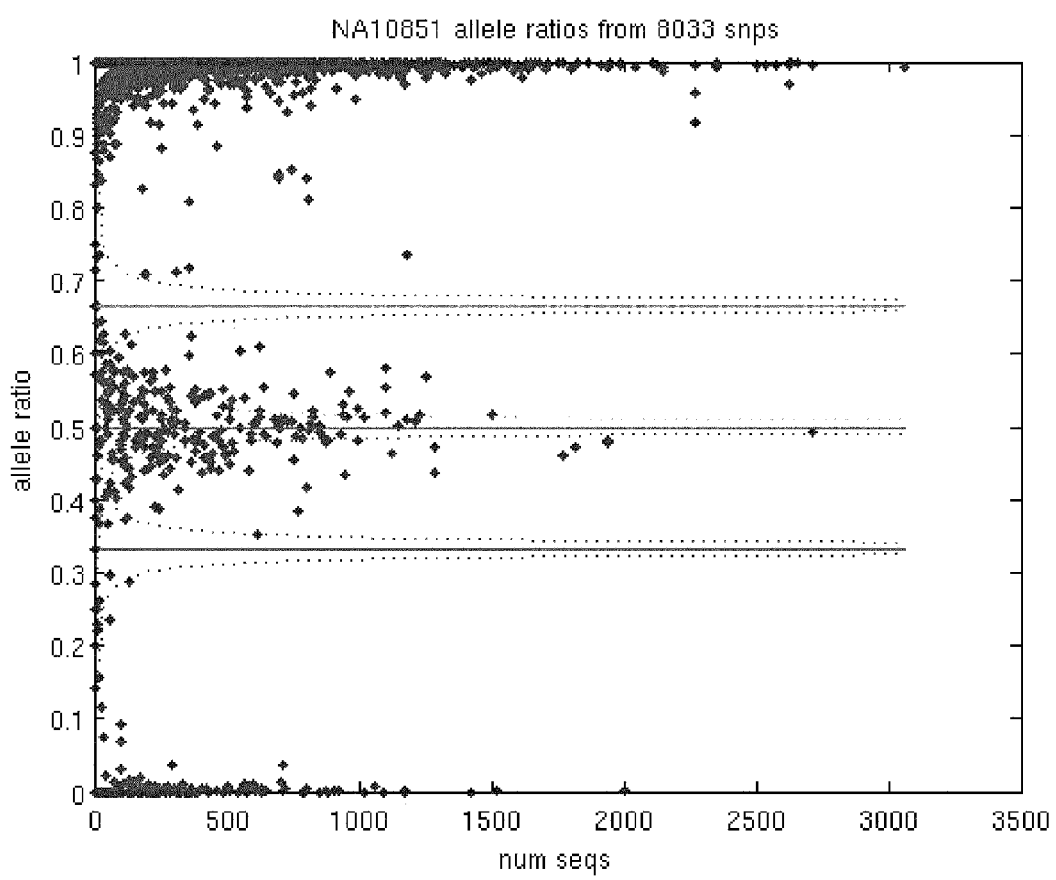
FIG. 14 shows allele ratios at SNPs versus the number of sequences.
Figure 15:
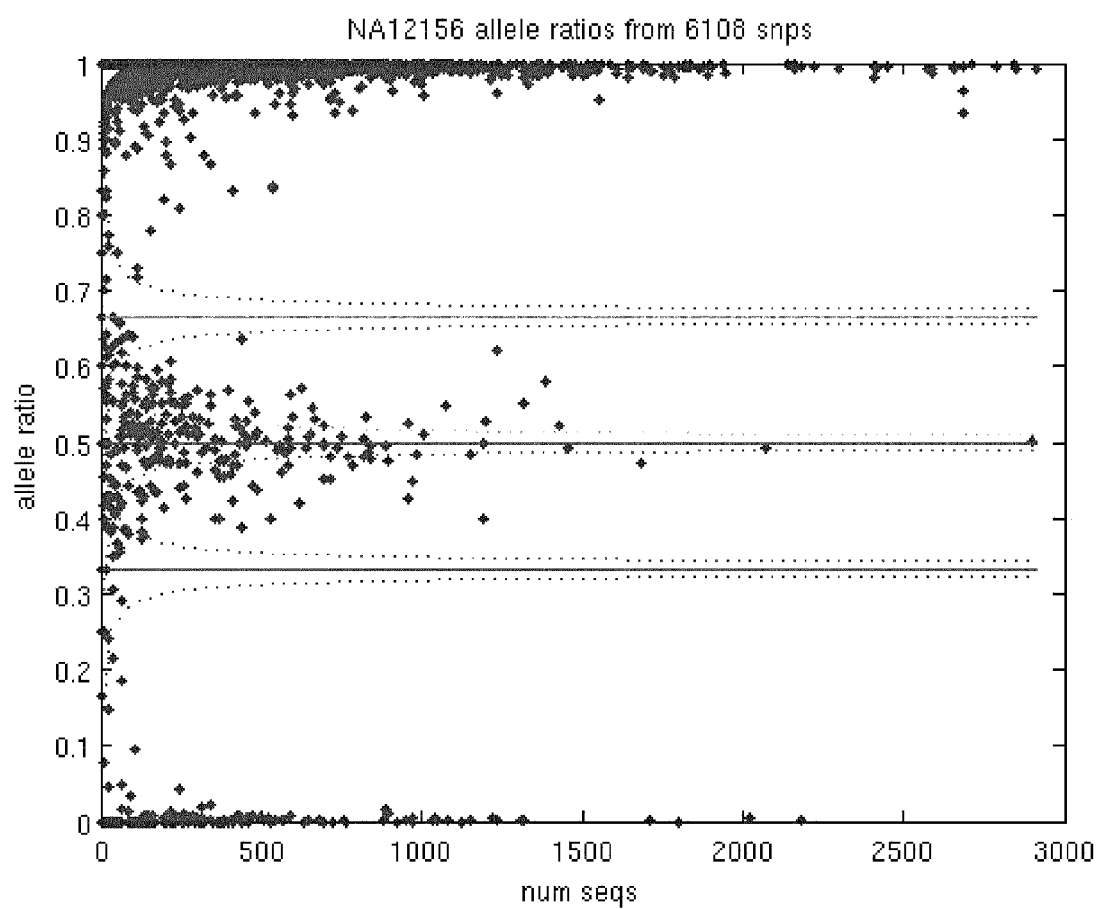
FIG. 15 shows allele ratios at SNPs versus the number of sequences.

FIGS. 14 and 15 show the allele ratios at all SNPs as a function of the number of sequences. All mapped sequences are included for which there is a base call at the SNP location (i.e., no minimum phred score is required). The dotted lines show 1-sigma bounds for the observed rate, modeling each sequence as an independent Bernoulli trial. Note that the x-axis varies between plots.

SNP Classification Using Phred Scores

The phred score, q, is defined as follows: P(wrong base call)=10^(−q/10) Let x=reference ratio of true genotype=number of reference alleles/number of total alleles. For disomy, x in {0, 0.5, 1} corresponds to {MM, RM, RR}. Let z be the allele observed in a sequence, z in {R, M}. Here the likelihood of observing z=R is shown, conditioned on the true ratio of reference alleles in the genotype (ie, what is P(z=R|x)

$$P(z=R|x)=P(z=R|gc,x)P(gc)+P(z=R|bc,x)P(bc)$$

where gc is the event of a correct call and bc is the event of a bad call.

P(gc) and P(bc) are calculated from the phred score. P(z=R|gc,x)=x and P(z=R|bc,x)=1−x, assuming that probes are unbiased.

Result, where b=P(wrong base call): P(z=R|x)=x(1−b)+(1−x)*b

Note that the probability of a reference allele measurement converges to the reference allele ratio as the phred score improves, as expected.

Assuming that each sequence is generated independently, conditioned on the true genotype, the likelihood of a set of measurements at the same SNP is simply the product of the individual likelihoods. This method accounts for varying phred scores. In another embodiment, it is possible to account for varying confidence in the sequence mapping. Given the set of n sequences for a single SNP, the combination of likelihoods results in a polynomial of order n that can be evaluated at the candidate allele ratios that represent the various hypotheses.

SNP Classification Using Phred Threshold

When a large number of sequences are available for a single SNP, the polynomial likelihood function on the allele ratio becomes intractable. An alternative is to consider only the base calls which have high phred score, and then assume that they are accurate. Each base read is now an IID Bernoulli according to the true allele ratio, and the likelihood function is Gaussian. If r is the ratio of reference reads in the data, the likelihood function on x (the true reference allele ratio) has mean=r and standard deviation=sqrt(r*(1−r)/n).

SNP Bias Correlation Across Samples

Using the two likelihood functions discussed above (polynomial, Gaussian) a SNP can be classified as RR, RM, or MM by considering the allele ratios {1, 0.5, 0}, or a maximum likelihood estimate of the allele ratio can be calculated. When the same SNP is classified as RM in two different samples, it is possible to compare the MLE estimates of the allele ratio to look for consistent "probe bias."

Figure 16:
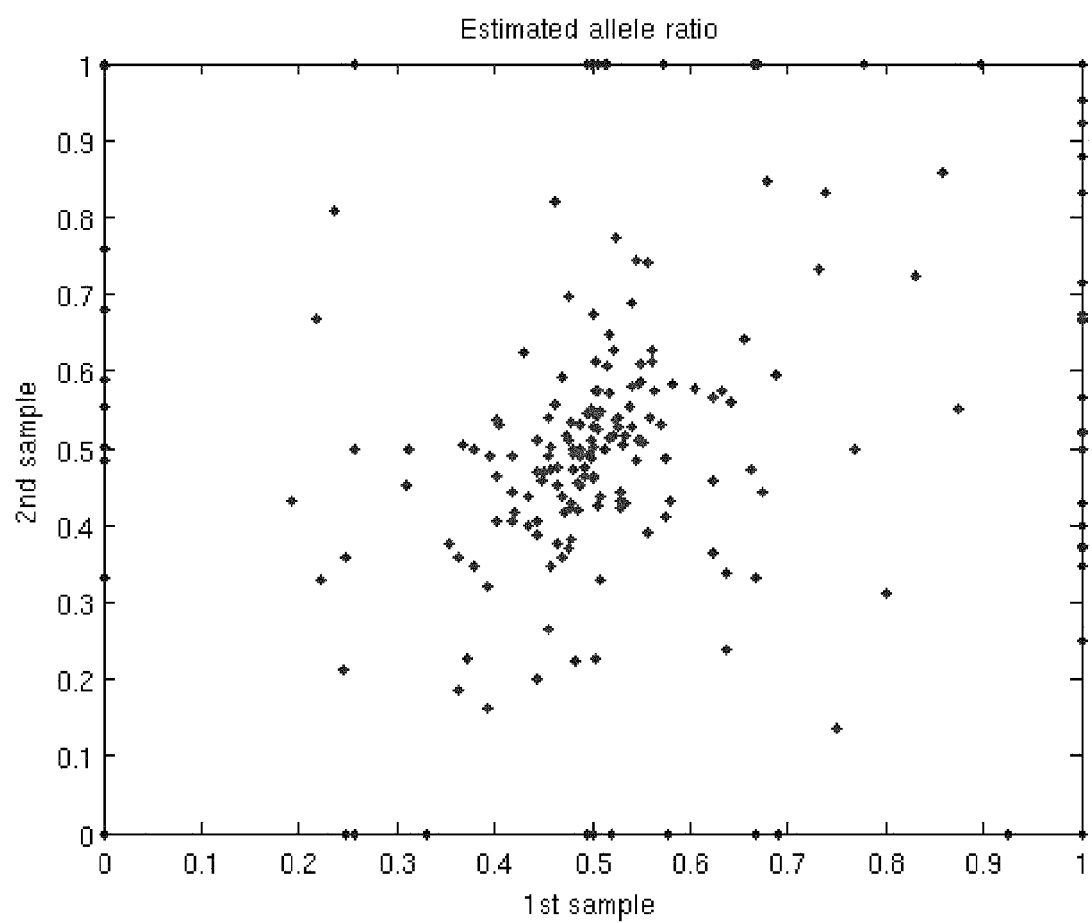
FIG. 16 shows estimated allele ratios at SNPs versus the number of sequences.

From four samples, SNPs were taken where exactly two samples are classified as RM, and plotted are the MLE allele ratios for those samples. If all probes were perfectly unbiased, the dots should be clustered at (0.5, 0.5). If the probes had perfectly consistent bias, the dots would lie along the 1:1 line, subject to some standard deviation. FIG. 16 shows 159 SNPs that were classified RM on two samples. Note that some dots lie on the perimeter of the plot, showing that the MLE estimate of the allele ratio disagrees with the classification.

Accuracy of Phred Scores

The goal here is to verify that phred scores reflect accuracy of base calls according to their definition. P(correct)=1−10^(−q/10) where q is the phred score.

Figure 17A:
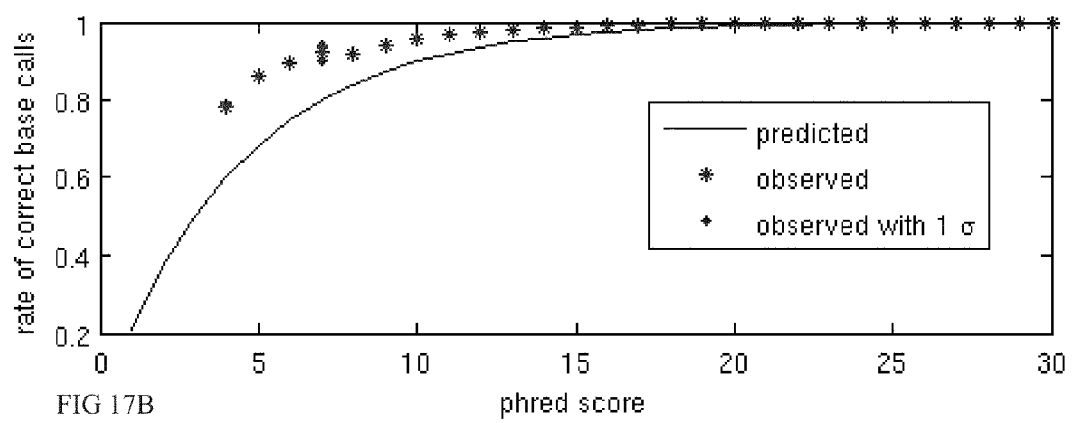
FIGS. 17A and 17B show phred scores.
Figure 17B:
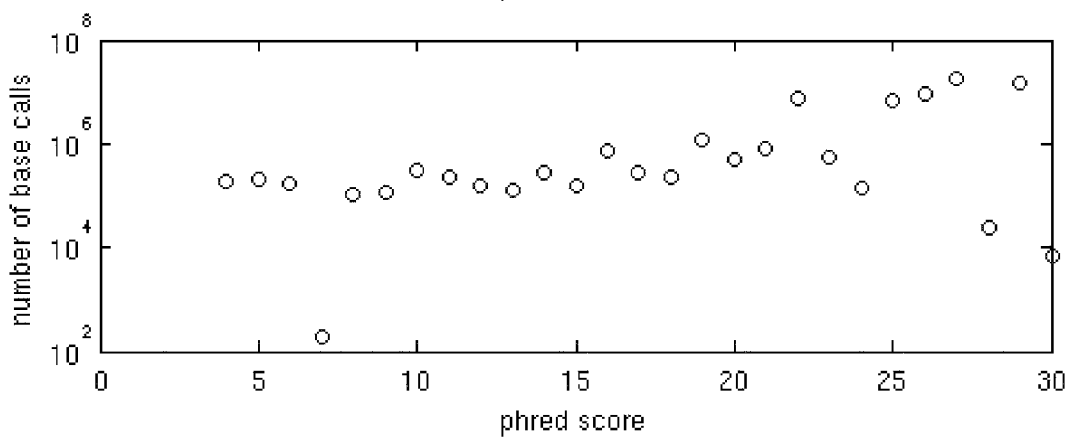

For simplicity, select sequences that do not contain a SNP. Use the reference sequence as truth. Phred scores range from 0 to 30 and are reported as integers; in this case integer bins are used. Count the number of bases in each bin, and the number of reference calls in each bin. FIG. 17A (top) shows data from chromosome 1 of one sample, a total of 63 million base calls. Bases which are "no-call" are reported with phred score=0, and therefore not included. FIG. 17B (bottom) uses an alternative definition for the phred score which was used in older versions of this sequencing platform. This prediction more closely matches the data.

These plots suggest that low phred scores may not be the best predictors of whether or not a base call is accurate. However, a high phred score is reflective of high accuracy in the base call, and there are many such calls. Therefore, one may set a threshold on phred score rather than trying to incorporate it into likelihood calculations.

Using Sequence Length as a Prior to Determine the Origin of DNA

It has been reported that the distribution of length of sequences differ for maternal and fetal DNA, with fetal generally being shorter. In one embodiment of the present disclosure, it is possible to use previous knowledge in the form of empirical data, and construct prior distribution for expected length of both mother($P(X|maternal)$) and fetal DNA ($P(X|fetal)$). Given new unidentified DNA sequence of length x, it is possible to assign a probability that a given sequence of DNA is either maternal or fetal DNA, based on prior likelihood of x given either maternal or fetal. In particular if $P(x|maternal)>P(x|fetal)$, then the DNA sequence can be classified as maternal, with $P(x|maternal)=P(x|maternal)/[(P(x|maternal)+P(x|fetal)]$, and if $p(x|maternal)<p(x|fetal)$, then the DNA sequence can be classified as fetal, $P(x|fetal)=P(x|fetal)/[(P(x|maternal)+P(x|fetal)]$. In one embodiment of the present disclosure, a distributions of maternal and fetal sequence lengths can be determined that is specific for that sample by considering the sequences that can be assigned as maternal or fetal with high probability, and then that sample specific distribution can be used as the expected size distribution for that sample.

Variable Read Depth to Minimize Sequencing Cost

In many clinical trials concerning a diagnostic, for example, in Chiu et al. BMJ 2011; 342:c7401, a protocol with a number of parameters is set, and then the same protocol is executed with the same parameters for each of the patients in the trial. In the case of determining the ploidy status of a fetus gestating in a mother using sequencing as a method to measure genetic material one pertinent parameter is the number of reads. The number of reads may refer to the number of actual reads, the number of intended reads, fractional lanes, full lanes, or full flow cells on a sequencer. In these studies, the number of reads is typically set at a level that will ensure that all or nearly all of the samples achieve the desired level of accuracy. Sequencing is currently an expensive technology, a cost of roughly $200 per 5 mappable million reads, and while the price is dropping, any method which allows a sequencing based diagnostic to operate at a similar level of accuracy but with fewer reads will necessarily save a considerable amount of money.

The accuracy of a ploidy determination is typically dependent on a number of factors, including the number of reads and the fraction of fetal DNA in the mixture. The accuracy is typically higher when the fraction of fetal DNA in the mixture is higher. At the same time, the accuracy is typically higher if the number of reads is greater. It is possible to have a situation with two cases where the ploidy state is determined with comparable accuracies wherein the first case has a lower fraction of fetal DNA in the mixture than the second, and more reads were sequenced in the first case than the second. It is possible to use the estimated fraction of fetal DNA in the mixture as a guide in determining the number of reads necessary to achieve a given level of accuracy.

In an embodiment of the present disclosure, a set of samples can be run where different samples in the set are sequenced to different reads depths, wherein the number of reads run on each of the samples is chosen to achieve a given level of accuracy given the calculated fraction of fetal DNA in each mixture. In one embodiment of the present disclosure, this may entail making a measurement of the mixed sample to determine the fraction of fetal DNA in the mixture; this estimation of the fetal fraction may be done with sequencing, it may be done with TaqMan, it may be done with qPCR, it may be done with SNP arrays, it may be done with any method that can distinguish different alleles at a given loci. The need for a fetal fraction estimate may be eliminated by including hypotheses that cover all or a selected set of fetal fractions in the set of hypotheses that are considered when comparing to the actual measured data. After the fraction fetal DNA in the mixture has been determined, the number of sequences to be read for each sample may be determined.

In one embodiment of the present disclosure, 100 pregnant women visit their respective OB's, and their blood is drawn into blood tubes with an anti-lysant. They each take home a kit for the father of their gestating fetus who gives a saliva sample. Both sets of genetic materials for all 100 couples are sent back to the laboratory, where the mother blood is spun down and the buffy coat is isolated, as well as the serum. The serum contains a mixture of maternal DNA as well as placentally derived DNA. The maternal buffy coat and the paternal blood is genotyped using a SNP array, and the DNA in the maternal plasma samples are targeted with SURESELECT hybridization probes. The DNA that was pulled down with the probes is used to generate 100 tagged libraries, one for each of the maternal samples, where each sample is tagged with a different tag. A fraction from each library is withdrawn, each of those fractions are mixed together and added to two lanes of a ILLUMINA HISEQ DNA sequencer in a multiplexed fashion, wherein each lane resulted in approximately 50 million mappable reads, resulting in approximately 100 million mappable reads on the 100 multiplexed mixtures, or approximately 1 million reads per sample. The sequence reads were used to determine the fraction of fetal DNA in each mixture. 50 of the samples had more than 15% fetal DNA in the mixture, and the 1 million reads were sufficient to determine the ploidy status of the fetuses with a 99.9% confidence.

Of the remaining mixtures, 25 had between 10 and 15% fetal DNA; a fraction of each of the relevant libraries prepped from these mixtures were multiplexed and run down one lane of the HISEQ generating an additional 2 million reads for each sample. The two sets of sequence data for each of the mixture with between 10 and 15% fetal DNA were added together, and the resulting 3 million reads per sample which were sufficient to determine the ploidy state of those fetuses with 99.9% confidence.

Of the remaining mixtures, 13 had between 6 and 10% fetal DNA; a fraction of each of the relevant libraries prepped from these mixtures were multiplexed and run down one lane of the HISEQ generating an additional 4 million reads for each sample. The two sets of sequence data for each of the mixture with between 6 and 10% fetal DNA were added together, and the resulting 5 million total reads per mixture which were sufficient to determine the ploidy state of those fetuses with 99.9% confidence.

Of the remaining mixtures, 8 had between 4 and 6% fetal DNA; a fraction of each of the relevant libraries prepped from these mixtures were multiplexed and run down one lane of the HISEQ generating an additional 6 million reads for each sample. The two sets of sequence data for each of the mixture with between 4 and 6% fetal DNA were added together, and the resulting 7 million total reads per mixture which were sufficient to determine the ploidy state of those fetuses with 99.9% confidence.

Of the remaining four mixtures, all of them had between 2 and 4% fetal DNA; a fraction of each of the relevant libraries prepped from these mixtures were multiplexed and run down one lane of the HISEQ generating an additional 12 million reads for each sample. The two sets of sequence data for each of the mixture with between 2 and 4% fetal DNA were added together, and the resulting 13 million total reads per mixture which were sufficient to determine the ploidy state of those fetuses with 99.9% confidence.

This method required six lanes of sequencing on a HISEQ machine to achieve 99.9% accuracy over 100 samples. If the same number of runs had been required for every sample, to ensure that every ploidy determination was made with a 99.9% accuracy, it would have taken 25 lanes of sequencing, and if a no-call rate or error rate of 4% was tolerated, it could have been achieved with 14 lanes of sequencing.

According to some embodiments, the congenital disorder is a malformation, neural tube defect, chromosome abnormality, Down syndrome (or trisomy 21), Trisomy 18, spina bifida, cleft palate, Tay Sachs disease, sickle cell anemia, thalassemia, cystic fibrosis, Huntington's disease, and/or fragile x syndrome. Chromosome abnormalities include, but are not limited to, Down syndrome (extra chromosome 21), Turner Syndrome (45X0) and Klinefelter's syndrome (a male with 2x chromosomes).

According to some embodiments, the malformation is a limb malformation. Limb malformations include, but are not limited to, amelia, ectrodactyly, phocomelia, polymelia, polydactyly, syndactyly, polysyndactyly, oligodactyly, brachydactyly, achondroplasia, congenital aplasia or hypoplasia, amniotic band syndrome, and cleidocranial dysostosis.

According to some embodiments, the malformation is a congenital malformation of the heart. Congenital malformations of the heart include, but are not limited to, patent ductus arteriosus, atrial septal defect, ventricular septal defect, and tetralogy of fallot.

According to some embodiments, the malformation is a congenital malformation of the nervous system. Congenital malformations of the nervous system include, but are not limited to, neural tube defects (e.g., spina bifida, meningocele, meningomyelocele, encephalocele and anencephaly), Arnold-Chiari malformation, the Dandy-Walker malformation, hydrocephalus, microencephaly, megencephaly, lissencephaly, polymicrogyria, holoprosencephaly, and agenesis of the corpus callosum.

According to some embodiments, the malformation is a congenital malformation of the gastrointestinal system. Congenital malformations of the gastrointestinal system include, but are not limited to, stenosis, atresia, and imperforate anus.

According to some embodiments, the systems, methods, and techniques of the present disclosure are used in methods to increase the probability of implanting an embryo obtained by in vitro fertilization that is at a reduced risk of carrying a predisposition for a genetic disease.

According to some embodiments, the genetic disease is either monogenic or multigenic. Genetic diseases include, but are not limited to, Bloom Syndrome, Canavan Disease, Cystic fibrosis, Familial Dysautonomia, Riley-Day syndrome, Fanconi Anemia (Group C), Gaucher Disease, Glycogen storage disease 1a, Maple syrup urine disease, Mucolipidosis IV, Niemann-Pick Disease, Tay-Sachs disease, Beta thalessemia, Sickle cell anemia, Alpha thalessemia, Beta thalessemia, Factor XI Deficiency, Friedreich's Ataxia, MCAD, Parkinson disease—juvenile, Connexin26, SMA, Rett syndrome, Phenylketonuria, Becker Muscular Dystrophy, Duchennes Muscular Dystrophy, Fragile X syndrome, Hemophilia A, Alzheimer dementia—early onset, Breast/Ovarian cancer, Colon cancer, Diabetes/MODY, Huntington disease, Myotonic Muscular Dystrophy, Parkinson Disease—early onset, Peutz-Jeghers syndrome, Polycystic Kidney Disease, Torsion Dystonia.

In some embodiments, the method may further comprise administering prenatal or post-natal treatments for the congenital disorder. In some embodiments, the method may further comprise determining whether the fetus is likely to be afflicted with a malformation. In some embodiments, the method may further comprise administering prenatal or post-natal treatments for the malformation. In some embodiments, the method may further comprise determining whether the fetus is likely to be afflicted with a genetic disease. In some embodiments, the method may further comprise administering prenatal or post-natal treatments for the genetic disease. In some embodiments, the prenatal or post-natal treatment is taken from the group comprising pharmaceutical based intervention, surgery, genetic therapy, nutritional therapy, or combinations thereof. In some embodiments, the method may further comprise generating a report containing information pertaining to the determination. In some embodiments, the report may contain information pertaining to the determination as determined in any preceding or subsequent claim. In some embodiments, the method may further comprise generating a report containing the likelihood of a fetus displaying a phenotype, wherein the likelihood of the fetus displaying the phenotype was estimated using the determination as determined in any preceding or subsequent claim. In some embodiments, the method may further comprise performing a pregnancy termination.

Note that it has been demonstrated that DNA that originated from cancer that is living in a host can be found in the blood of the host. In the same way that genetic diagnoses can be made from the measurement of mixed DNA found in maternal blood, genetic diagnoses can equally well be made from the measurement of mixed DNA found in host blood. The genetic diagnoses may include aneuploidy states, or gene mutations. Any claim in that patent that reads on determining the ploidy state or genetic state of a fetus from the measurements made on maternal blood can equally well read on determining the ploidy state or genetic state of a cancer from the measurements on host blood.

In some embodiments, the method may allow one to determine the ploidy status of a cancer, the method comprising obtaining a mixed sample that contains genetic material from the host, and genetic material from the cancer, measuring the DNA in the mixed sample, calculating the fraction of DNA that is of cancer origin in the mixed sample, and determining the ploidy status of the cancer using the measurements made on the mixed sample and the calculated fraction. In some embodiments, the method may further comprise administering a cancer therapeutic based on the determination of the ploidy state of the cancer. In some embodiments, the method may further comprise administering a cancer therapeutic based on the determination of the ploidy state of the cancer, wherein the cancer therapeutic is taken from the group comprising a pharmaceutical, a biologic therapeutic, and antibody based therapy and combination thereof.

Context Optimization

A method which can provide more information for a given number of reads, or alternately, require a fewer number of reads for a given level of accuracy, is to focus on reads that cover SNPs, where the context of the parents are known at that SNP. Furthermore, there are a number of methods, such as circularizing probes or capture probes, for targeting specific SNPs that can enhance the number of reads that map to those SNPs. In a targeted approach to sequencing maternal plasma the question then becomes, which SNPs should one target? In general, the most informative context is AA|BB, because for every such SNP, the child will be AB, and the measurements of the B allele will not be contaminated by maternal DNA. The second most informative context is AA|AB, because half of the fetal alleles in that context will be AB. In the AA|BB context, there is a 100% chance that there is a fetal allele that is a HISNP. In the AA|AB context, there is a 50% chance that there is a fetal allele that is a HISNP. The remaining three contexts are of different levels of informativeness for given situations. Note, for reasons of symmetry, the nine contexts can be collapsed into five; e.g. AB|AA is effectively the same as AB|AA)

In one embodiment of the present disclosure, a method is presented for selecting SNPs for targeting that maximizes the chance of obtaining maximally informative SNPs. In one embodiment of the present disclosure, the set of SNPs with the highest minor allele frequency are selected for targeting. The maximum minor allele frequency possible is 50%. From a set of SNPs with known minor allele frequencies, those with the highest minor allele frequency may be selected. In some embodiments of the present disclosure, the SNPs are selected where the parent contexts maximize the chance that the fetus will have a HISNP at that locus. Note that when no apriori knowledge of the actual parental contexts is available, those loci with the highest minor allele frequency will result in the maximal likelihood of the fetus having a HISNP at that allele. In cases where the mother's genotype is known, one may choose those alleles that are homozygous, since only when a maternal context is homozygous is it possible for the fetus to have a HISNP. If the father's genotype is known, those loci may be chosen where the father's context is homozygous for allele that is the minor allele in the population. Alternately, those loci may be chosen where the paternal context is heterozygous. In the case where the parental genotypes are both known, those loci may be chosen that are from the AA|BB context. Alternately, those loci may be chosen that are from the AA|AB context.

In some cases, three alleles may have some frequency in the population, (e.g. A, T and G). In some embodiments of the present disclosure, the set of SNPs where the sum of the minor allele frequencies are greatest are selected for targeting. In some embodiments of the present disclosure, the set of SNPs for targeting is selected by selecting loci that maximize the chance that the fetus will have a HISNP at that locus. Note that a locus where the allele frequencies that are 60%/40% will not be as likely to result in a fetal allele that is a HISNP as a context that is, for example, 60%/30%/10%.

In some cases, different populations may have different allele frequencies. In cases where there is no a priori knowledge of the parental genotypes, but the parents are from different population groups where those two populations have different allele frequencies at some loci, then it is possible to choose loci to target that provide a greater likelihood of the fetus having a HISNP that by using one overall population allele frequency model.

In a case where the two parents are of a different ethnicity, one way to maximize the likelihood of a given SNP being from a highly informative parental context is to choose a set of SNPs where the heterozygosity is as low as possible but different from one another. For example, if the mother is Caucasian and the father is Asian, and within the Caucasian population the SNP has a frequency of 40% T and 60% G, and within the Asian population the SNP has a frequency of 60% T and 40% G, then the frequency of the parental context is AA|BB at that SNP is greater than 1/8.

Imagine a couple from two different population groups, and two sets of loci where the minor allele frequency is as follows for the two population groups: locus set #1: 0.5 and 0.3, locus set #2: 0.4 and 0.4? The (0.5/0.3) locus set will contain, on average, 14.5% of SNPs with the AA|BB parental context, while the (0.4/0.4) locus set will contain, on average, 11.52% of SNPs with the AA|BB parental context. At the same time, the (0.5/0.3) locus set will contain, on average, 21.0% of SNPs with the AA|AB parental context, while the (0.4/0.4) locus set will contain, on average, 25.0% of SNPs with the AA|AB parental context. Since the AA|BB context always results in a HISNP, and the AA|AB context results in a HISNP half of the time, the (0.5/0.3) locus set will contain, on average, 25.0% fetal HISNP, and the (0.4/0.4) locus set will contain, on average, 24.0% fetal HISNPs. In one embodiment of the present disclosure, one may select SNPs for targeting in which heterozygosity rate (a term which is used here interchangeably with the term minor allele frequency) among the father's population is maximized, but the minor allele frequency among the mother's population group is minimized.

Using Raw Genotyping Data

There are a number of methods that can accomplish NPD using fetal genetic information measured on fetal DNA found in maternal blood. Some of these methods involve making measurements of the fetal DNA using SNP arrays, some methods involve untargeted sequencing, and some methods involve targeted sequencing. The targeted sequencing may target SNPs, it may target STRs, it may target other loci, or is may target some combination of those loci. In some of these methods, the method may involve using a commercial or proprietary allele caller than calls the identity of the alleles from the intensity data that comes from the sensors in the machine doing the measuring. For example, the ILLUMINA INFINIUM system or the AFFYMETRIX GENECHIP microarray system involves beads or microchips with attached DNA sequences that can hybridize to complementary segments of DNA. There are also sequencing methods, for example the ILLUMINA SOLEXA GENOME SEQUENCER or the ABI SOLID GENOME SEQUENCER, wherein the genetic sequence of fragments of DNA are sequenced. In all of these methods the genotypic or sequencing data is typically determined on the basis of fluorescent signals (or the lack thereof). These systems typically are combined with low level software packages that make specific allele calls (secondary genetic data) from the analog output of the fluorescent or other detection device (primary genetic data). For example, in the case of a given allele on a SNP array, the software will make a call, for example, that a certain SNP is present or not present if the fluorescent intensity is measure above or below a certain threshold. Similarly, the output of a sequencer is a chromatogram that indicates the level of fluorescence detected for each of the dyes, and the software will make a call that a certain base pair is A or T or C or G. High throughput sequencers typically make a series of such measurements, called a read, that represents the most likely structure of the DNA sequence that was sequenced. The direct analog output of the chromatogram is defined here to be the primary genetic data, and the base pair/SNP calls made by the software are considered here to be the secondary genetic data. In one embodiment, primary data refers to the raw intensity data that is the unprocessed output of a genotyping platform, where the genotyping platform may refer to a SNP array, or to a sequencing platform. The secondary genetic data refers to the processed genetic data, where an allele call has been made, or the sequence data has been assigned base pairs, and/or the sequence reads have been mapped to the genome.

Many higher level applications take advantage of these allele calls, SNP calls and sequence reads, that is, the secondary genetic data, that the genotyping software produces. For example, DNA NEXUS, ELAND or MAQ will take the sequencing reads and map them to the genome. For example, in the context of non-invasive prenatal diagnosis, complex informatics, such as PARENTAL SUPPORT™, may leverage a large number of SNP calls to determine the genotype of an individual. Also, in the context of preimplantation genetic diagnosis, it is possible to take a set of sequence reads that are mapped to the genome, and by taking a normalized count of the reads that are mapped to each chromosome, or section of a chromosome, it may be possible to determine the ploidy state of an individual. In the context of non-invasive prenatal diagnosis it may be possible to take a set of sequence reads that have been measured on DNA present in maternal serum, and map them to the genome. One may then take a normalized count of the reads that are mapped to each chromosome, or section of a chromosome, and use that data to determine the ploidy state of an individual. For example, it may be possible to conclude that those chromosomes that have a disproportionately large number of reads are trisomic in the fetus that is gestating in the mother from which the blood was drawn.

However, in reality, the output of the measuring instruments is an analog signal. When a certain base pair is called by the software that is associated with the sequencing software, for example the software may call the base pair a T, in reality the call is the call that the software believes to be most likely. In some cases, however, the call may be of low confidence, for example, the analog signal may indicate that the particular base pair is only 90% likely to be a T, and 10% likely to be an A. In another example, the genotype calling software that is associated with a SNP array reader may call a certain allele to be GG. However, in reality, the underlying analog signal may indicate that it is only 90% likely that the allele is GG, and 10% likely that the allele is GT. In these cases, when the higher level applications use the genotype calls and sequence calls made by the lower level software, they are losing some information. That is, the primary genetic data, as measured directly by the genotyping platform, may be messier than the secondary genetic data that is determined by the attached software packages, but it contains more information. In mapping the secondary genetic data sequences to the genome, many reads are thrown out because some bases are not read with enough clarity and or mapping is not clear. When the primary genetic data sequence reads are used, all or many of those reads that may have been thrown out when first converted to secondary genetic data sequence read can be used by treating the reads in a probabilistic manner.

In one embodiment of the present disclosure, the higher level software does not rely on the allele calls, SNP calls, or sequence reads that are determined by the lower level software. Instead, the higher level software bases its calculations on the analog signals directly measured from the genotyping platform. In one embodiment of the present disclosure, an informatics based method such as PARENTAL SUPPORT™ is modified so that its ability to reconstruct the genetic data of the embryo/fetus/child is engineered to directly use the primary genetic data as measured by the genotyping platform. In one embodiment of the present disclosure, an informatics based method such as PARENTAL SUPPORT™ is able to make allele calls, and/or chromosome copy number calls using primary genetic data, and not using the secondary genetic data. In one embodiment of the present disclosure, all genetic calls, SNPs calls, sequence reads, sequence mapping is treated in a probabilistic manner by using the raw intensity data as measured directly by the genotyping platform, rather than converting the primary genetic data to secondary genetic calls.

In some embodiments, the method can increase the accuracy of genetic data of a target individual which incorporates genetic data of at least one related individual, the method comprising obtaining primary genetic data specific to a target individual's genome and genetic data specific to the genome(s) of the related individual(s), creating a set of one or more hypotheses concerning which segments of which chromosomes from the related individual(s) correspond to those segments in the target individual's genome, determining the probability of each of the hypotheses given the target individual's primary genetic data and the related individual(s)'s genetic data, and using the probabilities associated with each hypothesis to determine the most likely state of the actual genetic material of the target individual. In some embodiments, the method can determining the number of copies of a segment of a chromosome in the genome of a target individual, the method comprising creating a set of copy number hypotheses about how many copies of the chromosome segment are present in the genome of a target individual, incorporating primary genetic data from the target individual and genetic information from one or more related individuals into a data set, estimating the characteristics of the platform response associated with the data set, where the platform response may vary from one experiment to another, computing the conditional probabilities of each copy number hypothesis, given the data set and the platform response characteristics, and determining the copy number of the chromosome segment based on the most probable copy number hypothesis. In one embodiment, the method can determine a ploidy state of at least one chromosome in a target individual, the method comprising obtaining primary genetic data from the target individual and from one or more related individuals, creating a set of at least one ploidy state hypothesis for each of the chromosomes of the target individual, using one or more expert techniques to determine a statistical probability for each ploidy state hypothesis in the set, for each expert technique used, given the obtained genetic data, combining, for each ploidy state hypothesis, the statistical probabilities as determined by the one or more expert techniques, and determining the ploidy state for each of the chromosomes in the target individual based on the combined statistical probabilities of each of the ploidy state hypotheses. In one embodiment, the method can determine an allelic state in a set of alleles, in a target individual, and from one or both parents of the target individual, and optionally from one or more related individuals, the method comprising obtaining primary genetic data from the target individual, and from the one or both parents, and from any related individuals, creating a set of at least one allelic hypothesis for the target individual, and for the one or both parents, and optionally for the one or more related individuals, where the hypotheses describe possible allelic states in the set of alleles, determining a statistical probability for each allelic hypothesis in the set of hypotheses given the obtained genetic data, and determining the allelic state for each of the alleles in the set of alleles for the target individual, and for the one or both parents, and optionally for the one or more related individuals, based on the statistical probabilities of each of the allelic hypotheses.

In some embodiments, the genetic data of the mixed sample may comprise sequence data wherein the sequence data may not uniquely map to the human genome. In some embodiments, the genetic data of the mixed sample may comprise sequence data wherein the sequence data maps to a plurality of locations in the genome, wherein each possible mapping is associated with a probability that the given mapping is correct. In some embodiments, the sequence reads are not assumed to be associated with a particular position in the genome. In some embodiments, the sequence reads are associated with a plurality of positions in the genome, and an associated probability belonging to that position.

Combining Methods of Prenatal Diagnosis

There are many methods that may be used for prenatal diagnosis or prenatal screening of aneuploidy or other genetic defects. Described elsewhere in this document, and in U.S. Utility application Ser. No. 11/603,406, filed Nov. 28, 2006; U.S. Utility application Ser. No. 12/076,348, filed Mar. 17, 2008, and PCT Utility Application Serial No. PCT/S09/52730 is one such method that uses the genetic data of related individuals to increase the accuracy with which genetic data of a target individual, such as a fetus, is known, or estimated. Other methods used for prenatal diagnosis involve measuring the levels of certain hormones in maternal blood, where those hormones are correlated with various genetic abnormalities. An example of this is called the triple test, a test wherein the levels of several (commonly two, three, four or five) different hormones are measured in maternal blood. In a case where multiple methods are used to determine the likelihood of a given outcome, where none of the methods are definitive in and of themselves, it is possible to combine the information given by those methods to make a prediction that is more accurate than any of the individual methods. In the triple test, combining the information given by the three different hormones can result in a prediction of genetic abnormalities that is more accurate than the individual hormone levels may predict.

Disclosed herein is a method for making more accurate predictions about the genetic state of a fetus, specifically the possibility of genetic abnormalities in a fetus, that comprises combining predictions of genetic abnormalities in a fetus where those predictions were made using a variety of methods. A "more accurate" method may refer to a method for diagnosing an abnormality that has a lower false negative rate at a given false positive rate. In a favored embodiment of the present disclosure, one or more of the predictions are made based on the genetic data known about the fetus, where the genetic knowledge was determined using the PARENTAL SUPPORT™ method, that is, using genetic data of individual related to the fetus to determine the genetic data of the fetus with greater accuracy. In some embodiments the genetic data may include ploidy states of the fetus. In some embodiments, the genetic data may refer to a set of allele calls on the genome of the fetus. In some embodiments some of the predictions may have been made using the triple test. In some embodiments, some of the predictions may have been made using measurements of other hormone levels in maternal blood. In some embodiments, predictions made by methods considered diagnoses may be combined with predictions made by methods considered screening. In some embodiments, the method involves measuring maternal blood levels of alpha-fetoprotein (AFP). In some embodiments, the method involves measuring maternal blood levels of unconjugated estriol ($UE_3$). In some embodiments, the method involves measuring maternal blood levels of beta human chorionic gonadotropin (beta-hCG). In some embodiments, the method involves measuring maternal blood levels of invasive trophoblast antigen (ITA). In some embodiments, the method involves measuring maternal blood levels of inhibin. In some embodiments, the method involves measuring maternal blood levels of pregnancy-associated plasma protein A (PAPP-A). In some embodiments, the method involves measuring maternal blood levels of other hormones or maternal serum markers. In some embodiments, some of the predictions may have been made using other methods. In some embodiments, some of the predictions may have been made using a fully integrated test such as one that combines ultrasound and blood test at around 12 weeks of pregnancy and a second blood test at around 16 weeks. In some embodiments, the method involves measuring the fetal nuchal translucency (NT). In some embodiments, the method involves using the measured levels of the aforementioned hormones for making predictions. In some embodiments the method involves a combination of the aforementioned methods.

Combining the Predictions

There are many ways to combine the predictions, for example, one could convert the hormone measurements into a multiple of the median (MoM) and then into likelihood ratios (LR). Similarly, other measurements could be transformed into LRs using the mixture model of NT distributions. The LRs for NT and the biochemical markers could be multiplied by the age and gestation-related risk to derive the risk for various conditions, such as trisomy 21. Detection rates (DRs) and false-positive rates (FPRs) could be calculated by taking the proportions with risks above a given risk threshold.

Another method could involve a situation with four measured hormone levels, where the probability distribution around those hormones is known: $p(x_1, x_2, x_3, x_4|e)$ for the euploid case and $p(x_1, x_2, x_3, x_4|a)$ for the aneuploid case. Then one could measure the probability distribution for the DNA measurements, $g(y|e)$ and $g(y|a)$ for the euploid and aneuploid cases respectively. Assuming they are independent given the assumption of euploid/aneuploid, one could combine as $p(x_1, x_2, x_3, x_4|a)g(y|a)$ and $p(x_1, x_2, x_3, x_4|e)g(y|e)$ and then multiply each by the prior $p(a)$ and $p(e)$ given the maternal age. One could then choose the one that is highest. In one embodiment it is possible to evoke central limit theorem to assume distribution on $g(y|a$ or $e)$ is Gaussian, and measure mean and standard deviation by looking at multiple samples. In another embodiment, one could assume they are not independent given the outcome and collect enough samples to estimate the joint distribution $p(x_1, x_2, x_3, x_4|a$ or $e)$.

In one embodiment, the ploidy state for the target individual is determined to be the ploidy state that is associated with the hypothesis whose probability is the greatest. In some cases, one hypothesis will have a normalized, combined probability greater than 90%. Each hypothesis is associated with one, or a set of, ploidy states, and the ploidy state associated with the hypothesis whose normalized, combined probability is greater than 90%, or some other threshold value, such as 50%, 80%, 95%, 98%, 99%, or 99.9%, may be chosen as the threshold required for a hypothesis to be called as the determined ploidy state.

Free-Floating DNA of Children from Previous Pregnancies in Maternal Blood

One difficulty to non-invasive prenatal diagnosis is differentiating DNA in the maternal blood from the current pregnancy and from previous pregnancies. Some believe that genetic matter from prior pregnancies will go away after some time, but conclusive evidence has not been shown. In one embodiment of the present disclosure, it is possible to determine fetal DNA present in the maternal blood of paternal origin (that is, DNA that the fetus inherited from the father) using the PARENTAL SUPPORT™ (PS) method, and the knowledge of the paternal genome. This may utilize phased parental genetic information. It is possible to phase the parental genotype from unphased genotypic information using grandparental genetic data (such as measured genetic data from a sperm from the grandfather), or genetic data from other born children, or a sample of a miscarriage. One could also phase unphased genetic information by way of a HapMap-based phasing, or a haplotyping of paternal cells. Successful haplotyping has been demonstrated by arresting cells at phase of mitosis when chromosomes are tight bundles and using microfluidics to put separate chromosomes in separate wells. In another embodiment it is possible to use the phased parental haplotypic data to detect the presence of more than one homolog from the father, implying that the genetic material from more than one child is present in the blood. By focusing on chromosomes that are expected to be euploid in a fetus, one could rule out the possibility that the fetus was afflicted with a trisomy. Also, it is possible to determine if the fetal DNA is not from the current father, in which case one could use other methods such as the triple test to predict genetic abnormalities.

Non-Invasive Gender Determinations

The methods described herein can be used for non-invasive gender determination at a very early gestational age, for example as early as four week, as early as five weeks, as early as six weeks, as early as seven weeks, as early as eight weeks, as early as nine weeks, as early as ten weeks, as early as eleven weeks, and as early as twelve weeks.

Determining Whether Fetal Cells in Maternal Blood are from the Current Pregnancy Non-invasive prenatal diagnosis involves the ability to determine the genetic state of a gestating fetus using non-invasive methods. Typically, this involves a blood draw from the mother, and the use of genetic material from the mother that may be found in the maternal blood, or some portion of the maternal blood. There may be other sources of fetal genetic material available via methods other than a blood draw. In the case of the fetal genetic material available in maternal blood, there are two main categories: (1) whole fetal cells, for example, nucleated fetal red blood cells, and (2) free floating fetal DNA. In the case of whole fetal cells, there is some evidence that fetal cells can persist in maternal blood for an extended period of time such that it is possible to isolate a cell from a pregnant woman that contains the DNA from a child or fetus from a prior pregnancy. There is also evidence that the free floating fetal DNA is cleared from the system in a matter of weeks.

One challenge is how to determine the identity of the individual whose genetic material is contained in the cell, namely to ensure that the measured genetic material is not from a fetus from a prior pregnancy. In one embodiment of the present disclosure, the knowledge of the maternal genetic material can be used to ensure that the genetic material in question is not maternal genetic material. There are a number of methods to accomplish this end, including informatics based methods such as PARENTAL SUPPORT™, as described in this document or any of the patents referenced in this document.

In one embodiment of the present disclosure, the blood drawn from the pregnant mother may be separated into a fraction containing free floating fetal DNA, and a fraction containing nucleated red blood cells. The free floating DNA may optionally be enriched, and the genotypic information of the DNA may be measured. From the measured genotypic information from the free floating DNA, the knowledge of the maternal genotype may be used to determine aspects of the fetal genotype. These aspects may refer to ploidy state, and/or a set of allele identities. Then, individual nucleated red blood cells may be genotyped using methods described elsewhere in this document, and other referent patents, especially those mentioned in the first section of this document. The knowledge of the maternal genome would allow one to determine whether or not any given single blood cell is genetically maternal. And the aspects of the fetal genotype that were determined as described above would allow one to determine if the single blood cell is genetically derived from the fetus that is currently gestating. In essence, this aspect of the present disclosure allows one to use the genetic knowledge of the mother, and possibly the genetic information from other related individuals, such as the father, along with the measured genetic information from the free floating DNA found in maternal blood to determine whether an isolated nucleated cell found in maternal blood is either (a) genetically maternal, (b) genetically from the fetus currently gestating, or (c) genetically from a fetus from a prior pregnancy.

Some Embodiments

In some embodiments of the present disclosure, a method for determining the ploidy state of one or more chromosome in a target individual may include any of the following steps, and combinations thereof:

Amplification of the DNA, a process which transforms a small amount of genetic material to a larger amount of genetic material that contains a similar set of genetic data, can be done by a wide variety of methods, including, but not limited to, Polymerase Chain Reaction (PCR), ligand mediated PCR, degenerative oligonucleotide primer PCR, Multiple Displacement Amplification, allele-specific amplification techniques, Molecular Inversion Probes (MIP), padlock probes, other circularizing probes, and combination thereof. Many variants of the standard protocol may be used, for example increasing or decreasing the times of certain steps in the protocol, increasing or decreasing the temperature of certain steps, increasing or decreasing the amounts of various reagents, etc. The DNA amplification transforms the initial sample of DNA into a sample of DNA that is similar in the set of sequences, but of much greater quantity. In some cases, amplification may not be required.

The genetic data of the target individual and/or of the related individual can be transformed from a molecular state to an electronic state by measuring the appropriate genetic material using tools and or techniques taken from a group including, but not limited to: genotyping microarrays, and high throughput sequencing. Some high throughput sequencing methods include Sanger DNA sequencing, pyrosequencing, the ILLUMINA SOLEXA platform, ILLUMINA's GENOME ANALYZER, or APPLIED BIOSYSTEM's 454 sequencing platform, HELICOS's TRUE SINGLE MOLECULE SEQUENCING platform, HALCYON MOLECULAR's electron microscope sequencing method, or any other sequencing method. All of these methods physically transform the genetic data stored in a sample of DNA into a set of genetic data that is typically stored in a memory device en route to being processed.

Any relevant individual's genetic data can be measured by analyzing substances taken from a group including, but not limited to: the individual's bulk diploid tissue, one or more diploid cells from the individual, one or more haploid cells from the individual, one or more blastomeres from the target individual, extra-cellular genetic material found on the individual, extra-cellular genetic material from the individual found in maternal blood, cells from the individual found in maternal blood, one or more embryos created from (a) gamete(s) from the related individual, one or more blastomeres taken from such an embryo, extra-cellular genetic material found on the related individual, genetic material known to have originated from the related individual, and combinations thereof.

In some embodiments, a set of at least one ploidy state hypothesis may be created for each of the chromosomes of interest of the target individual. Each of the ploidy state hypotheses may refer to one possible ploidy state of the chromosome or chromosome segment of the target individual. The set of hypotheses may include some or all of the possible ploidy states that the chromosome of the target individual may be expected to have. Some of the possible ploidy states may include nullsomy, monosomy, disomy, uniparental disomy, euploidy, trisomy, matching trisomy, unmatching trisomy, maternal trisomy, paternal trisomy, tetrasomy, balanced (2:2) tetrasomy, unbalanced (3:1) tetrasomy, other aneuploidy, and they may additionally involve unbalanced translocations, balanced translocations, Robertsonian translocations, recombinations, deletions, insertions, crossovers, and combinations thereof.

In some embodiments, the knowledge of the determined ploidy state may be used to make a clinical decision. This knowledge, typically stored as a physical arrangement of matter in a memory device, may then be transformed into a report. The report may then be acted upon. For example, the clinical decision may be to terminate the pregnancy; alternately, the clinical decision may be to continue the pregnancy. In some embodiments the clinical decision may involve an intervention designed to decrease the severity of the phenotypic presentation of a genetic disorder, or a decision to take relevant steps to prepare for a special needs child.

In one embodiment of the present disclosure, any of the methods described herein may be modified to allow for multiple targets to come from same target individual, for example, multiple blood draws from the same pregnant mother. This may improve the accuracy of the model, as multiple genetic measurements may provide more data with which the target genotype may be determined. In one embodiment, one set of target genetic data served as the primary data which was reported, and the other served as data to double-check the primary target genetic data. In one embodiment, a plurality of sets of genetic data, each measured from genetic material taken from the target individual, are considered in parallel, and thus both sets of target genetic data serve to help determine which sections of parental genetic data, measured with high accuracy, composes the fetal genome.

In some embodiments the source of the genetic material to be used in determining the genetic state of the fetus may be fetal cells, such as nucleated fetal red blood cells, isolated from the maternal blood. The method may involve obtaining a blood sample from the pregnant mother. The method may involve isolating a fetal red blood cell using visual techniques, based on the idea that a certain combination of colors are uniquely associated with nucleated red blood cell, and a similar combination of colors is not associated with any other present cell in the maternal blood. The combination of colors associated with the nucleated red blood cells may include the red color of the hemoglobin around the nucleus, which color may be made more distinct by staining, and the color of the nuclear material which can be stained, for example, blue. By isolating the cells from maternal blood and spreading them over a slide, and then identifying those points at which one sees both red (from the Hemoglobin) and blue (from the nuclear material) one may be able to identify the location of nucleated red blood cells. One may then extract those nucleated red blood cells using a micromanipulator, use genotyping and/or sequencing techniques to measure aspects of the genotype of the genetic material in those cells.

In one embodiment, one may stain the nucleated red blood cell with a die that only fluoresces in the presence of fetal hemoglobin and not maternal hemoglobin, and so remove the ambiguity between whether a nucleated red blood cell is derived from the mother or the fetus. Some embodiments of the present disclosure may involve staining or otherwise marking nuclear material. Some embodiments of the present disclosure may involve specifically marking fetal nuclear material using fetal cell specific antibodies.

There are many other ways to isolate fetal cells from maternal blood, or fetal DNA from maternal blood, or to enrich samples of fetal genetic material in the presence of maternal genetic material. Some of these methods are listed here, but this is not intended to be an exhaustive list. Some appropriate techniques are listed here for convenience: using fluorescently or otherwise tagged antibodies, size exclusion chromatography, magnetically or otherwise labeled affinity tags, epigenetic differences, such as differential methylation between the maternal and fetal cells at specific alleles, density gradient centrifugation succeeded by CD45/14 depletion and CD71-positive selection from CD45/14 negative-cells, single or double Percoll gradients with different osmolalities, or galactose specific lectin method.

In one embodiment of the present disclosure, the target individual is a fetus, and the different genotype measurements are made on a plurality of DNA samples from the fetus. In some embodiments of the present disclosure, the fetal DNA samples are from isolated fetal cells where the fetal cells may be mixed with maternal cells. In some embodiments of the present disclosure, the fetal DNA samples are from free floating fetal DNA, where the fetal DNA may be mixed with free floating maternal DNA. In some embodiments, the fetal DNA may be mixed with maternal DNA in ratios ranging from 99.9:0.1% to 99:1%; 99:1% to 90:10%; 90:10% to 50:50%; 50:50% to 10:90%; or 10:90% to 1:99%; 1:99% to 0.1:99.9%.

In one embodiment, the method may be used for the purpose of paternity testing. For example, given the SNP-based genotypic information from the mother, and from a man who may or may not be the genetic father, and the measured genotypic information from the mixed sample, it is possible to determine if the genotypic information of the male indeed represents that actual genetic father of the gestating fetus. A simple way to do this is to simply look at the contexts where the mother is AA, and the possible father is AB or BB. In these cases, one may expect to see the father contribution half (AA|AB) or all (AA|BB) of the time, respectively. Taking into account the expected ADO, it is straightforward to determine whether or not the fetal SNPs that are observed are correlated with those of the possible father.

One embodiment of the present disclosure could be as follows: a pregnant woman wants to know if her fetus is afflicted with Down Syndrome, and/or if it will suffer from Cystic Fibrosis, and she does not wish to bear a child that is afflicted with either of these conditions. A doctor takes her blood, and stains the hemoglobin with one marker so that it appears clearly red, and stains nuclear material with another marker so that it appears clearly blue. Knowing that maternal red blood cells are typically anuclear, while a high proportion of fetal cells contain a nucleus, he is able to visually isolate a number of nucleated red blood cells by identifying those cells that show both a red and blue color. The doctor picks up these cells off the slide with a micromanipulator and sends them to a lab which amplifies and genotypes ten individual cells. By using the genetic measurements, the PARENTAL SUPPORT™ method is able to determine that six of the ten cells are maternal blood cells, and four of the ten cells are fetal cells. If a child has already been born to a pregnant mother, PARENTAL SUPPORT™ can also be used to determine that the fetal cells are distinct from the cells of the born child by making reliable allele calls on the fetal cells and showing that they are dissimilar to those of the born child. Note that this method is similar in concept to the paternal testing embodiment of the present disclosure. The genetic data measured from the fetal cells may be of very poor quality, containing many allele drop outs, due to the difficulty of genotyping single cells. The clinician is able to use the measured fetal DNA along with the reliable DNA measurements of the parents to infer aspects of the genome of the fetus with high accuracy using PARENTAL SUPPORT™, thereby transforming the genetic data contained on genetic material from the fetus into the predicted genetic state of the fetus, stored on a computer. The clinician is able to determine both the ploidy state of the fetus, and the presence or absence of a plurality of disease-linked genes of interest. It turns out that the fetus is euploidy, and is not a carrier for cystic fibrosis, and the mother decides to continue the pregnancy.

In another embodiment, a couple where the mother, who is pregnant, and is of advanced maternal age wants to know whether the gestating fetus has Down syndrome, Turner Syndrome, Prader Willi syndrome, or some other chromosomal abnormality. The obstetrician takes a blood draw from the mother and father. The blood is sent to a laboratory, where a technician centrifuges the maternal sample to isolate the plasma and the buffy coat. The DNA in the buffy coat and the paternal blood sample are transformed through amplification and the genetic data encoded in the amplified genetic material is further transformed from molecularly stored genetic data into electronically stored genetic data by running the genetic material on a SNP array to measure the parental genotypes. The plasma sample is may be further processed by a method such as running a gel, or using a size exclusion column, to isolate specific size fractions of DNA; specifically, molecules of DNA that are shorter than 500 bases are isolated. The mixture of short DNA fragments is prepared into a DNA library suitable for sequencing. The preparation may involve preferential enrichment of certain polymorphic alleles. The preferential enrichment may involve hybrid capture techniques, PCR based selective amplifications techniques, circularizing probe based targeting techniques, or other targeting techniques. Other methods may be used to enrich the fraction of fetal DNA in the sample. The DNA may then be sequenced using a high throughput sequencing method, for example, using the ILLUMINA GAIIx GENOME ANALYZER. The sequencing transforms the information that is encoded molecularly in the DNA into information that is encoded electronically in computer hardware. An informatics based technique that includes the presently disclosed embodiments, such as PARENTAL SUPPORT™, may be used to determine the ploidy state of the fetus. It is determined that the fetus has Down syndrome. A report is printed out, or sent electronically to the pregnant woman's obstetrician, who transmits the diagnosis to the woman. The woman, her husband, and the doctor sit down and discuss the options. The couple decides to terminate the pregnancy based on the knowledge that the fetus is afflicted with a trisomic condition.

In another embodiment, a pregnant woman, hereafter referred to as "the mother" may decide that she wants to know whether or not her fetus(es) are carrying any genetic abnormalities or other conditions. She may want to ensure that there are not any gross abnormalities before she is confident to continue the pregnancy. She may go to her obstetrician, who may take a sample of her blood. He may also take a genetic sample, such as a buccal swab, from her cheek. He may also take a genetic sample from the father of the fetus, such as a buccal swab, a sperm sample, or a blood sample. He may send the samples to a clinician. The clinician may enrich the fraction of free floating fetal DNA in the maternal blood sample. The clinician may enrich the fraction of enucleated fetal blood cells in the maternal blood sample. The clinician may use various aspects of the method described herein to determine genotypic data of the fetus. That genotypic data may include the ploidy state of the fetus, and/or the identity of one or a number of alleles in the fetus. A report may be generated summarizing the results of the prenatal diagnosis. The report may be transmitted or mailed to the doctor, who may tell the mother the genetic state of the fetus. The mother may decide to discontinue the pregnancy based on the fact that the fetus has one or more chromosomal, or genetic abnormalities, or undesirable conditions. She may also decide to continue the pregnancy based on the fact that the fetus does not have any gross chromosomal or genetic abnormalities, or any genetic conditions of interest.

Another example may involve a pregnant woman who has been artificially inseminated by a sperm donor, and is pregnant. She is wants to minimize the risk that the fetus she is carrying has a genetic disease. She has blood drawn at a phlebotomist, and techniques described in this disclosure are used to isolate three nucleated fetal red blood cells, and a tissue sample is also collected from the mother and genetic father. The genetic material from the fetus and from the mother and father are amplified as appropriate and genotyped using the ILLUMINA INFINIUM BEADARRAY, and the methods described herein clean and phase the parental and fetal genotype with high accuracy, as well as to make ploidy calls for the fetus. The fetus is found to be euploid, and phenotypic susceptibilities are predicted from the reconstructed fetal genotype, and a report is generated and sent to the mother's physician so that they can decide what clinical decisions may be best.

In one embodiment, the raw genetic material of the mother and father is transformed by way of amplification to an amount of DNA that is similar in sequence, but larger in quantity. Then, by way of a genotyping method the genotypic data that is encoded by nucleic acids is transformed into genetic measurements that may be stored physically and/or electronically on a memory device, such as those described above. The relevant algorithms that makeup the PARENTAL SUPPORT™ algorithm, relevant parts of which are discussed in detail herein, are translated into a computer program, using a programming language. Then, through the execution of the computer program on the computer hardware, instead of being physically encoded bits and bytes, arranged in a pattern that represents raw measurement data, they become transformed into a pattern that represents a high confidence determination of the ploidy state of the fetus. The details of this transformation will rely on the data itself and the computer language and hardware system used to execute the method described herein, but is predictable if those contexts are known. Then, the data that is physically configured to represent a high quality ploidy determination of the fetus is transformed into a report which may be sent to a health care practitioner. This transformation may be carried out using a printer or a computer display. The report may be a printed copy, on paper or other suitable medium, or else it may be electronic. In the case of an electronic report, it may be transmitted, it may be physically stored on a memory device at a location on the computer accessible by the health care practitioner; it also may be displayed on a screen so that it may be read. In the case of a screen display, the data may be transformed to a readable format by causing the physical transformation of pixels on the display device. The transformation may be accomplished by way of physically firing electrons at a phosphorescent screen, by way of altering an electric charge that physically changes the transparency of a specific set of pixels on a screen that may lie in front of a substrate that emits or absorbs photons. This transformation may be accomplished by way of changing the nanoscale orientation of the molecules in a liquid crystal, for example, from nematic to cholesteric or smectic phase, at a specific set of pixels. This transformation may be accomplished by way of an electric current causing photons to be emitted from a specific set of pixels made from a plurality of light emitting diodes arranged in a meaningful pattern. This transformation may be accomplished by any other way used to display information, such as a computer screen, or some other output device or way of transmitting information. The health care practitioner may then act on the report, such that the data in the report is transformed into an action. The action may be to continue or discontinue the pregnancy, in which case a gestating fetus with a genetic abnormality is transformed into non-living fetus. The transformations listed herein may be aggregated, such that, for example, one may transform the genetic material of a pregnant mother and the father, through a number of steps outlined in this disclosure, into a medical decision consisting of aborting a fetus with genetic abnormalities, or consisting of continuing the pregnancy. Alternately, one may transform a set of genotypic measurements into a report that helps a physician treat his pregnant patient.

In one embodiment of the present disclosure, the method described herein can be used to determine the ploidy state of a fetus even when the host mother, i.e. the woman who is pregnant, is not the biological mother of the fetus she is carrying.

Some of the math in the presently disclosed embodiments makes hypotheses concerning a limited number of states of aneuploidy. In some cases, for example, only zero, one or two chromosomes are expected to originate from each parent. In some embodiments of the present disclosure, the mathematical derivations can be expanded to take into account other forms of aneuploidy, such as quadrosomy, where three chromosomes originate from one parent, pentasomy, hexasomy etc., without changing the fundamental concepts of the present disclosure. At the same time, it is possible to focus on a smaller number of ploidy states, for example, only trisomy and disomy. Note that ploidy determinations that indicate a non-whole number of chromosomes may indicate mosaicism in a sample of genetic material.

In some embodiments, the genetic abnormality is a type of aneuploidy, such as Down syndrome (or trisomy 21), Edwards syndrome (trisomy 18), Patau syndrome (trisomy 13), Turner Syndrome (45×0) Klinefelter's syndrome (a male with 2× chromosomes), Prader-Willi syndrome, and DiGeorge syndrome. Congenital disorders, such as those listed in the prior sentence, are commonly undesirable, and the knowledge that a fetus is afflicted with one or more phenotypic abnormalities may provide the basis for a decision to terminate the pregnancy, to take necessary precautions to prepare for the birth of a special needs child, or to take some therapeutic approach meant to lessen the severity of a chromosomal abnormality.

All patents, patent applications, and published references cited herein are hereby incorporated by reference in their entirety. While the methods of the present disclosure have been described in connection with the specific embodiments thereof, it will be understood that it is capable of further modification. Furthermore, this application is intended to cover any variations, uses, or adaptations of the methods of the present disclosure, including such departures from the present disclosure as come within known or customary practice in the art to which the methods of the present disclosure pertain, and as fall within the scope of the appended claims.

What is claimed is:

1. A method for determining the number of copies of a chromosome or chromosome segment of interest in the genome of at least one gestating fetus, the method comprising:

sequencing DNA from a first fraction of each mixed sample in a plurality of mixed samples from a plurality of pregnant mothers to obtain a first set of measured genetic data at a plurality of loci on a chromosome or chromosome segment of interest; wherein each mixed sample comprises DNA from a fetus and DNA from the mother of the fetus;

generating a plurality of hypotheses specifying the number of copies of the chromosome or chromosome segment of interest in the genome of at least one of the fetuses;

determining, on a computer, a first probability for each of the hypotheses using the first set of measured genetic data;

sequencing DNA from a second fraction of a least one of the mixed samples for which the first probability of an aneuploid number of copies of the chromosome or chromosome segment of interest is above a threshold value to obtain a second set of measured genetic data at the plurality of loci on the chromosome or chromosome segment of interest;

determining, on a computer, a second probability for each of the hypotheses using the second set of measured genetic data and optionally the first set of measured genetic data;

selecting the hypothesis with the greatest probability for the second probability determination; and outputting the hypothesis with the greatest probability for the second probability determination as an indication of the number of copies of the chromosome or chromosome segment of interest in the genome of at least one of the fetuses.

2. The method of claim 1, comprising shotgun sequencing of randomly selected DNA fragments.

3. The method of claim 1, comprising sequencing non-polymorphic loci.

4. The method of claim 1, comprising sequencing polymorphic loci.

5. The method of claim 1, wherein the method further comprises amplifying the DNA prior to sequencing the DNA.

6. The method of claim 1, comprising:

determining, on a computer, allele ratios at polymorphic loci from the measured genetic data;

creating, on a computer, a joint distribution model for expected allele ratios of each polymorphic locus for each hypothesis using genetic data from one or both biological parents of at least one of the fetuses;

determining, on a computer, the probability of each of the hypotheses using the joint distribution model and the calculated allele ratios;

selecting the hypothesis with the greatest probability; and outputting the hypothesis with the greatest probability for the second probability determination as an indication of the number of copies of the chromosome or chromosome segment of interest in the genome of at least one of the fetuses.

7. The method of claim 1, comprising aggregating the measured genetic data on the chromosome or chromosome segment of interest.

8. The method of claim 1, comprising determining, on a computer, allele ratios at polymorphic loci from the measured genetic data;

aggregating the allele ratios;

determining, on a computer, the probability of each of the hypotheses using the aggregated allele ratios; and selecting the hypothesis with the greatest probability; and outputting the hypothesis with the greatest probability for the second probability determination as an indication of the number of copies of the chromosome or chromosome segment of interest in the genome of at least one of the fetuses.

9. The method of claim 7, wherein determining the number of copies of the chromosome or chromosome segment of interest comprises comparing the aggregated value for the chromosome or chromosome segment of interest to the aggregated value for one or more chromosomes expected to be disomic.

10. The method of claim 1, wherein determining the number of copies of the chromosome or chromosome segment of interest comprises comparing the total number of sequence reads that map to the chromosome or chromosome segment of interest to the total number of sequence reads that map to one or more other chromosomes.

11. The method of claim 10, wherein the total number of sequence reads that map to the chromosome or chromosome segment of interest or the total number of sequence reads that map to one or more other chromosomes is adjusted for bias.

12. The method of claim 1, wherein determining the number of copies of the chromosome or chromosome segment of interest comprises comparing the mean value of sequence reads that map to the chromosome or chromosome segment of interest to the mean value of sequence reads that map to one or more other chromosomes.

13. The method of claim 1, wherein determining the number of copies of the chromosome or chromosome segment of interest comprises comparing the mean of the allele ratios for the chromosome or chromosome segment of interest to the mean of the allele ratios for one or more other chromosomes.

14. The method of claim 1, comprising for at least one of the mixed samples:

distributing the mixed sample into a plurality of reaction samples to randomly provide individual reaction samples that contain a sequence from the chromosome or chromosome segment of interest and individual reaction samples that do not contain a sequence from the chromosome or chromosome segment of interest;

sequencing the DNA in the individual reaction samples to provide a first number of binary results representing presence or absence of a presumably euploid fetal chromosome or chromosome segment in the reaction samples and a second number of binary results representing presence or absence of a possibly aneuploid fetal chromosome or chromosome segment of interest in the reaction samples;

determining an expected distribution of a number of binary results for a presumably euploid fetal chromosome or chromosome segment in the reaction samples using the first number;

determining an expected distribution of a number of binary results for a presumably aneuploid fetal chromosome or chromosome segment in the reaction samples using the first number and the ratio of fetal to maternal DNA found in the mixed sample; and using a maximum likelihood estimation to select the hypothesis with the greatest probability, thereby determining the number of copies of the chromosome or chromosome segment of interest in the genome of at least one of the fetuses.

15. The method of claim 1, further comprising determining the ratio of fetal to maternal DNA in each of the mixed samples by calculating a maximum likelihood estimate of the ratio of fetal to maternal DNA.

16. The method of claim 1, further comprising determining the ratio of fetal to maternal DNA in each of the mixed samples by:

identifying polymorphic loci where the father of the fetus has an allele that is not present in the mother of the fetus; and using the amount of the allele possessed by the father but not by the mother in each of the mixed samples for each of the identified polymorphic loci to determine the ratio of fetal to maternal DNA in each of the mixed samples.

17. The method of claim 1, comprising measuring the difference in methylation between one or more maternal and fetal alleles.

18. The method of claim 1, wherein determining the number of copies of the chromosome or chromosome segment of interest comprises determining the presence or absence of a deletion or duplication.

19. The method of claim 1, wherein the mixed samples are isolated from maternal blood.

20. The method of claim 1, wherein determining the probability of each of the hypotheses comprises comparing the measured genetic data to either (i) a threshold value or (ii) a value for a disomic chromosome or chromosome segment.

21. A method for determining the number of copies of a chromosome or chromosome segment of interest in the genome of at least one gestating fetus, the method comprising:

measuring DNA from a first fraction of each mixed sample in a plurality of mixed samples from a plurality of pregnant mothers to obtain a first set of measured genetic data at a plurality of loci on a chromosome or chromosome segment of interest; wherein each mixed sample comprises DNA from a fetus and DNA from the mother of the fetus;

determining a parameter by analyzing the first set of measured genetic data;

sequencing DNA from a second fraction of a least one of the mixed samples for which the parameter is above or below a threshold value to obtain a second set of measured genetic data at the plurality of loci on the chromosome or chromosome segment of interest;

determining, on a computer, a z-score for at least one possible number of copies of the chromosome or chromosome segment of interest in the genome of at least one of the fetuses using the second set of measured genetic data and optionally the first set of measured genetic data;

selecting the number of copies of the chromosome or chromosome segment of interest that is most likely to be correct based on the z-score; and outputting the selected number of copies of the chromosome or chromosome segment of interest in the genome of at least one of the fetuses.

22. The method of claim 21, comprising determining a number of sequence reads to be obtained from at least one of the second fractions using the parameter.

23. The method of claim 21, wherein the analyzing the first set of measured genetic data comprises:

creating a plurality of hypotheses specifying the number of copies of the chromosome or chromosome segment of interest in the genome of at least one of the fetuses; and determining, on a computer, a first probability for each of the hypotheses using the first set of measured genetic data; wherein the parameter is the probability of the hypothesis with the greatest probability.

24. The method of claim 21, wherein the parameter is a Z-score.

25. The method of claim 21, wherein the parameter is a ratio of fetal to maternal DNA in the mixed sample.

26. The method of claim 21, wherein the parameter is the number of loci in the plurality of loci.

27. A method for determining the number of copies of a chromosome or chromosome segment of interest in the genome of a cancer in at least one individual, the method comprising:

sequencing DNA from a first fraction of each mixed sample in a plurality of mixed samples from a plurality of individuals to obtain a first set of measured genetic data at a plurality of loci on a chromosome or chromosome segment of interest; wherein each mixed sample comprises DNA from a cancer and DNA not from a cancer;

generating a plurality of hypotheses specifying the number of copies of the chromosome or chromosome segment of interest in the genome of at cancer in least one of the individuals;

determining, on a computer, a first probability for each of the hypotheses using the first set of measured genetic data;

sequencing DNA from a second fraction of a least one of the mixed samples for which the first probability of an aneuploid number of copies of the chromosome or chromosome segment of interest is above a threshold value to obtain a second set of measured genetic data at the plurality of loci on the chromosome or chromosome segment of interest;

determining, on a computer, a second probability for each of the hypotheses using the second set of measured genetic data and optionally the first set of measured genetic data; and selecting the hypothesis with the greatest probability for the second probability determination; and outputting the hypothesis with the greatest probability for the second probability determination as an indication of the number of copies of the chromosome or chromosome segment of interest in the genome of a cancer in at least one individual.

28. The method of claim 27, comprising sequencing polymorphic loci.

29. A method for determining the number of copies of a chromosome or chromosome segment of interest in the genome of a cancer in at least one individual, the method comprising:

measuring DNA from a first fraction of each mixed sample in a plurality of mixed samples from a plurality of individuals to obtain a first set of measured genetic data at a plurality of loci on a chromosome or chromosome segment of interest; wherein each mixed sample comprises DNA from a cancer and DNA not from a cancer;

determining a parameter by analyzing the first set of measured genetic data;

sequencing DNA from a second fraction of a least one of the mixed samples for which the parameter is above or below a threshold value to obtain a second set of measured genetic data at the plurality of loci on the chromosome or chromosome segment of interest;

determining, on a computer, a z-score for at least one possible number of copies of the chromosome or chromosome segment of interest in the genome of a cancer in at least one individual using the second set of measured genetic data and optionally the first set of measured genetic data;

selecting the number of copies of the chromosome or chromosome segment of interest that is most likely to be correct based on the z-score; and outputting the selected number of copies of the chromosome or chromosome segment of interest in the genome of a cancer in at least one individual.

30. The method of claim 29, wherein the parameter is a Z-score.

* * * * *